(12) United States Patent
Trudeau et al.

(10) Patent No.: US 8,597,357 B2
(45) Date of Patent: Dec. 3, 2013

(54) SYSTEM AND METHOD FOR SIZING, INSERTING AND SECURING ARTIFICIAL DISC IN INTERVERTEBRAL SPACE

(75) Inventors: Jeffrey Trudeau, Marquette, MI (US); Brian Janowski, Marquette, MI (US); Thomas Kilpela, Marquette, MI (US); Tim Brown, Negaunee, MI (US); Michael Jackson, Hancock, MI (US); Qi-Bin Bao, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 1370 days.

(21) Appl. No.: 11/856,667

(22) Filed: Sep. 17, 2007

(65) Prior Publication Data

US 2008/0103598 A1    May 1, 2008

Related U.S. Application Data

(60) Provisional application No. 60/825,865, filed on Sep. 15, 2006, provisional application No. 60/912,138, filed on Apr. 16, 2007.

(51) Int. Cl.
*A61F 2/44* (2006.01)

(52) U.S. Cl.
USPC ...................................................... 623/17.14

(58) Field of Classification Search
USPC ..................... 623/17.11–17.16; 606/280–299
See application file for complete search history.

(56) References Cited

U.S. PATENT DOCUMENTS

| | | | |
|---|---|---|---|
| 4,636,217 A | 1/1987 | Ogilvie et al. | |
| 4,759,769 A | 7/1988 | Hedman et al. | |
| 5,123,926 A | 6/1992 | Pisharodi | |
| 5,314,477 A | 5/1994 | Marnay | |
| 5,425,773 A | 6/1995 | Boyd et al. | |
| 5,507,816 A | 4/1996 | Bullivant | |
| 5,676,701 A | 10/1997 | Yuan | |
| 5,800,547 A | 9/1998 | Schaefer et al. | |
| 5,888,226 A | 3/1999 | Rogozinski | |

(Continued)

FOREIGN PATENT DOCUMENTS

| | | |
|---|---|---|
| CA | 2 548 780 | 7/2005 |
| DE | 296 12 269 U1 | 10/1996 |

(Continued)

OTHER PUBLICATIONS

International Search report dated Apr. 23, 2008, from corresponding International Patent Application No. PCT/US2007/078679.

(Continued)

*Primary Examiner* — Matthew Lawson
(74) *Attorney, Agent, or Firm* — Fitch, Even, Tabin & Flannery LLP

(57) ABSTRACT

A prosthetic spinal implant having a deployable securing mechanism that is deployable into a portion of the vertebral space for affixing the implant between the vertebrae, the securing mechanism having tactile feedback means comprising a surface for transmitting tactile feedback during deployment of the securing mechanism. A spinal implant having deployable securing means that interface with the implant to prevent the deployable securing means from retracting after deployment. An implant that utilizes its resilient properties to provide the user with tactile feedback with which the user may ascertain the position of the securing mechanism. A system and tools for sizing and implanting implants with the aforementioned characteristics.

31 Claims, 64 Drawing Sheets

(56) References Cited

U.S. PATENT DOCUMENTS

| | | |
|---|---|---|
| 6,039,763 A | 3/2000 | Shelokov |
| 6,146,421 A | 11/2000 | Gordon et al. |
| 6,210,422 B1 * | 4/2001 | Douglas .................. 606/194 |
| 6,210,442 B1 | 4/2001 | Wing et al. |
| 6,371,987 B1 | 4/2002 | Weiland et al. |
| 6,540,785 B1 | 4/2003 | Gill |
| 6,610,093 B1 | 8/2003 | Pisharodi |
| 6,767,367 B1 | 7/2004 | Michelson |
| 6,770,096 B2 | 8/2004 | Bolger et al. |
| 6,923,830 B2 | 8/2005 | Michelson |
| 6,926,737 B2 | 8/2005 | Jackson |
| 6,936,071 B1 | 8/2005 | Marnay et al. |
| 6,981,975 B2 | 1/2006 | Michelson |
| 7,056,341 B2 | 6/2006 | Crozet |
| 7,074,240 B2 | 7/2006 | Pisharodi |
| 7,662,182 B2 * | 2/2010 | Zubok et al. ............... 623/17.11 |
| 7,682,397 B2 | 3/2010 | Berry et al. |
| 7,794,465 B2 * | 9/2010 | Marik et al. .................. 606/87 |
| 7,819,920 B2 | 10/2010 | Assaker |
| 7,909,859 B2 * | 3/2011 | Mosca et al. .................. 606/289 |
| 8,038,678 B2 | 10/2011 | Schmieding et al. |
| 8,303,660 B1 * | 11/2012 | Abdou ..................... 623/17.14 |
| 2002/0035400 A1 | 3/2002 | Bryan et al. |
| 2002/0165613 A1 | 11/2002 | Lin et al. |
| 2003/0149484 A1 | 8/2003 | Michelson |
| 2004/0006394 A1 | 1/2004 | Lipman et al. |
| 2004/0044410 A1 | 3/2004 | Ferree et al. |
| 2004/0093082 A1 | 5/2004 | Ferree |
| 2004/0193272 A1 * | 9/2004 | Zubok et al. ............... 623/17.11 |
| 2004/0243240 A1 | 12/2004 | Beaurain et al. |
| 2005/0038515 A1 | 2/2005 | Kunzler |
| 2005/0071010 A1 | 3/2005 | Crozet |
| 2005/0080488 A1 | 4/2005 | Schultz |
| 2005/0107881 A1 | 5/2005 | Alleyne et al. |
| 2005/0273166 A1 | 12/2005 | Sweeney |
| 2006/0004453 A1 | 1/2006 | Bartish |
| 2006/0020341 A1 | 1/2006 | Schneid et al. |
| 2006/0085076 A1 | 4/2006 | Krishna et al. |
| 2006/0095136 A1 | 5/2006 | McLuen |
| 2006/0116767 A1 | 6/2006 | Magerl et al. |
| 2006/0136062 A1 | 6/2006 | DiNello et al. |
| 2006/0178744 A1 | 8/2006 | de Villiers et al. |
| 2006/0178745 A1 | 8/2006 | Bartish, Jr. et al. |
| 2006/0195191 A1 | 8/2006 | Sweeney et al. |
| 2006/0212122 A1 | 9/2006 | Perera |
| 2006/0293752 A1 | 12/2006 | Moumene et al. |
| 2007/0055376 A1 | 3/2007 | Michelson |
| 2007/0100455 A1 | 5/2007 | Parsons |
| 2007/0270961 A1 * | 11/2007 | Ferguson ................... 623/17.11 |
| 2007/0288005 A1 | 12/2007 | Arnin et al. |
| 2008/0103598 A1 | 5/2008 | Trudeau et al. |
| 2009/0240333 A1 | 9/2009 | Trudeau et al. |
| 2010/0016974 A1 | 1/2010 | Janowski et al. |
| 2010/0280619 A1 | 11/2010 | Yuan et al. |

FOREIGN PATENT DOCUMENTS

| | | |
|---|---|---|
| DE | 198 16 832 C1 | 1/2000 |
| WO | 0049977 | 8/2000 |
| WO | 2006016384 | 2/2006 |

OTHER PUBLICATIONS

International Search Report dated Jun. 22, 2009, from corresponding International Patent Application No. PCT/US2009/042882, 2pp.

European Patent Office, Supplementary European Search Report from corresponding International Patent Application No. PCT/US2007/078679, Jan. 28, 2013, 10 pp.

* cited by examiner

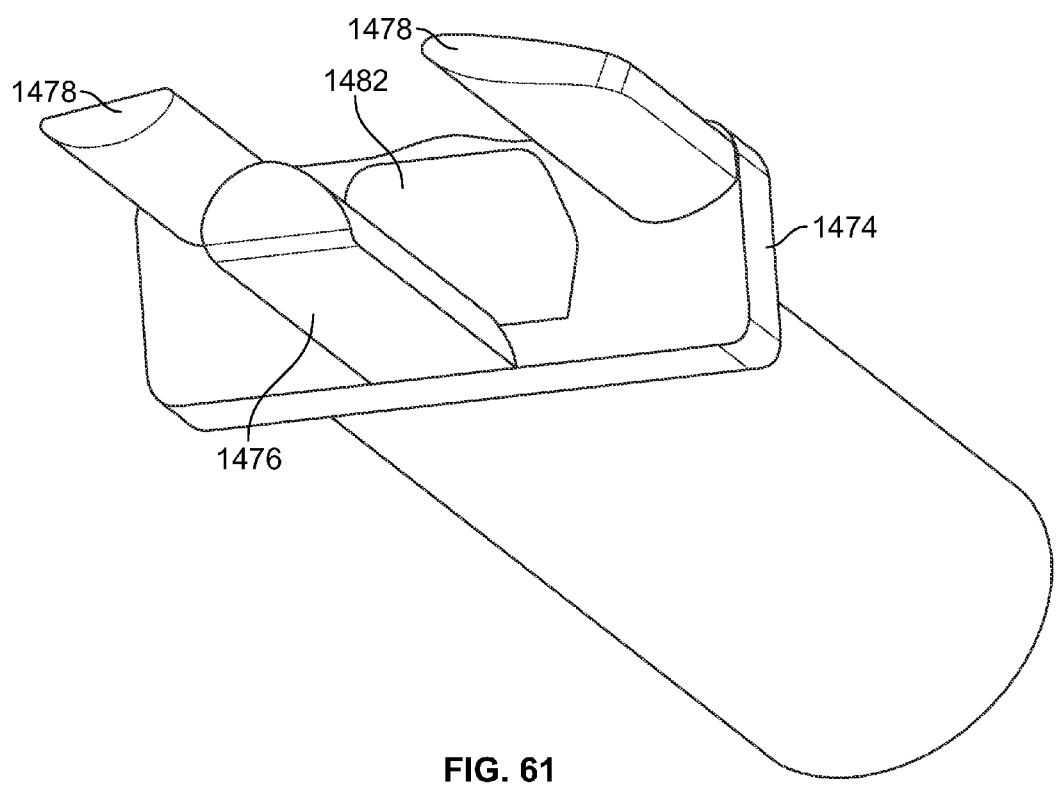
FIG. 61
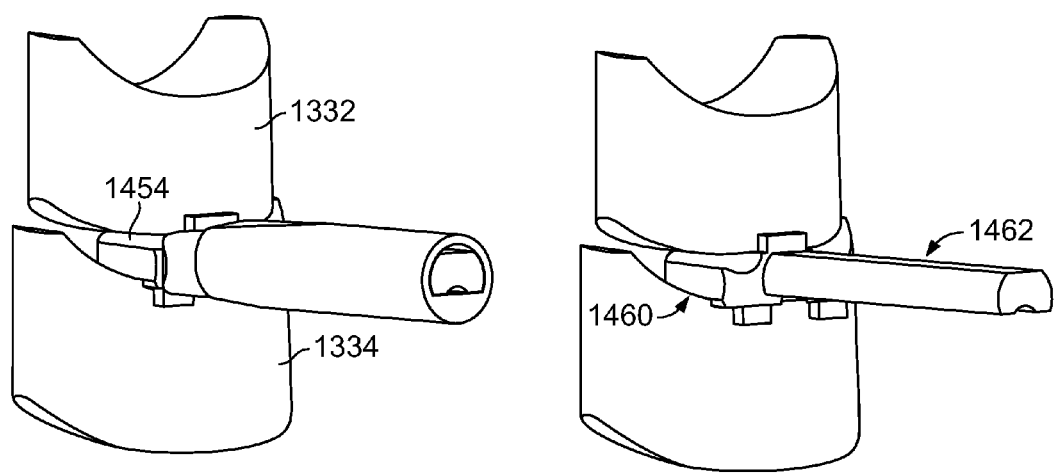
FIG. 62  FIG. 63

SYSTEM AND METHOD FOR SIZING, INSERTING AND SECURING ARTIFICIAL DISC IN INTERVERTEBRAL SPACE

RELATED APPLICATIONS

This application is related to Provisional Application No. 60/825,865, filed Sep. 15, 2006, and Provisional Application No. 60/912,138, filed Apr. 16, 2007, both of which are also incorporated herein by reference in their entirety.

FIELD OF THE INVENTION

The invention relates to systems and methods for sizing an intervertebral space and placement of an appropriately sized implant therein and, more particularly, to systems and methods for sizing, inserting and securing an implant in the intervertebral space.

BACKGROUND OF THE INVENTION

Joint degeneration is a common problem that can occur in a variety of joints throughout the human body. The condition typically is more prevalent as the skeletal system ages and is often treated with medications and/or physical therapy. These conservative treatments sometimes meet only limited success. If unsuccessful, the patient typically will continue to experience ongoing pain and limited mobility.

Often the treatment progression leads to a total joint replacement. These replacements have been performed for years in joints such as the hip and the knee. The replacement devices usually comprise some form of a metallic structural component or endplate with an intermediate polyethylene core. It is not unusual for replacements such as these to give 15-20 years of service before requiring some degree of revision.

In the spine, the surgical treatment of choice has been fusion for the treatment of intervertebral disc degeneration. The spinal intervertebral disc is arguably the most important joint in the spine and is situated between the vertebral bodies. The spinal disc is comprised of a tough outer ring called the annulus, and a jelly-like filling called the nucleus. The belief has been that removing the diseased spinal disc(s) and fusing between affected levels will not make a significant difference in the overall mobility of the spine. However, spinal fusion has proved to cause an increase in degeneration at other vertebral levels that must compensate for the loss of motion at the fused level commonly causing the patient to relapse into more pain and limited mobility.

Recently, there has been a focus on the use of "motion preservation" implants over implants that promote spinal fusion. These motion preserving implants, in the form of joint replacements in the spine, hope to alleviate many of the problems associated with fusion devices in the spine. Intervertebral disc replacement devices are seen today typically comprising a pair of biocompatible metal plates with a polymer or elastomeric core, or a metal plate articulating on a metal plate.

Metal on metal implants have a history of failure in long term use, however, precision machining has spawned a reemergence of implants using these materials since it is believed that this change in manufacturing greatly improves the wear. Regardless, the metal implants are radiopaque and continue to frustrate surgeons due to the difficulty in imaging the affected area. Other implants, such as those using a polymer or elastomeric core between metallic plates suffer from the same radiopaque frustrations due to the metal components in addition to the added complexities of design due to the necessity of utilizing a multitude of materials for a single implant.

The prior art discloses a laundry list of biocompatible materials including metals, ceramics, and polymers, that can be used for the manufacture of these implants, yet historically many of these materials have failed when interfaced together and tested in an articulating joint. There is in particular an extensive history of failure when polymers articulate against polymers in weight bearing artificial joints. Due to this failure history, polymer combinations have naturally been excluded as an acceptable self-articulating material combination for use in weight bearing joint replacements.

PEEK (poly-ether-ether-ketone), for example, has been suggested as an appropriate material of manufacture for use in implant devices due in large part to its strength, radiolucent nature, and biocompatibility. This is particularly true in structural implants having no articulating component. PEEK on PEEK has been suggested for use in low wear non-weight bearing joints such as in finger joints. However, the prior art has been careful not to suggest self-articulating PEEK on PEEK as a suitable material combination in weight bearing joint replacement devices due to the failure history of biocompatible polymers articulating against themselves.

SUMMARY OF THE INVENTION

Testing in our laboratories however, told a different and unexpected story. In simulated weight bearing artificial joint configurations, PEEK against PEEK performed very favorably. PEEK articulating against PEEK demonstrated exceptional mechanical performance and biocompatibility characteristics required for load bearing artificial joints used in the human body and in other animals. PEEK may also be manufactured in a fiber reinforced form, typically carbon fiber, which also performs favorably against itself and against non-fiber reinforced PEEK.

Once PEEK was recognized as a viable option for self articulation, it became clear that an entire articulating joint could be made from the material without the need for metallic structural or articulating components. This discovery substantially simplified the nature of weight bearing artificial joint replacement design and great benefits have emerged. A partial list of these benefits include artificial joints that; have less components due to integrating features into the same component that were previously separated due to the need for a plurality of materials to serve the function, will last longer due to favorable wear characteristics, are substantially radiolucent, have a modulus of elasticity closer to the bone tissue they are implanted in, and are ultimately less expensive. It is important to note that less components typically equates to fewer modes of failure, reduced inventory, and simplified manufacturing and assembly. Although less preferred, clearly one may choose to keep the metallic components of an implant system and utilize PEEK on each articulating surface of the artificial joint for a PEEK on PEEK articulation.

Two piece articulating PEEK on PEEK intervertebral implants have been presented in parent applications by the same inventor. These implants perform exceptionally well for replacement of the spinal nucleus. However, many indications require implants of this nature to also comprise improved restraining features particularly in weight bearing applications.

For example, there is a need for a simplified radiolucent artificial disc device, with excellent wear characteristics and features that will secure the device to the vertebral endplates or otherwise restrain it between the vertebral bodies. An artificial disc such as this would be particularly useful as a lumbar disc replacement, and even more so as a cervical disc replacement. The cervical disc is much smaller than the lumbar disc as is the space the cervical disc occupies. For at least this reason, a simplified design utilizing fewer parts is beneficial.

In all cases, the articulating joint surfaces are preferably a combination of PEEK articulating on PEEK, PEEK on carbon reinforced (CR) PEEK, or CR PEEK on CR PEEK. Boney integration of these implants may benefit from prepared osteo-conductive surfaces or coatings described elsewhere in this document.

It is preferable that the radiolucent implant includes one or more small radiopaque markers which will show on up an X-ray image to assist the surgeon in positioning the implant during surgery. The preferred material for these markers is tantalum. Typically these markers will be encased in predetermined locations in the implant at their periphery. Coatings which show up on imaging as a subtle outline of the implant device may also be used.

It is also preferable, although not necessary, that the implants disclosed herein include a layer of osteo-conductive or osteo-inductive surfaces or coatings on those implant surfaces in contact with bone or tissue that will assist in securing the implant in a predetermined location. Typically this will occur through boney integration of the bone with the coating or implant surface. Examples of such coatings are hydroxyapatite, calcium phosphates such as tricalcium phosphate, or porous titanium spray.

The implant devices disclosed herein are particularly suited as intervertebral disc replacements for all or a portion of the natural intervertebral disc. In addition, the securing mechanisms disclosed herein are also suited for other spinal implants, such as vertebral body replacements, spinal cages, and other fusion promoting implants, as well as other known motion preserving implants. The devices have minimal structural parts and are preferably manufactured from specialized materials that are substantially radiolucent such as PEEK or Carbon-Fiber PEEK in both their structural and joint articulating portions.

Generally, the various systems and methods described herein allow for an implant, such as an artificial disc, to be properly sized, implanted and secured in an intervertebral space with the disc having a bearing interface that preserves motion between the upper and lower vertebrae between which the disc is implanted and secured. In each form described herein, a trial spacer is not only used to assess the size of the intervertebral space so that an appropriately sized disc implant can be selected, it is also used to assist in generating features in the vertebrae and/or end plates thereof (hereinafter "vertebral bodies") for a securing mechanism that holds and retains the disc implant in the intervertebral space.

In some forms, the securing mechanism is associated with the implant to be inserted into the intervertebral space therewith. After the disc and securing mechanism are inserted in the intervertebral space, the securing mechanism can be deployed into the preformed features in the adjacent vertebral bodies from the disc implant. In one form, the insertion tool is used to engage the securing mechanism with the preformed features in the intervertebral bodies. In another form, the securing mechanism is actuated directly to engage the securing mechanism with the preformed features of the vertebral bodies.

In yet another form, the securing mechanism is inserted into the intervertebral space via the trial spacer prior to insertion of the disc implant. In this form, the securing mechanism is actuated directly to be deployed into the features in the adjacent vertebral bodies with the disc implant then inserted into the intervertebral space. Thereafter, the securing mechanism is actuated so as to engage both the implant and the vertebral body for securing the implant in the intervertebral space.

In any event, the level of restraint required for a particular orthopedic application will vary. This disclosure also describes examples of a variety of securing mechanisms or alternative features suitable for restraining the device in a predetermined location. The securing mechanisms generally possess structure which allow for dynamic fixation of the implant. Instead of relying solely on subsidence or boney ingrowth of the bone around the features of the implant, the securing mechanisms actively engage the bone for immediate and reliable fixation of the implant to the vertebrae. In one embodiment, a rotatable shaft with at least one bone engaging body is disposed on the implant for securing the implant within the intervertebral space. In an undeployed position, the bone engaging body is disposed within the implant body. When the shaft is rotated, the bone engaging body is deployed into the vertebra and thereby fixes the implant to the vertebra to prevent migration of the implant.

In addition, securing mechanisms according to the present invention may incorporate designs that transmit tactile feedback to the surgeon when the securing mechanism is being operated. As it is very difficult for the surgeon to visually ascertain the position of the implant and its securing features during operation, a surgeon will also use his hands to feel for tactile responses transmitted from the implant and through his tools. In one embodiment, the securing mechanism has a cammed surface for interacting with a corresponding cammed surface to cause the securing mechanism to be biased against the implant to provide resistance against the movement of the securing mechanism that can be felt through the surgeon's tools. In this manner, the surgeon can easily ascertain when the securing mechanism has been fully extended or deployed. The tactile feedback features of the securing mechanism also prevent the securing mechanism from being over- or under-actuated, i.e. deploying the securing mechanism beyond its intended range of motion, or failing to fully deploy the securing mechanism. This condition may result in improper fixation of the implant and cause damage to the implant, spine, nerves, vascular system, or other tissue in the area around the spine.

Another aspect of the current invention includes securing mechanisms for an implant having anti-retraction or derotation prevention means. Some securing mechanisms according to the present invention are deployed or extended into the bone by actuating the securing mechanism, for example, by rotating a shaft. However, it is possible for the securing mechanism to retract or derotate back to its undeployed position over time, due to forces exerted on the implant. Thus, to prevent such an event, a securing mechanism may be provided with means to prevent retraction or derotation. In one embodiment, derotation prevention means are provided in the form of a camming surface on the securing mechanism in combination with a corresponding camming surface on the implant. The camming surfaces are disposed to engage or interfere with one another when the securing mechanism is in a fully deployed position to prevent derotation of the securing mechanism.

BRIEF DESCRIPTION OF THE DRAWINGS

To understand the present invention, it will now be described by way of example, with reference to the accompanying drawings in which:

FIG. 61 is an posterolateral perspective view of the shaft handle of the trial spacer assembly of FIG. 56;

FIG. 62 is an anterolateral perspective view of the trial spacer assembly of FIG. 56 inserted into the intervertebral space;

FIG. 63 is an anterolateral perspective view of the trial spacer assembly of FIG. 56 inserted into the intervertebral space with the handle portion removed;

DETAILED DESCRIPTION OF PREFERRED EMBODIMENTS

Figure 1:
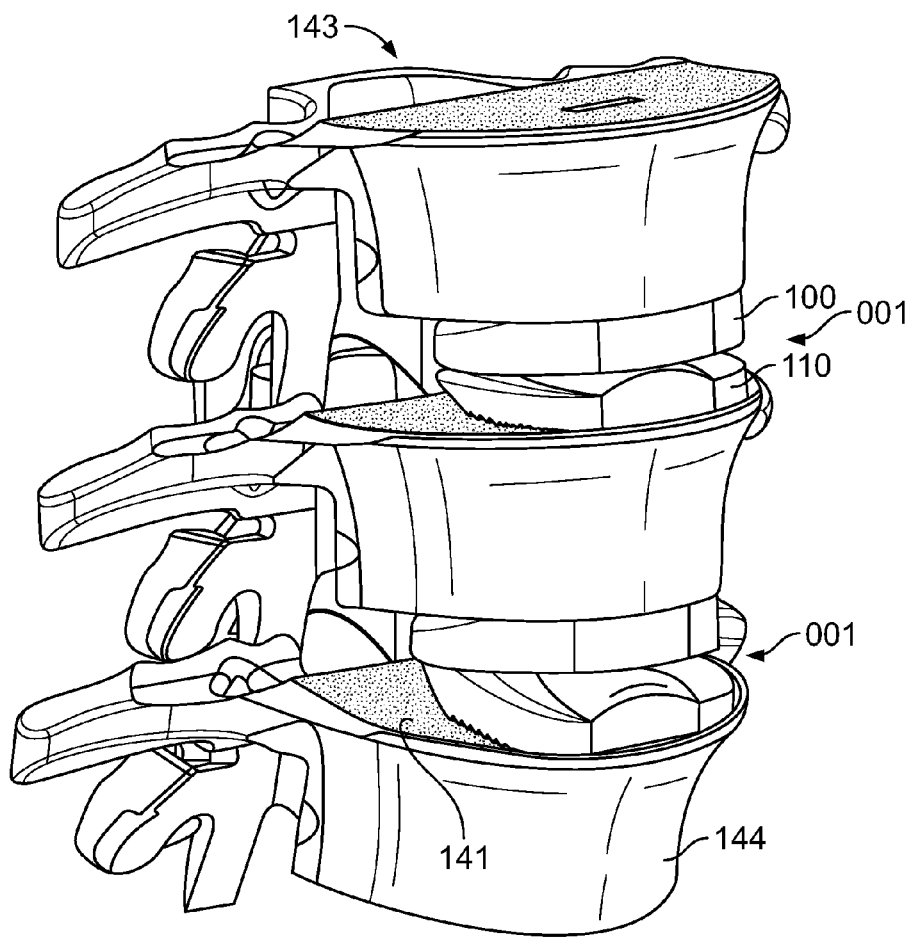
FIG. 1 is a perspective view of an anterior portion of the spine with two implants according to the present invention disposed within the intervertebral spaces.
Figure 2:
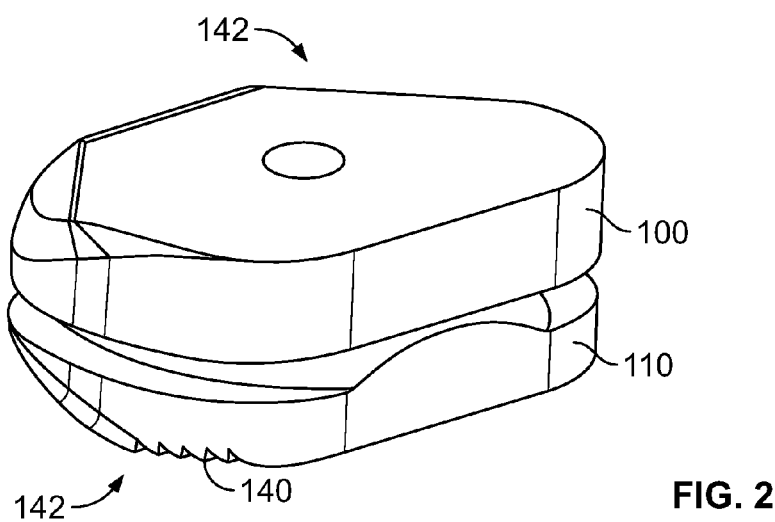
FIG. 2 is an anterolateral perspective view of an implant according to the present invention.
Figure 3:
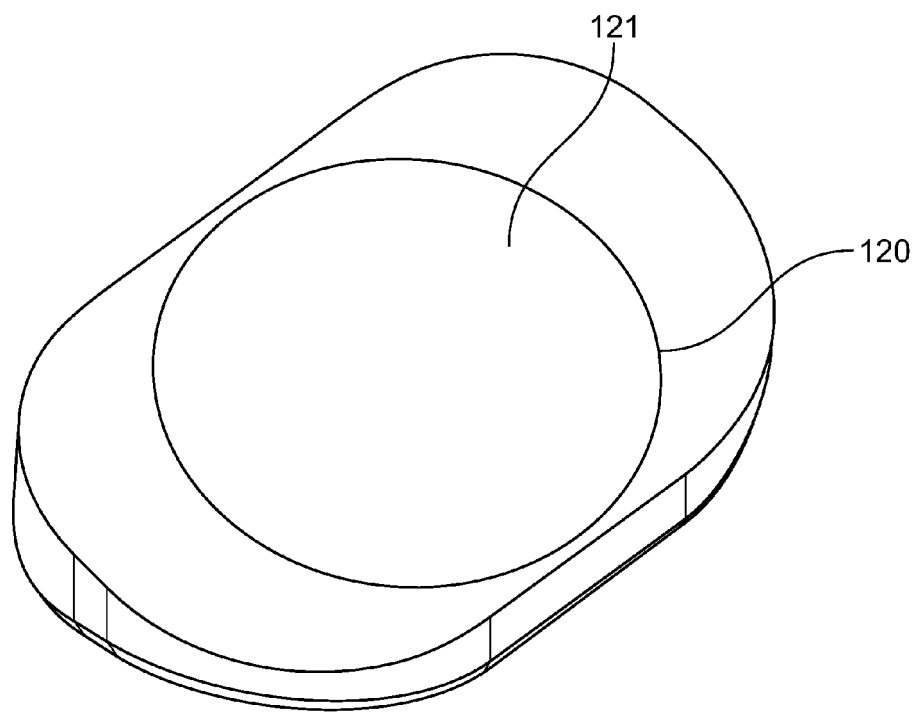
FIG. 3 is a perspective view of one part of a motion preserving implant with a concave articulation surface according to the present invention.

In a preferred embodiment, such as illustrated in FIGS. 1-4, an artificial disc device 001 comprises an upper shell 100 and lower shell 110. The upper shell 100 comprises a substantially concave recess portion 120, and the lower shell 110 comprises a substantially convex portion 130. Although not preferred, the concave and convex portions may be switched such that the upper shell 100 may alternatively comprise the convex portion 130.

Figure 4:
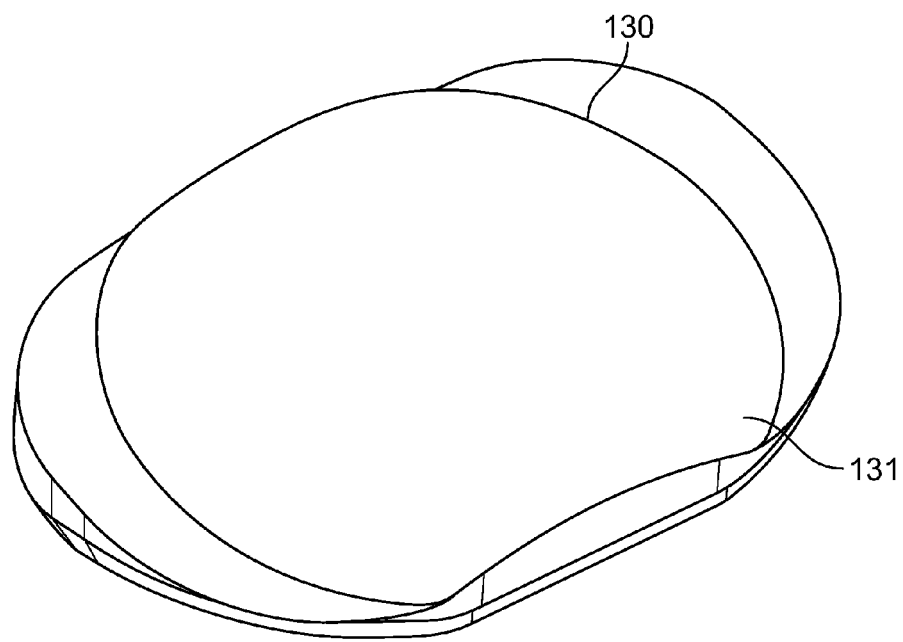
FIG. 4 is a perspective view of a corresponding part of the motion preserving implant of FIG. 3 with a convex articulation surface according to the present invention.

The convex portion 130 comprises a convex articulation surface 131, and the concave portion 120 comprises a concave articulation surface 121. It is preferred that the articulation surfaces 121 and 131 have substantially matching geometries or radiuses of curvature although some mismatch of curvature may be desired to provide a combination of rolling and sliding motion to occur between the articulation surfaces 120 and 121. The geometries may be complex in nature but preferably are ball and socket style. The convex portion 130 and concave portion 120 may extend substantially to the outer perimeter of the shell 100, 110 as illustrated in FIG. 4, or may be formed, typically with a smaller radius of curvature inward a predetermined distance from the outer perimeter of the shell 100, 110. Each shell 100, 110 is preferably manufactured from PEEK or fiber reinforced PEEK or other biocompatible polymer combination or radiolucent material demonstrating very low surface wear in high repetition wear testing.

The artificial disc device 001 preferably comprises one or more restraint portion(s) 220 or structure located on one or both of the shell members 100, 110 to help prevent the shells 100, 110 from becoming dislodged or migrating across the boney endplate 141 of the vertebrae 143 after insertion. For example, the restraining portion 220 may be located on one of the shells 100, 110 on the endplate facing surface 142 in the form of directional teeth 140.

It is preferred that the footprint of the artificial disc device 001 be similar to the footprint of the endplate although generally smaller to fit within the intervertebral space. The endplate facing surfaces 142 are preferably contoured to match the contour of the endplates 141. For example, if the surgeon prepares the endplates to be flat, it is preferred that the endplate facing surfaces 142 are also flat. Likewise, if the endplates 141 are prepared to be concave, it is preferred that the endplate facing surfaces 142 are similarly convex. It should be noted that endplates 141 that are concave will generally retain the artificial disc device 001 better since the device 001 becomes cupped between the vertebrae.

Additional restraining features may be needed to assist holding the artificial disc device 001 in the predetermined position. Described in this application are various securing mechanisms, coatings, or surface preparations that can be used on the endplate facing surfaces 142 to restrain an implant.

Figure 5:
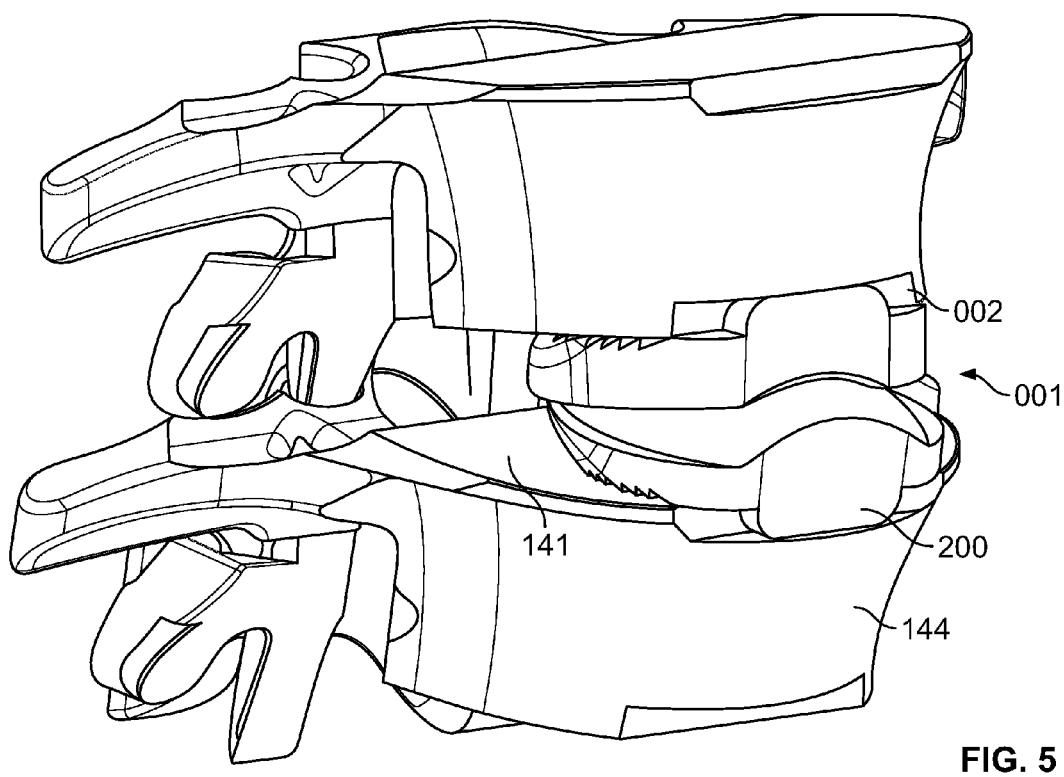
FIG. 5 is an anterolateral perspective view of an implant with securing means according to the present invention implanted within the intervertebral space.

An additional embodiment of a restraint is illustrated in the artificial disc device 001 shown in FIG. 5. In this embodiment, the surgeon may choose to form a recess 002 in the anterior edge of the facing upper and lower vertebrae to accommodate the restraint boss 200. The restraint boss 200 is preferably an extended wall or lip from the endplate facing surface 142 and is of a thickness suitable to block further posterior motion. If the recess 002 is suitably formed into a pocket, the restraint boss 200 will also assist in unwanted lateral motion of the shell 100 or 110. Alternatively, the restraint boss may sit on the anterior bone surface of the vertebral body without the recess 002. The restraint boss 200 may be included on one or both of the shells 100, 110.

Upon insertion of the artificial disc device 001, the restraint boss 200 acts as a stop to the shell 100, 110 as it is guided to the predetermined position. The boss 200 also assures the device is unable to migrate posteriorly towards the spinal cord and cause injury. It is preferred the recess 002 is generally the thickness of the boss 200 such that the boss 200 may be generally flush with the anterior surface of the vertebral body 144.

Figure 6:
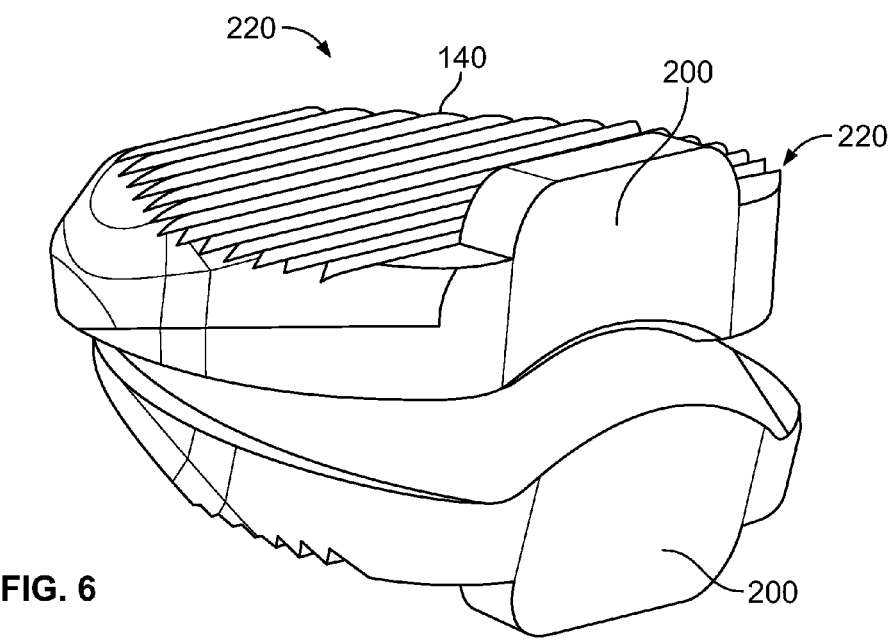
FIG. 6 is an anterolateral perspective view of an implant with securing means according to the present invention.
Figure 6A:
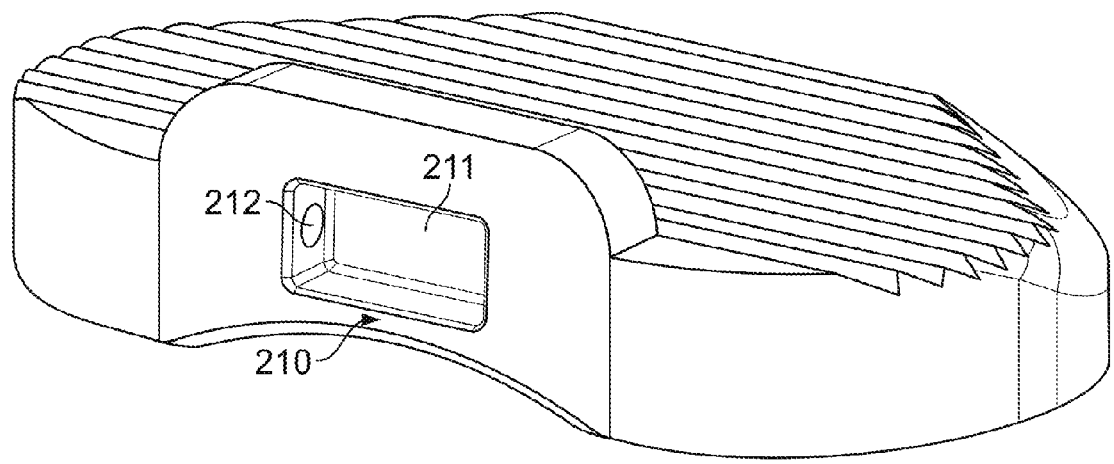
FIG. 6A is an anterolateral perspective view of an implant component with securing means and inserter tool docking means according to the present invention.
Figure 7:
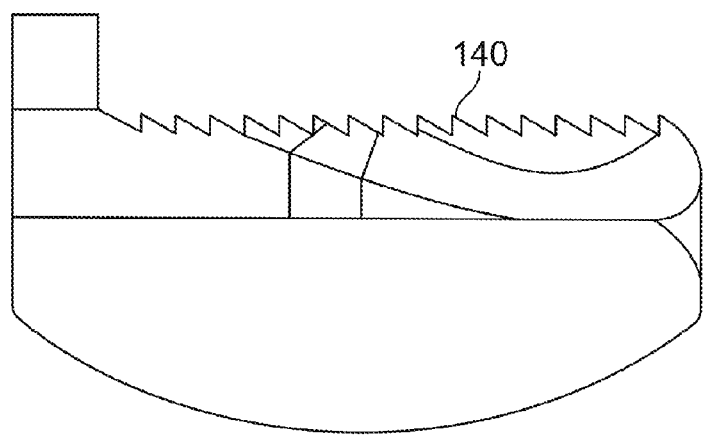
FIG. 7 is a side view of an implant component with securing means according to the present invention.

The shell 100, 110 preferably includes an attachment portion 210 which may be in the form of a boss, hole, post, recess, ridge, flange or other structure for securing of an implant insertion or removal instrument to assist with inserting or removing the implant from the intervertebral space. For example, in the embodiment in FIG. 6A, the attachment portion 210 comprises a window 211 for insertion of the head of an insertion or removal instrument and connection holes 212 for occupation by deployable pins on each end of the window 211 situated in the instrument.

As described earlier, the restraint portion 220 on the endplate facing surfaces 142 may be in the form of directional teeth 140 which are angled like saw teeth to encourage eased insertion across the boney endplate 141 and resist anterior migration to help retain the shell members 100, 110 in the predetermined location between the intervertebral bodies. The actual form of the restraint portion 220, i.e. directional teeth 140 or a surface coating, may be found on one or both shell 100, 110 members. The restraint portion 220 may include different forms of restraint on each shell 100, 110. In addition, more than one form of restraint may be used on each restraining portion 220. For example, the shell 100 may include a restraint portion 220 which comprises both directional teeth 140 with an osteo-conductive surface coating such as hydroxyapatite.

The shell 100, 110 may include apertures for the placement of fasteners such as bone screws to secure the shell 100, 110 to the endplate 141 after insertion. It is preferable that the fasteners are also manufactured from a radiolucent material such as PEEK, however the surgeon may choose to use fasters made of a biocompatible metal such as from the family of titaniums or stainless steels. It is preferable that these apertures are counter bored when possible to reduce the profile of the screw head outside the periphery of the shell 100, 110. If the device is equipped with a restraint boss 200, the anterior facing surface of this boss is a preferred location for these apertures 520 wherein the apertures 520 are preferably directed towards the center of the vertebral body.

Figure 16:
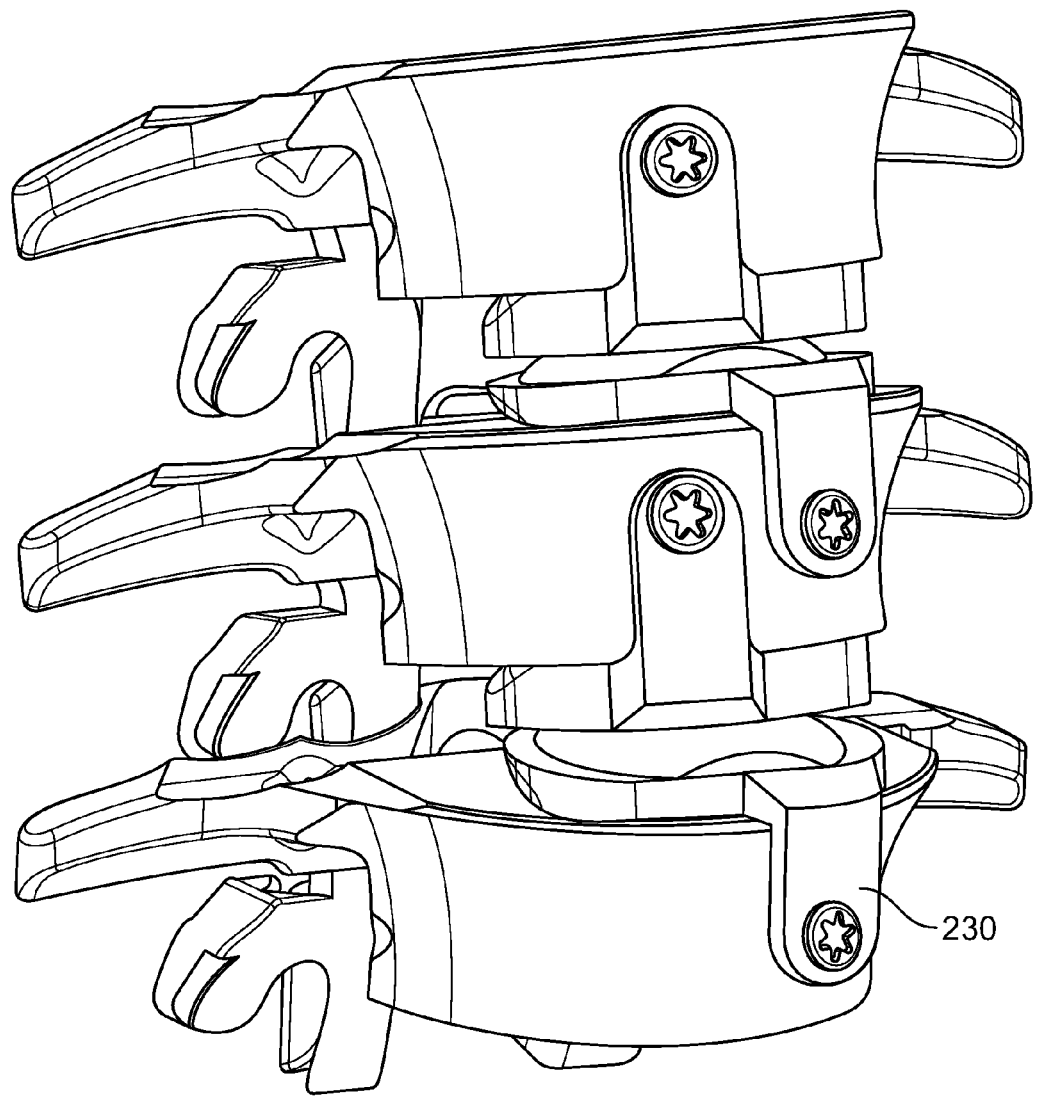
FIG. 16 is an anterolateral perspective view of two implants with securing mechanisms according to the present invention implanted within the intervertebral space.
Figure 17:
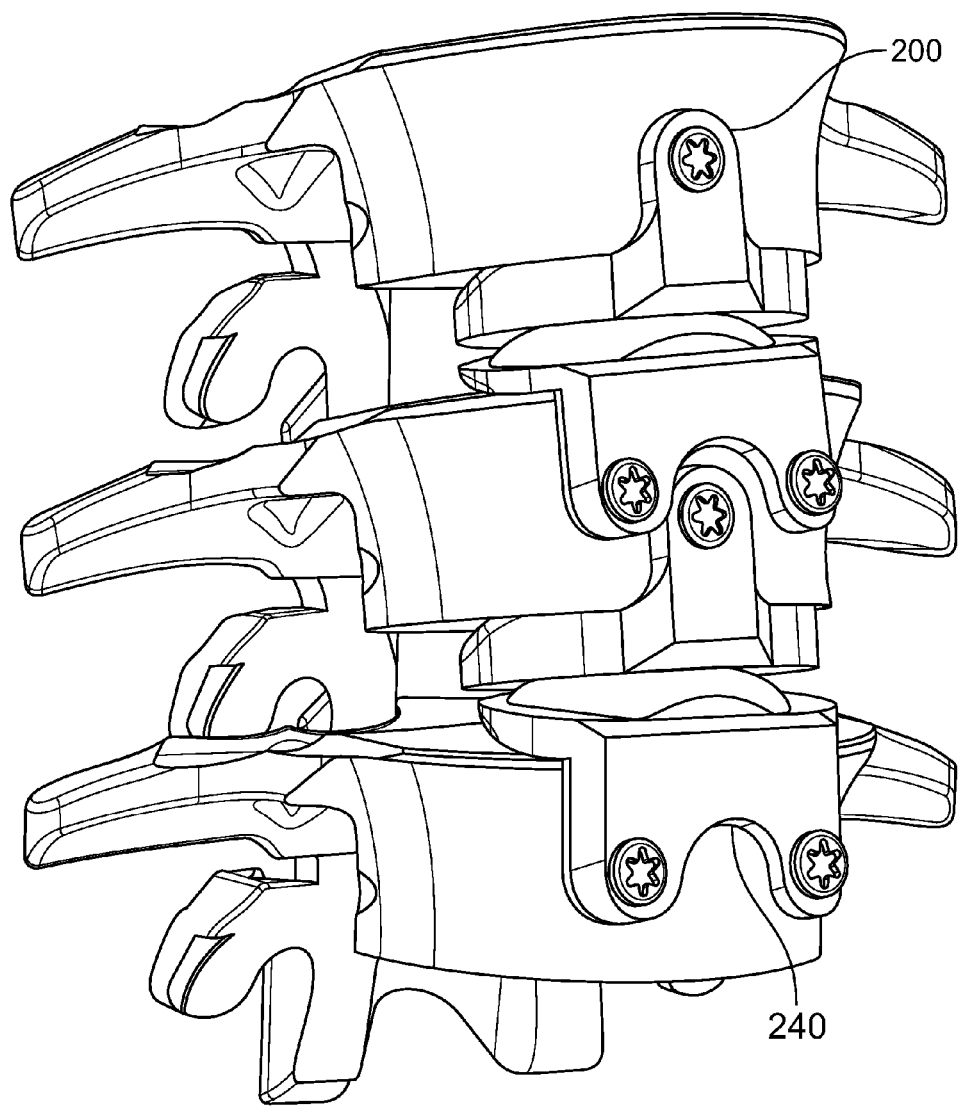
FIG. 17 is an anterolateral perspective view of two implants with securing mechanisms according to the present invention implanted within the intervertebral space.
Figure 18:
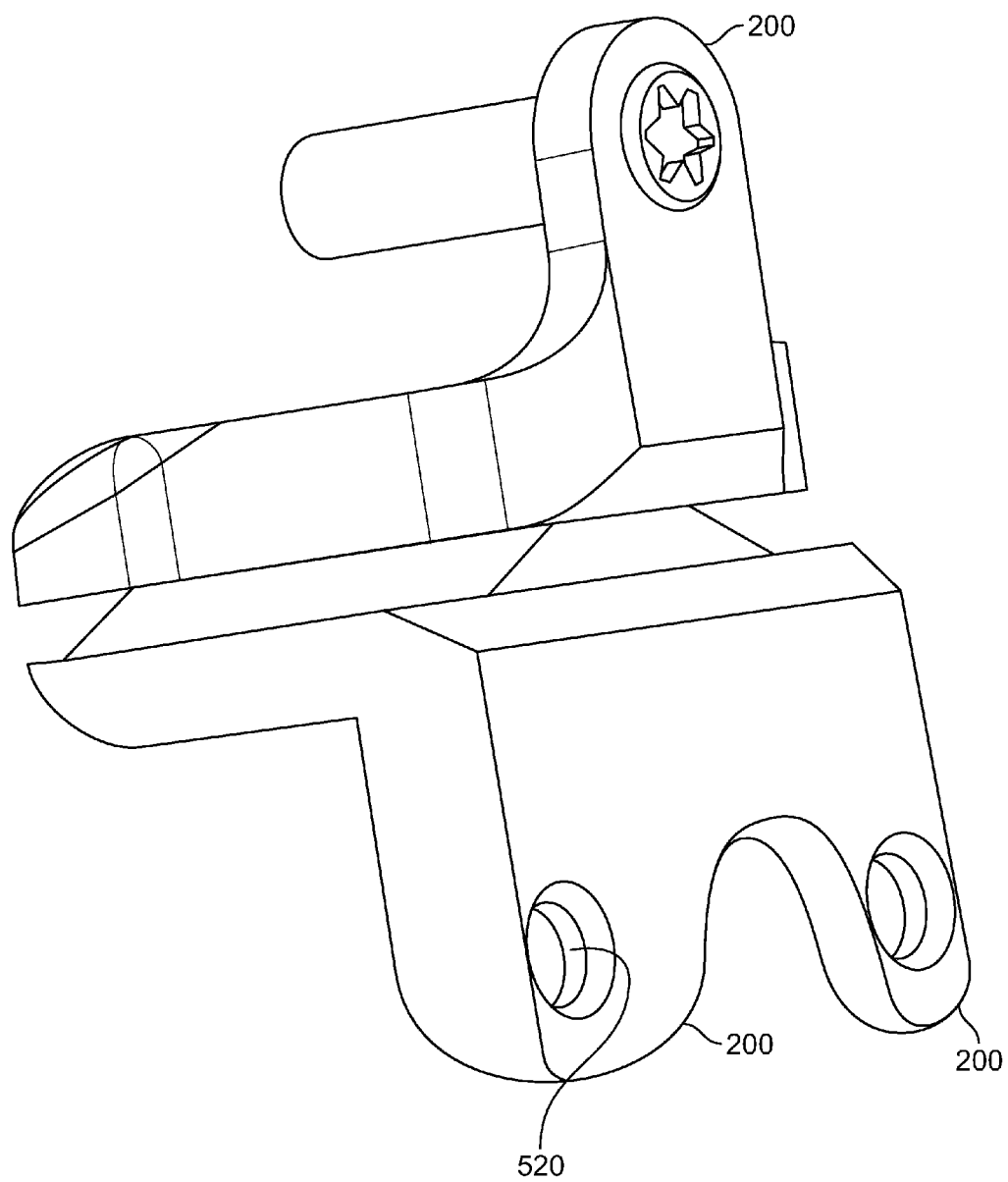
FIG. 18 is an anterolateral perspective view of the implant of FIG. 17.

In some forms, the restraint boss 200 may be offset to the left or the right as illustrated in FIG. 16. In this fashion, the artificial disc device 001 can be utilized at multiple adjacent vertebral levels without interference of an adjacent restraint boss 200. Similarly, the restraint boss 200 may be contoured to accommodate an adjacent restraint boss 200 through a boss recess 240. Again, this orientation provides utilization of the artificial disc device at multiple adjacent vertebral levels without interference of an adjacent restraint boss 200. FIG. 18 further illustrates this embodiment.

In other forms, the restraint boss 200 may not be integral to the shell 100, 110. Instead the boss 200 may be configured as a small plate, fastened to the anterior surface of the vertebral body and extending just past the endplate to block back-out of the shell 100, 110 and lateral movement of the shell 100, 110 if the boss 200 is so equipped with interlocking geometry. Further, the disc device may be blocked from backing out by a broad flexible mesh, preferably made of a polymer such as PEEK, fastened from the anterior surface of one vertebral body to the other.

Figure 8:
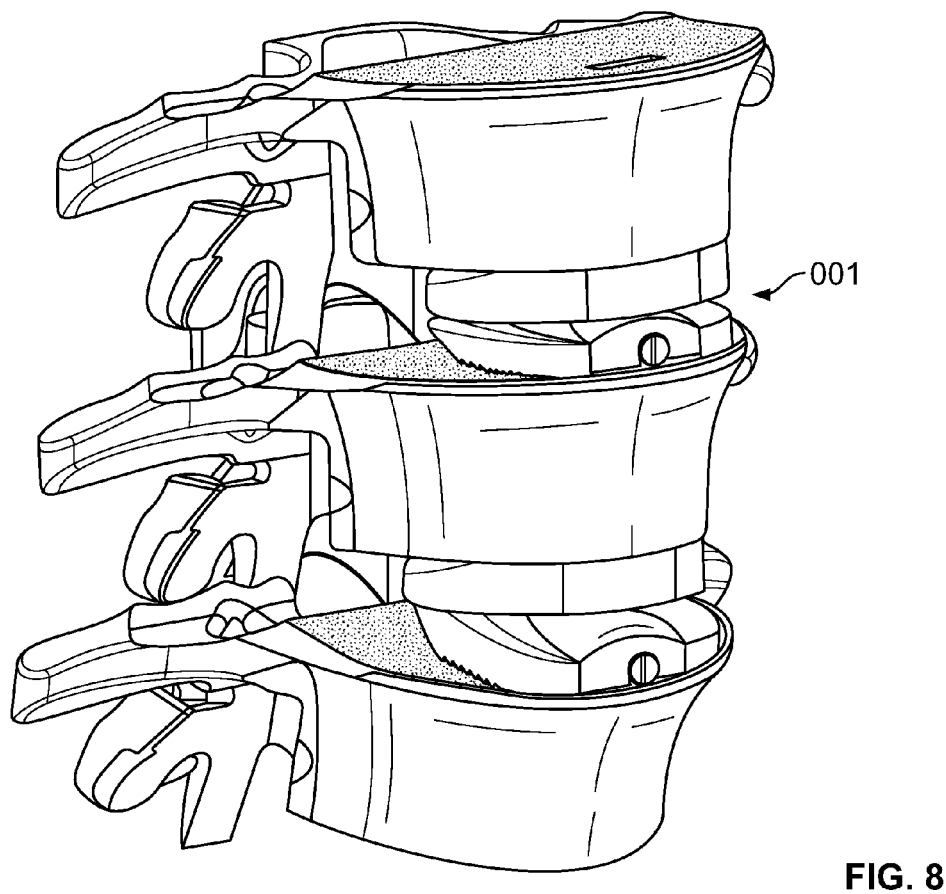
FIG. 8 is an anterolateral perspective view of an implant with a securing mechanism according to the present invention implanted within the intervertebral space.
Figure 9:
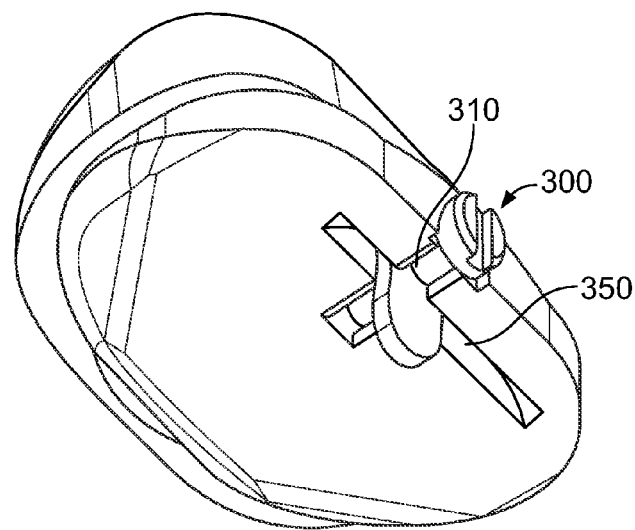
FIG. 9 is a perspective view of a bearing surface of an implant component with a securing mechanism according to the present invention.
Figure 10:
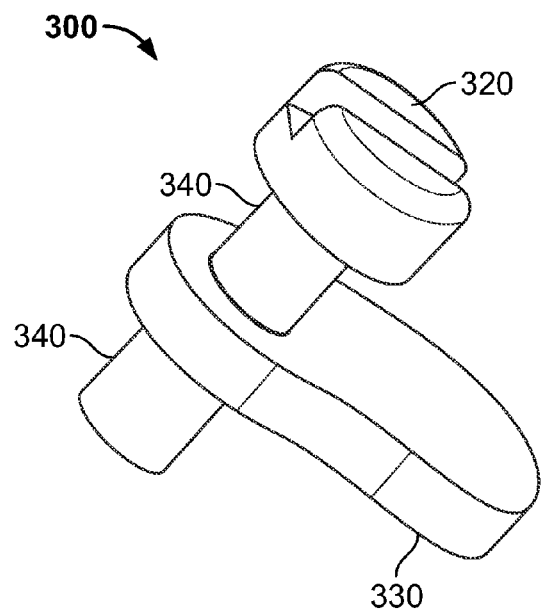
FIG. 10 is a perspective view of a securing component in the form of a deployable paddle or cam according to the present invention.
Figure 11:
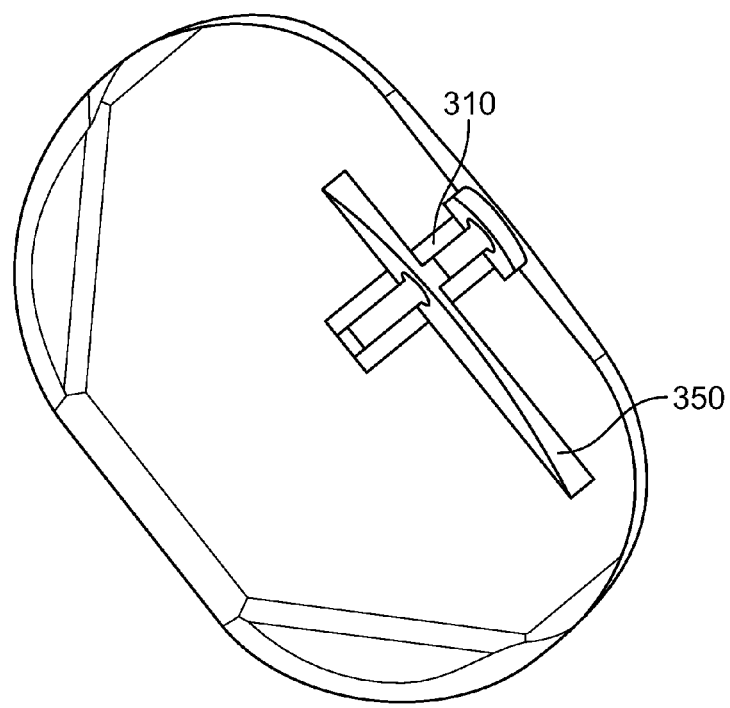
FIG. 11 is a perspective view of a bearing surface of an implant component with a deployable securing mechanism according to the present invention.
Figure 12:
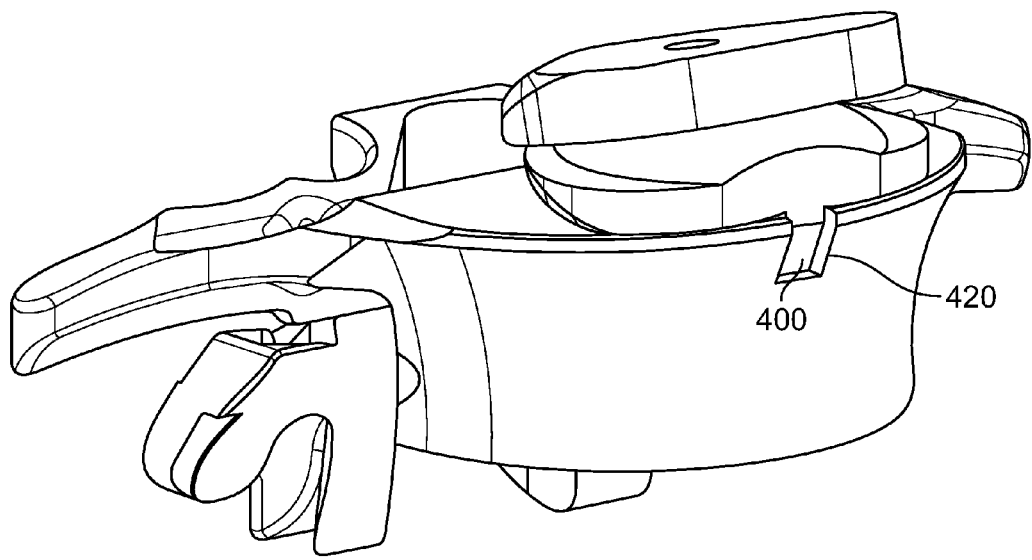
FIG. 12 is an anterolateral perspective view of an implant with a securing mechanism according to the present invention implanted within the intervertebral space.

In an alternative embodiment, the artificial disc device 001 shown in FIG. 8 comprises a restraint portion 220 in the form of a deployable paddle 300. The paddle 300 is housed within one of the shell members 100, 110 as illustrated in FIG. 9. The paddle 300 may be manufactured from an array of biocompatible materials including but not limited to polymers such as PEEK or metals such as titanium or stainless steel alloys although radiolucent materials are preferred. In a preferred orientation, the paddle 300 is secured within the body of a shell 100, 110 by a paddle restraint 310 in this case in the form of a snap joint. The paddle comprises a restraint arm 330 that may be deployed into the endplate 141 of the vertebrae 143 upon rotation of the drive head 320 with the proper instrument. The restraint arm 330 may include a sharpened edge if so desired. The neck portion 340 of the paddle 300 is held by the paddle restraint 310 and is preferably configured with a profile suitable for rotation. The restraint arm 330 may include apertures or slots to encourage bone growth through the restraint arm 330.

The endplate facing surface 142 comprises a restraint recess 350 to accommodate the paddle 300 and the restraint arm 330 during implant insertion. Once the disc device 001 is inserted, the restraint arm 330 may be deployed into the endplate to secure the device 001 in the desired location between the vertebrae. Several of the disclosed embodiments may require the surgeon to prepare the vertebral body 144 to accept restraint portions 220 that are intended to become integrated into the bone. In most cases, this preparation involves removing bone and creating restraint access 420 typically in the form of a recess, channel, slot or profile similar to the restraint feature. Obviously, the size of the restraint portion 220 will affect the size of the restraint access 420. Therefore it is beneficial that restraint portions 220 that interfere with the bone are suitably sized to prevent an oversized restraint access 420 that compromises the vertebrae 143 and risks vertebrae 143 fracture. It is preferable that both the restraint access 420 and restraint portion 220 have radiused edges to reduce stress concentrations in the vertebral body.

Figure 13:
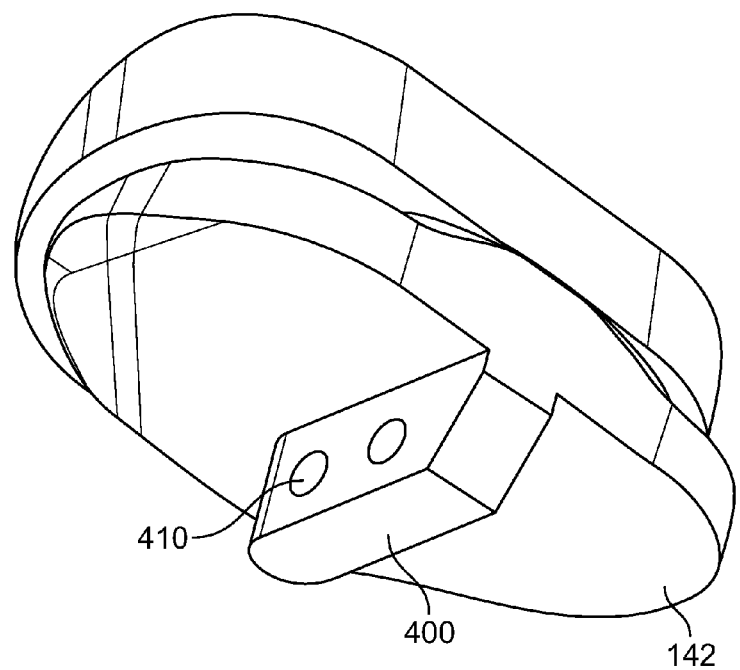
FIG. 13 is a perspective view of an implant with a securing mechanism according to the present invention.
Figure 13A:
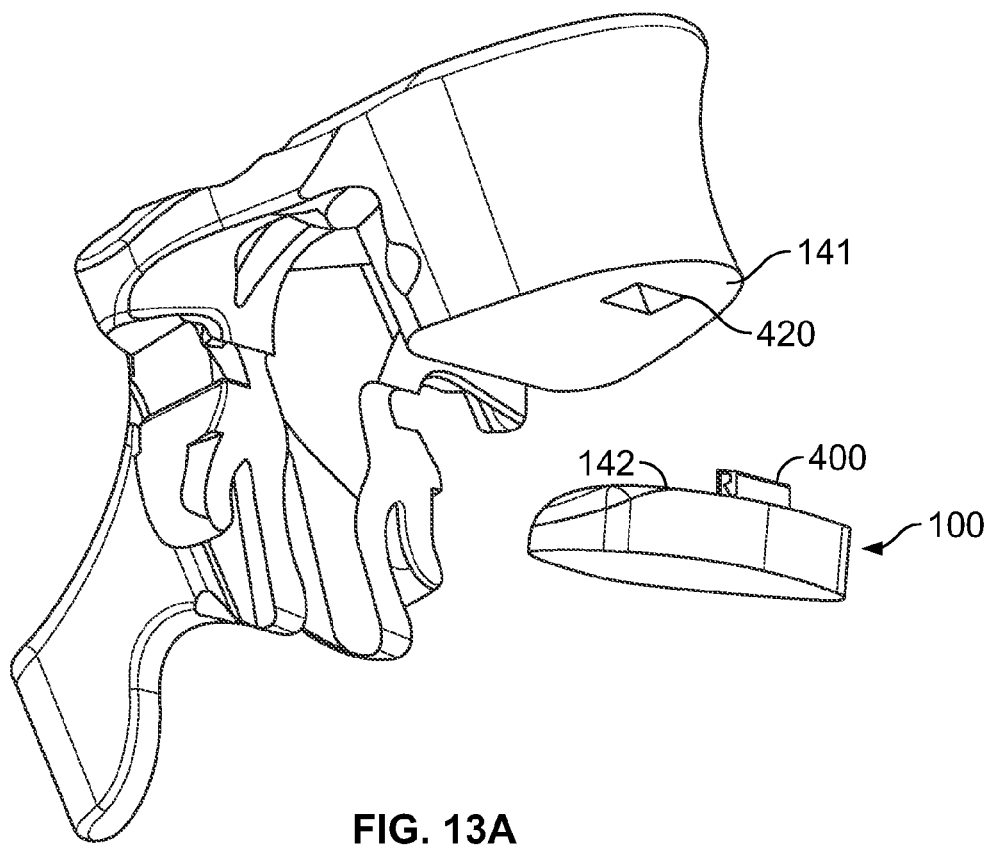
FIG. 13A is a perspective view of an implant component with a securing mechanism according to the present invention shown adjacent a vertebrae.
Figure 15:
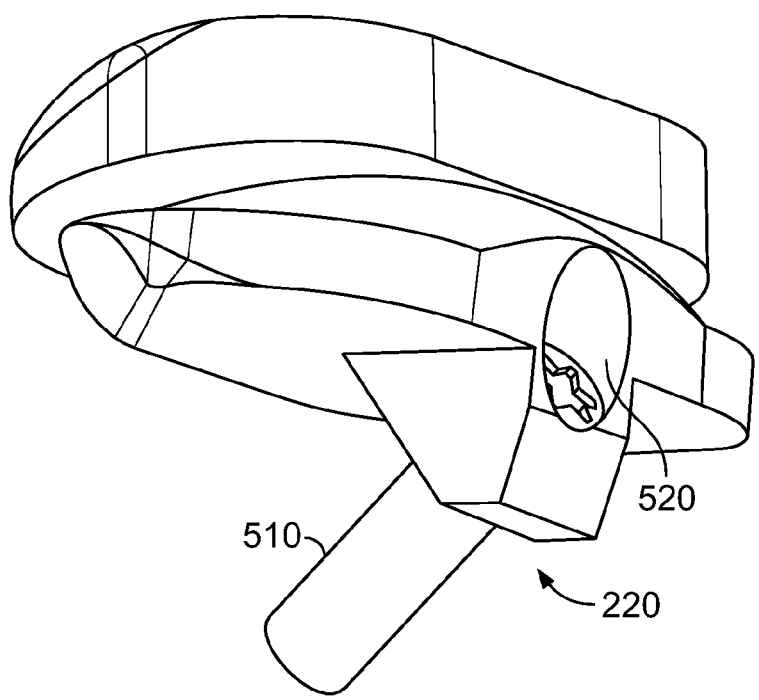
FIG. 15 is an anterolateral perspective view of an implant with a securing mechanism according to the present invention.

In another alternative embodiment, such as shown in FIG. 13, an artificial disc device 001 comprises a restraint portion 220 in the form of an integrated fin 400 extending from the endplate facing surface 142. The fin 400 may vary in thickness and length as needed to assist in restraining the artificial disc device 001 in a predetermined intervertebral position. The fin 400 may include bone growth apertures 410, slots, or other structure to facilitate bone growth through the fin and thereby provide additional restraint to the device. Again, the restraint portion 220 may be found on one or both of the shells 100, 110. Alternatively, although the implant is typically inserted from an anterior to posterior approach, the fin 400 may not necessarily be oriented in this same direction. For example, the fin 400 in FIG. 13A illustrates a fin 400 that extends laterally across the endplate facing surface 142. In this embodiment, a restraint access 420 is also cut laterally across the endplate 141. There is no entry into the restraint access 420 from the peripheral edge of the vertebral body. Therefore, the surgeon may choose to first distract or over stretch the intervertebral space, making room for the addition height of the fin 400 until the fin 400 can fall into the restraint access 420 to secure the implant in the predetermined position. The fin 400 may be equipped with a ramped lead-in wherein the lead-in can be utilized to help distract the vertebrae.

Figure 14:
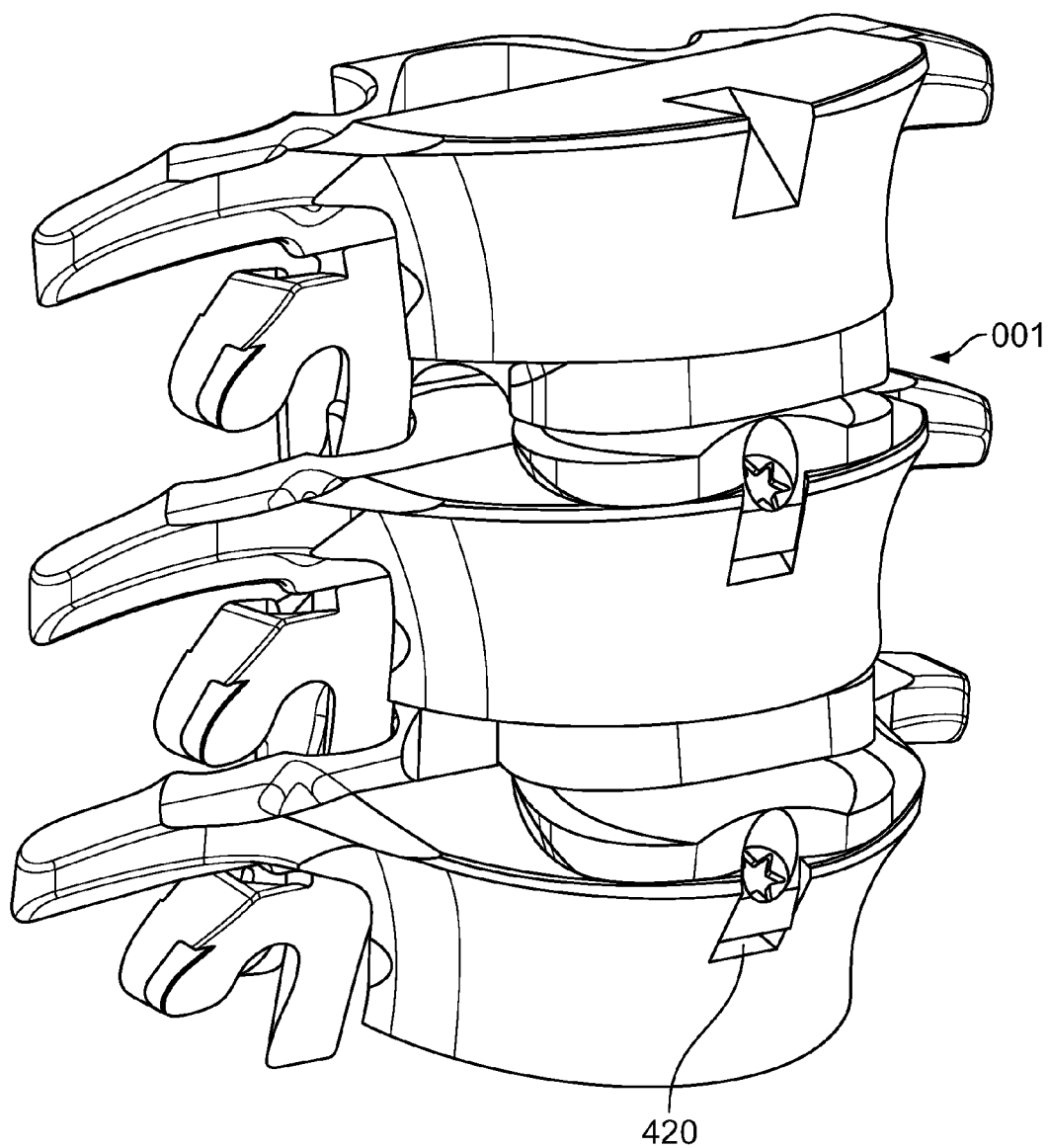
FIG. 14 is an anterolateral perspective view of two implants with a securing mechanism according to the present invention implanted within the intervertebral space.

In an alternative embodiment, the artificial disc device 001 as illustrated in FIG. 14 may comprise a restraint portion 220 in the form of a fin 400 which accommodates a bone fastener 510 therein. It is preferable that the bone fastener 510 is in the form of a bone screw and is manufactured from a radiolucent material such as PEEK, however the surgeon may choose to use bone fasteners 510 made of a biocompatible metal such as from the family of titaniums or stainless steels. It is preferable that the fastener aperture 520 is counter bored when possible to reduce the profile of the screw head outside the periphery of the shell 100, 110. The fastener aperture 520 may include fastener restraint such as an interference spring to prevent fastener 510 back-out. For example, the fastener aperture 520 may have a groove inscribed therein to house a spring that expands out of the way of the fastener 510 while driving the fastener and closes over the head of the fastener once the head passes the spring.

Figure 19:
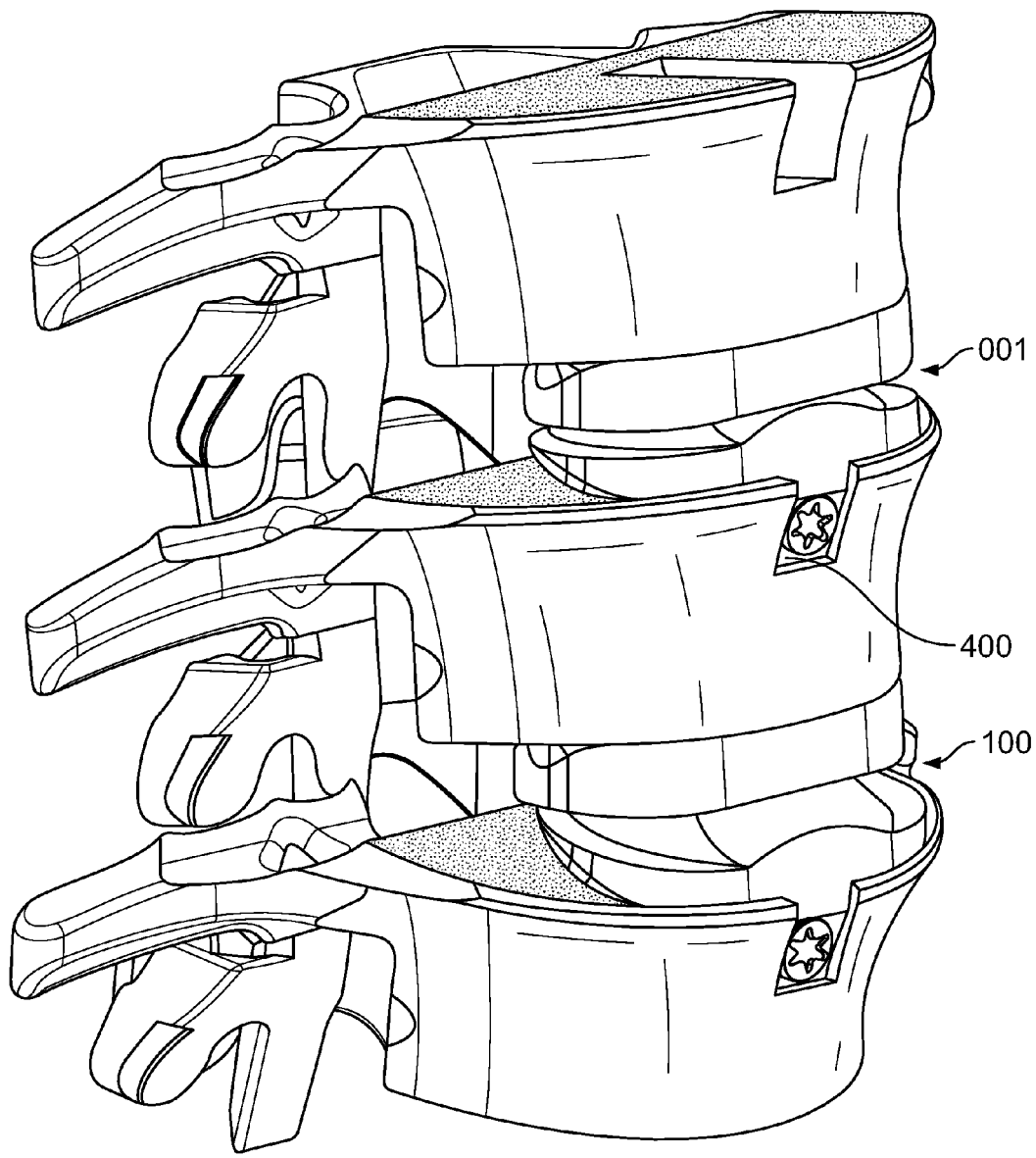
FIG. 19 is an anterolateral perspective view of two implants with securing mechanisms according to the present invention implanted within the intervertebral space.
Figures 20, 21:
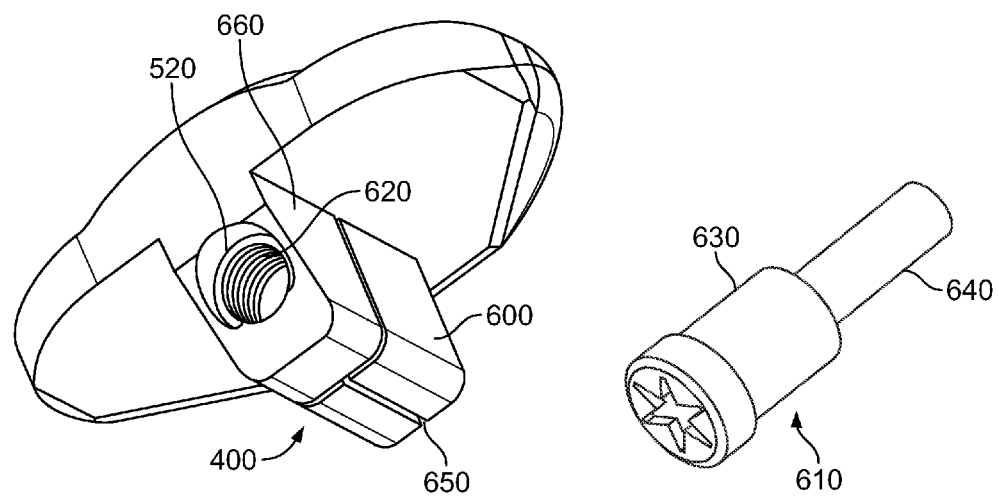
FIG. 20 is a perspective view of the lower implant member of FIG. 19.
FIG. 21 is a perspective view of a fastener implemented in the securing mechanism of FIG. 20.

An additional alternative embodiment of the artificial disc device 001 is illustrated in FIGS. 19-21 and comprises a restraint portion 220 in the form of a fin 400 wherein the fin 400 comprises one or more deflectable wall portions 600. The fin 400 again comprises a fastener aperture 520 to house an expansion fastener 610. In the preferred form, the expansion fastener 610 comprises a threaded shaft 630, to drive the fastener 610 down the aperture 520 when rotated, and an expansion shaft 640 to drive apart the deflectable wall portions 600 as the fastener 610 is driven forward. The aperture 520 in this configuration preferably comprises threads 620 to complement the threaded shaft 630. As the expansion fastener 610 is driven and causes the wall portion 600 to deflect outward a predetermined amount, these wall portions 600 will interfere within the restraint access 420 securely holding the disc device 001 in position. Deflection cuts 650 facilitate the deflection of the wall portion 600 with respect to the fastener block 660. The deflection cuts 650 may be orientated in different directions wherein, for example, the wall portion may deflect laterally along a vertical plane or laterally along a horizontal plane. Since the disc device 001 will typically be inserted from a generally anterior surgical approach, it is preferred that the fin 400 also be orientated generally anterior to posterior.

Figure 22:
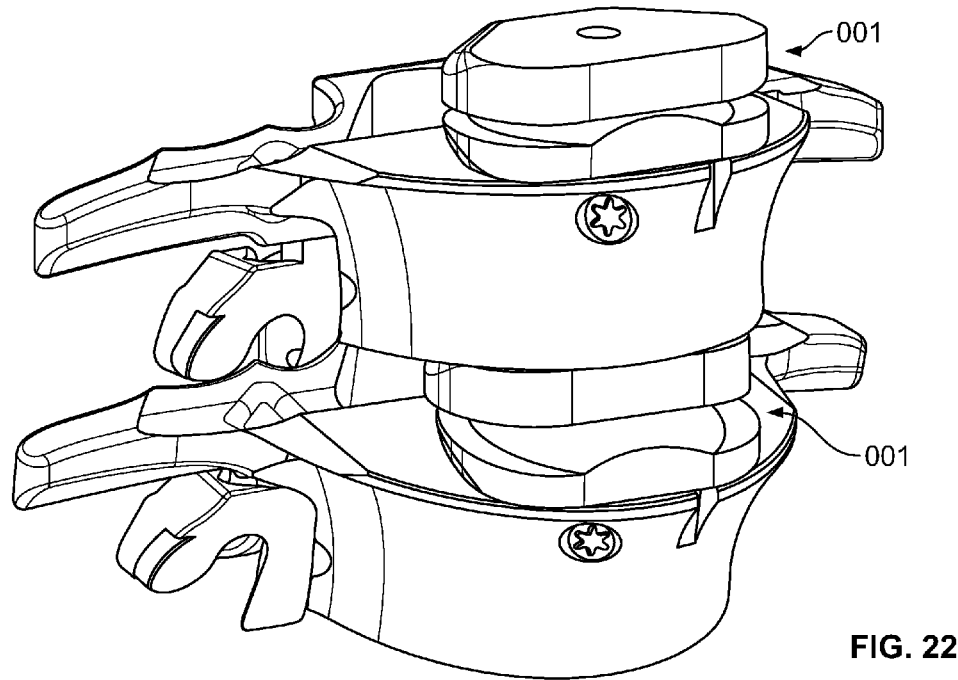
FIG. 22 is an anterolateral perspective view of two implants with securing mechanisms according to the present invention implanted within the intervertebral space.
Figure 23:
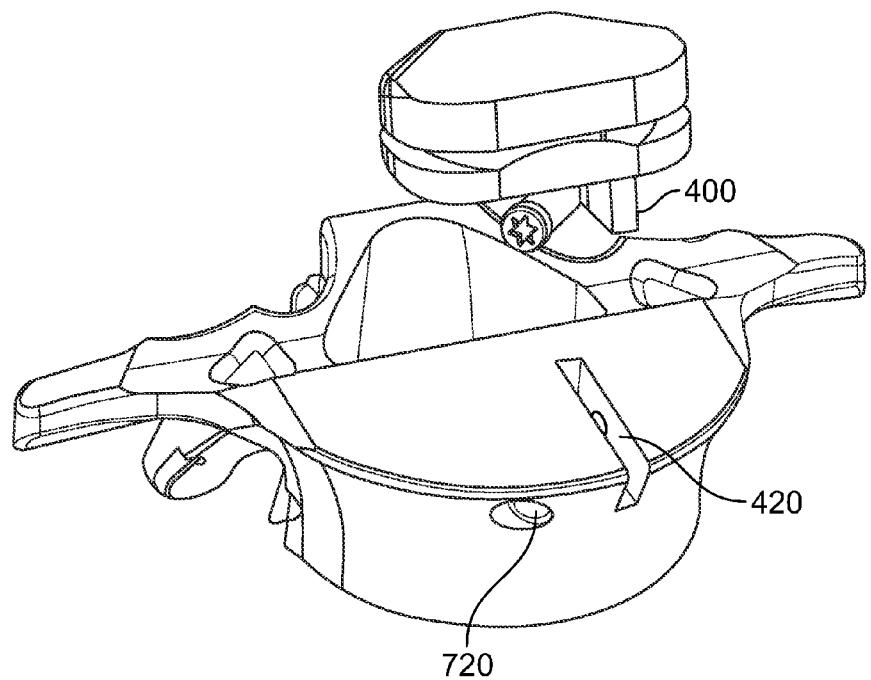
FIG. 23 is an anterolateral perspective view of the implant of FIG. 22 adjacent a vertebrae having a groove and angled bore formed therein for engaging with the securing mechanism.
Figure 24:
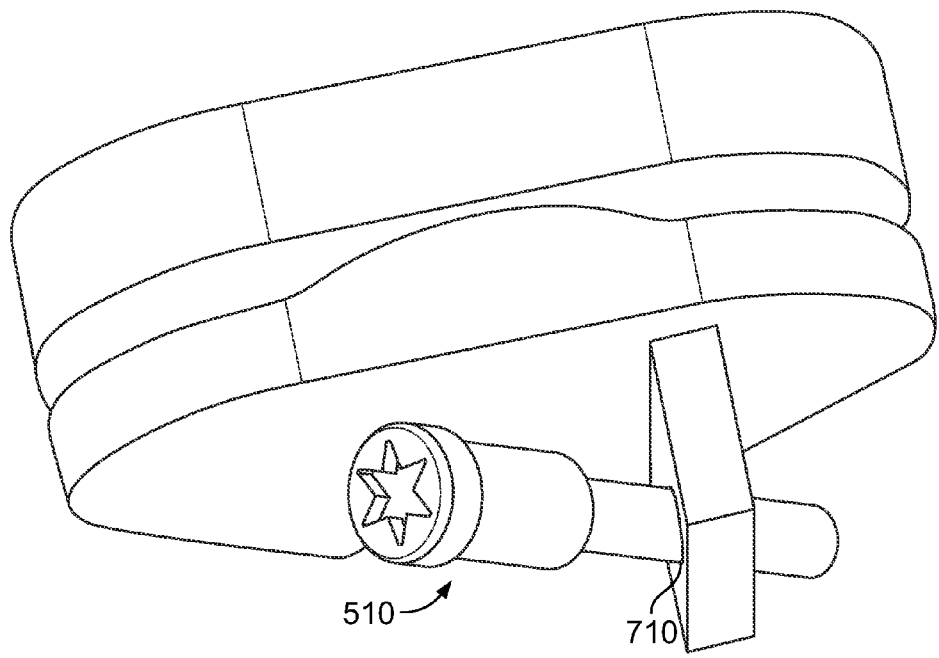
FIG. 24 is a perspective view of the implant of FIG. 22.

Another embodiment of an artificial disc device 001 is illustrated in FIGS. 22-24 and comprises a restraint portion 220 in the form of a fin 400. The fin 400 in this embodiment is preferably laterally offset to one side or the other. The fin 400 preferably comprises an interference portion 710, typically in the form of a threaded or unthreaded hole or recess. After the shell 100, 110 having this feature is inserted into the predetermined position, an alignment instrument (not shown), comprising a drill guide orientated to the implant may be utilized to create a pilot hole 720 through the vertebrae that is directed at the interference portion 710. A bone fastener 510, preferably in the form of a bone screw, is then driven into the pilot hole 720, and in interfering relation with the interference portion 710, secures the disc device 001 in a predetermined position. The fastener 510 in this embodiment is preferably threaded where it contacts the bone, and may interfere with the fin 400 by threading through it, extending through it, abutting it, or any other interference method. In embodiments wherein a fastener 510 is threaded or otherwise engaged into a deformable implant material, (i.e. an implant manufactured from PEEK), the material itself may serve as adequate protection against fastener 510 back-out.

Figure 25:
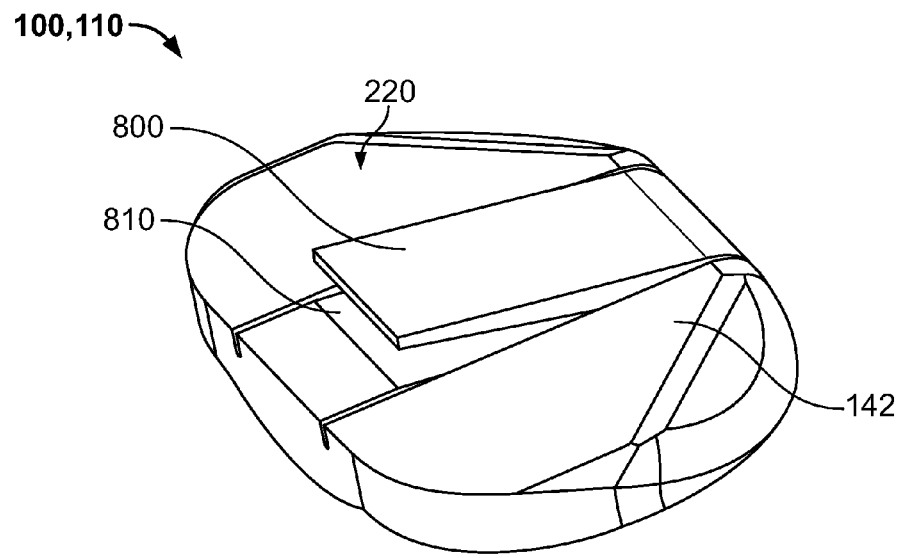
FIG. 25 is an anterolateral perspective view of an implant member with a deflectable stop according to the present invention.
Figure 26:
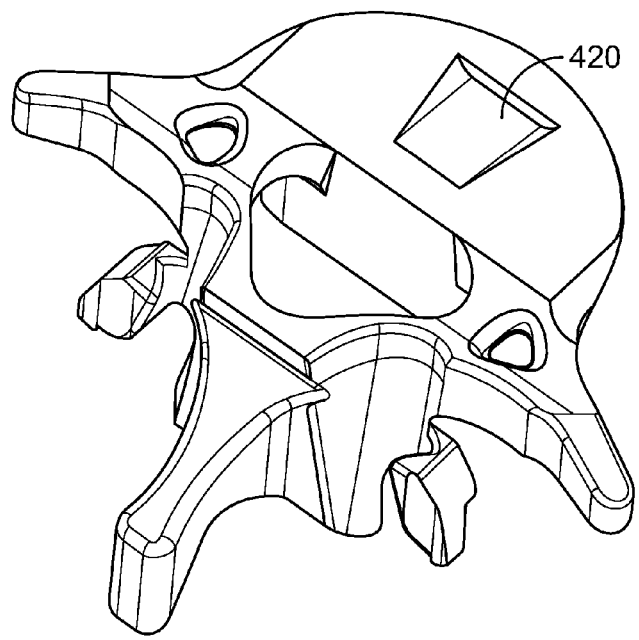
FIG. 26 is a posterolateral perspective view of a vertebrae with a formed recess for engaging with the deflectable stop of FIG. 25.

In an alternative embodiment, a shell 100, 110 is illustrated in FIG. 25 comprising a restraint portion 220 in the form of a deflectable stop 800. The deflectable stop 800 is preferably integrated into the endplate facing surface 142 adjacent the posterior end of the shell 100, 110. In the undeflected orientation and from this point of integration, the deflectable stop 800 gradually extends anterior and away from the endplate facing surface 142. As the shell 100, 110 is inserted between the vertebrae, the deflectable stop 800 may deflect into the stop recess 810 as the shell passes over the complementary profiled restraint access 420 created by the surgeon as illustrated in FIG. 26. Once the shell 100, 110 is positioned in its predetermined location, the deflectable stop 800, and the restraint access 420 are aligned such that the stop 800 will spring back into the restraint access 420 securely retaining the shell 100, 110 in position.

Figure 27:
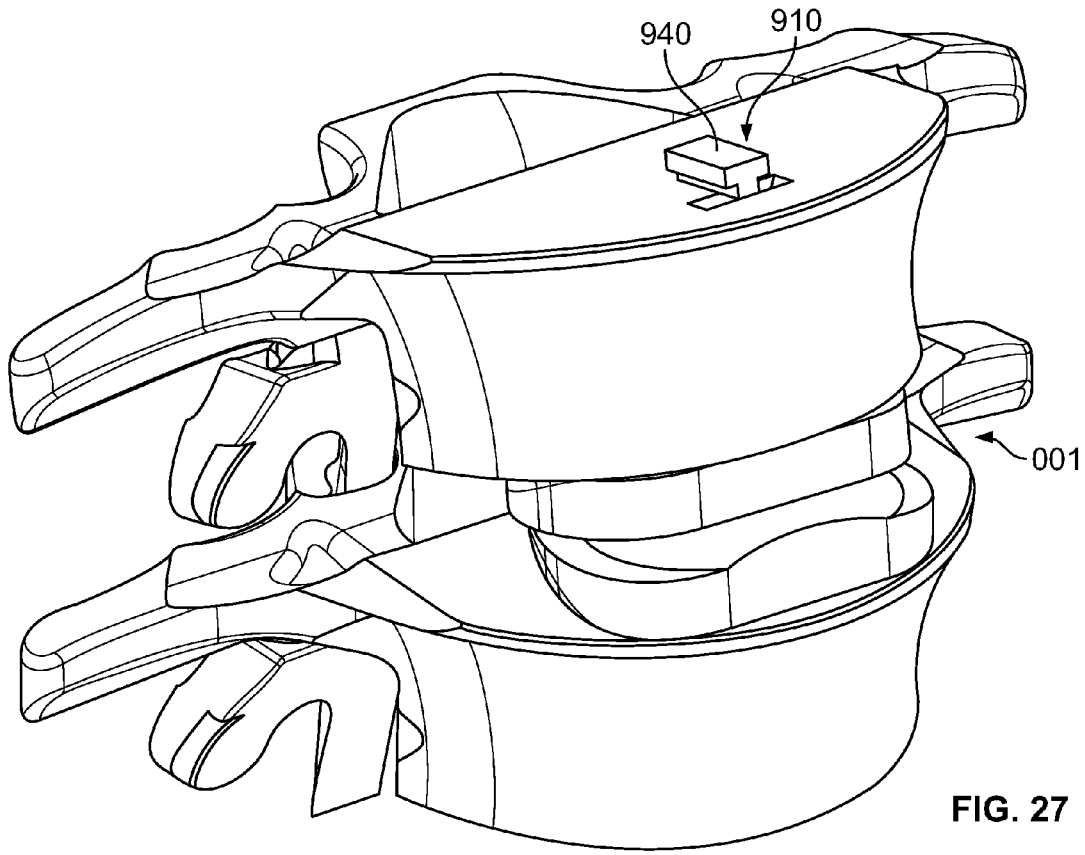
FIG. 27 is an anterolateral perspective view of an implant with a securing mechanism according to the present invention implanted within the intervertebral space.
Figure 28:
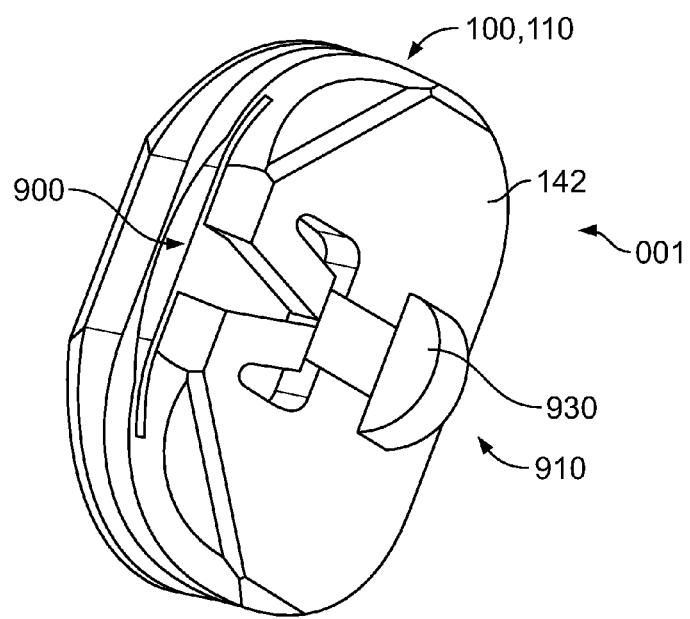
FIG. 28 is a perspective view of the implant of FIG. 27.
Figure 29:
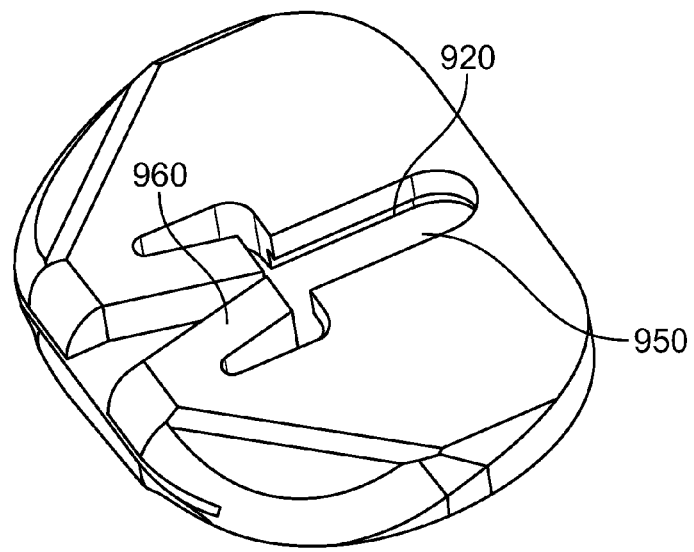
FIG. 29 is a perspective view of an implant member of the implant of FIG. 27.
Figure 30:
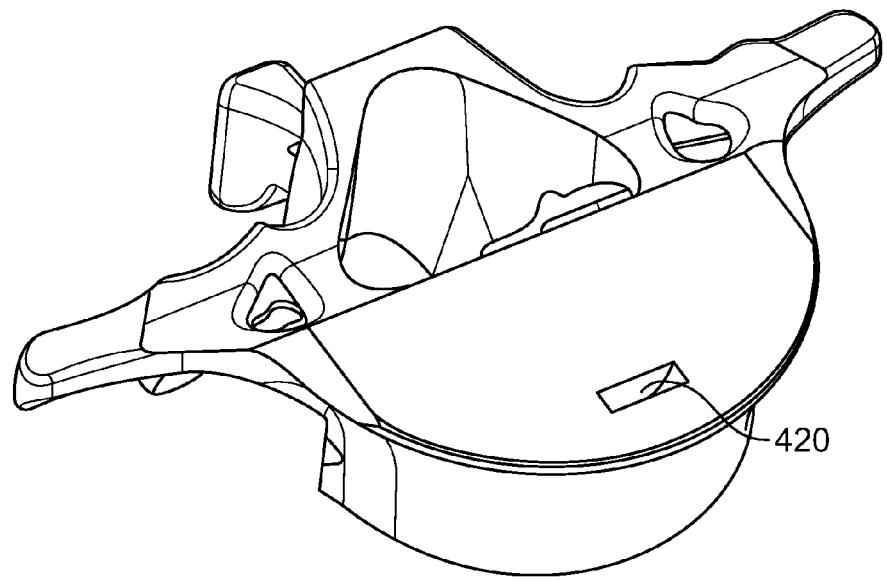
FIG. 30 is an anterolateral perspective view of a vertebra with a formed recess for interacting with a securing mechanism.

Similarly, and in a further alternative embodiment, an artificial disc device 001 is illustrated primarily in FIGS. 27-29 comprising a restraint portion in the form of a deflectable capture 900 preferably integrated into the endplate facing surface 142 adjacent the posterior end of the shell 100, 110. An interlock key 910, comprising a bone boss 930 and a connection pod 940 with interlock structure complementary to the interlock key 910, is situated in a preformed restraint access 420 such as shown in FIG. 30. As the shell 100, 110 is inserted across the vertebral endplate 141, the deflection arms 960 are pushed open by the connection pod 940 until the pod 940 is seated in the pod canal 950 and the deflection arms 960 are able to spring back into a pod 940 locking position. The pod canal 950 may include complementary structure, such as a tongue and groove arrangement 920, to secure the pod 940 to the shell 100, 110.

Figure 31:
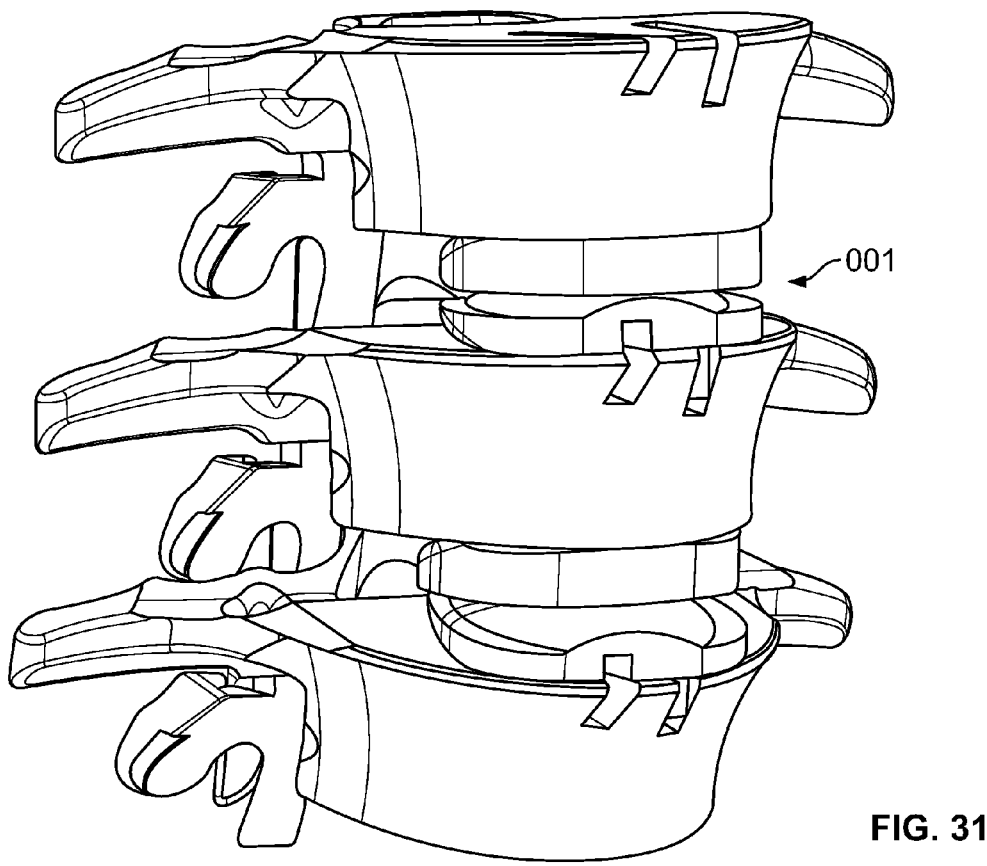
FIG. 31 is an anterolateral perspective view of two implants with securing mechanisms according to the present invention implanted within the intervertebral space.
Figure 32:
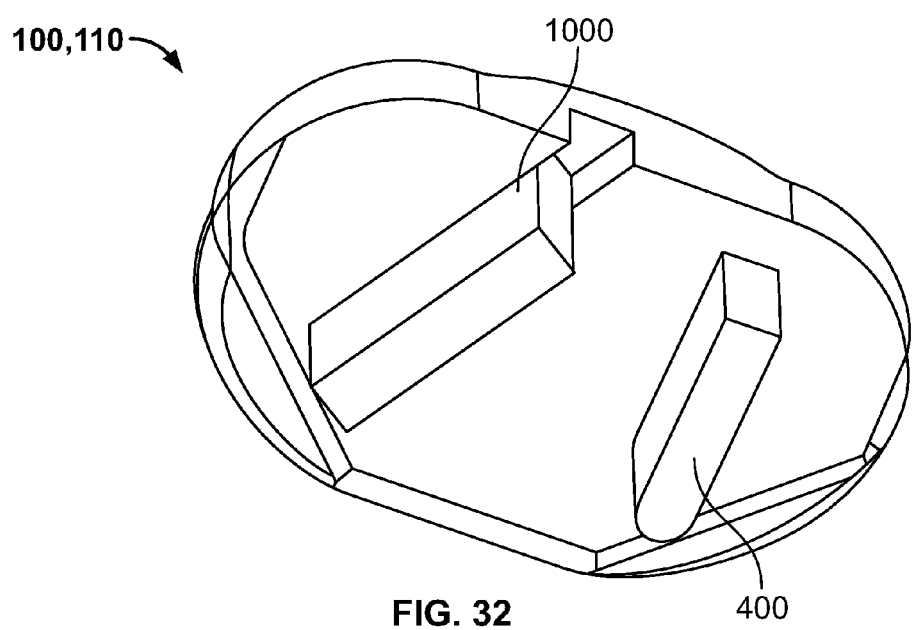
FIG. 32 is a perspective view of a bearing surface of the lower implant member of the implant of FIG. 31.
Figure 33:
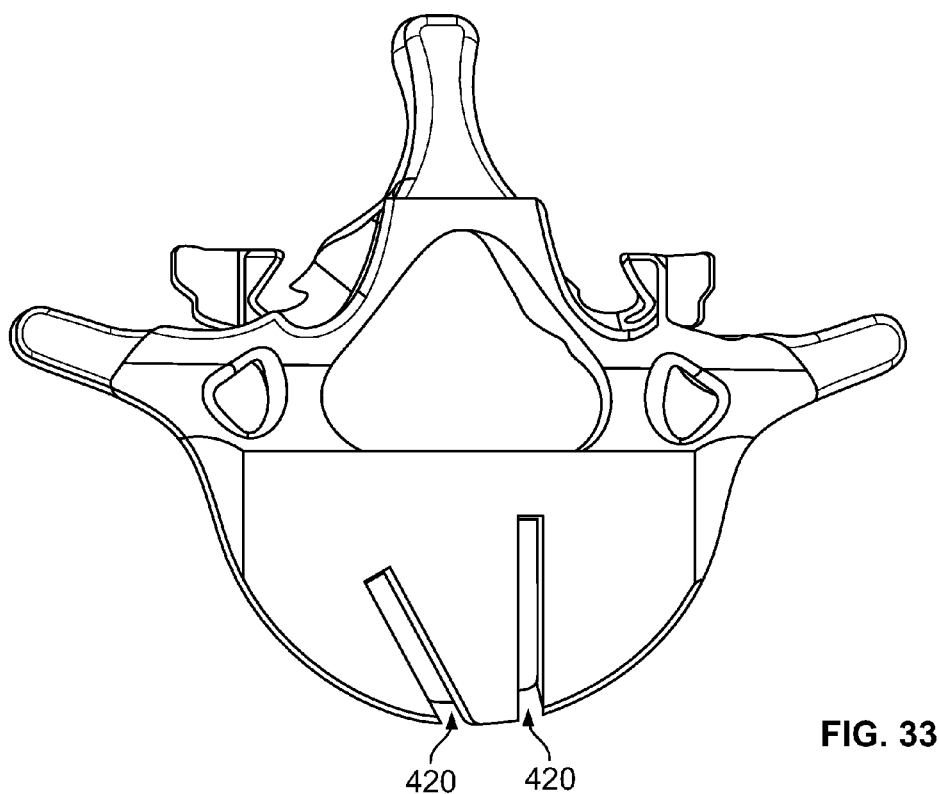
FIG. 33 is a top view of a vertebra end plate with grooves formed therein for mating with the securing mechanism of the implant of FIG. 31.
Figure 34:
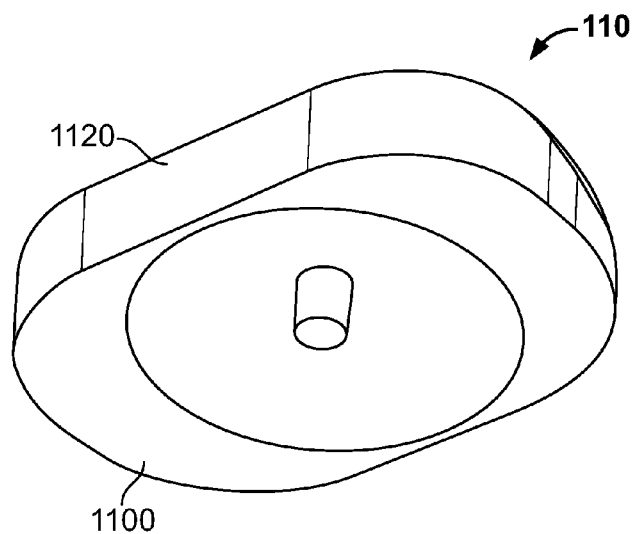
FIG. 34 is a perspective view of an implant component according to the present invention with a motion limiting component disposed on the articulating surface.
Figure 35:
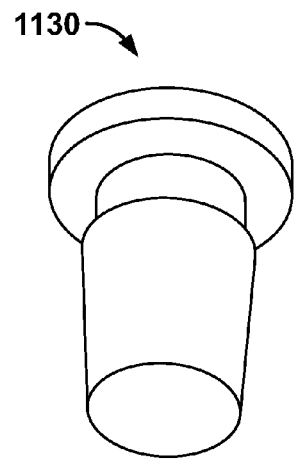
FIG. 35 is a perspective view of the motion limiting component of FIG. 34.

Another alternative embodiment is illustrated in FIG. 31 wherein an artificial disc device 001 comprises a restraint portion 220 in the form of a fixed fin 400, and an insertable locking fin 1000. Restraint access 420 is formed in the vertebral endplate 141 complementing the position of the fixed fin 400 and the locking fin 1000 on the shell 100, 110 as illustrated in FIG. 33. The shell 100, 110 is inserted, with the locking fin 1000 removed, to its predetermined position between the intervertebral endplates. The locking fin 1000 preferably comprises a friction fit interlocking architecture such as tongue and groove with the shell 100, 110 to secure the locking fin to the shell 100, 110 and restrict back-out. The locking fin 1000 and the fixed fin 400 are orientated non-parallel to each other such that once the locking fin 1000 is inserted, the corresponding shell is restrained to the desired position on the endplate 141.

The artificial disc device 001 can take a form of a non-constrained articulating joint wherein the device 001 has no built in features to limit motion between the articulation surfaces 121 and 131. In some cases, this can be problematic if the anatomy of the user, by hard or soft tissue, does not perform this function since it is possible that a shell 100, 110 can dislocate off the other shell 100, 110 and potentially become jammed. In addition, excessive unnatural motion at the device 001 may cause injury to the user. For these reasons it may be advantageous to limit the motion occurring between the articulation surfaces 121 and 131.

Figure 36:
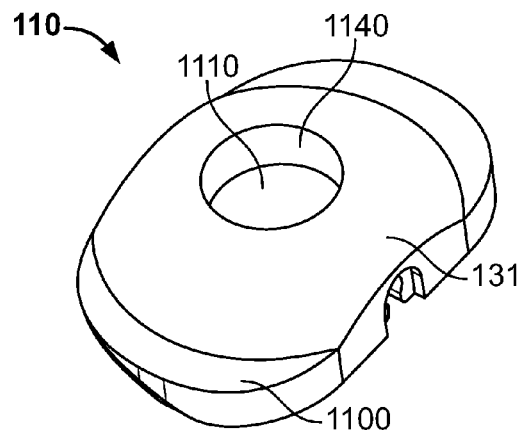
FIG. 36 is a perspective view of a corresponding implant component of the implant component of FIG. 34 with a motion limiting recess.

The artificial disc device may include a motion-limiting portion. In the shell 110 embodiment shown in FIG. 36, this motion-limiting portion is in the form of a motion-limiting stop 1100 that is a protruding surface discontinuous with the curvature of the convex articulating surface 131. Alternately, the stop may instead be formed on the shell 100, or on both shells 100, 110. As one shell articulates against the other, the stop will limit the freedom of motion that can occur.

The motion limit portion may take numerous forms. For example, one of the shells 100, 110 may comprise a limiter holder 1120 to house a limit post 1130. Alternatively the limit post 1130 may be integrated into the articulating surface of the shell 100, 110. The limit post 1130 extends into a limit recess 1110 preferably bound by a limit wall 1140. As the shells 100, 110 articulate against each other, interference between the limit post 1130 and the limit wall 1140 limit the motion that can occur between the shells 100 and 110. Clearly, by adjusting the shape and/or size of the limit recess 1110, motion can be limited in varying amounts in different directions. For example, motion can be limited to 10 degrees of flexion but only 5 degrees of lateral bending at the joint.

Figure 37:
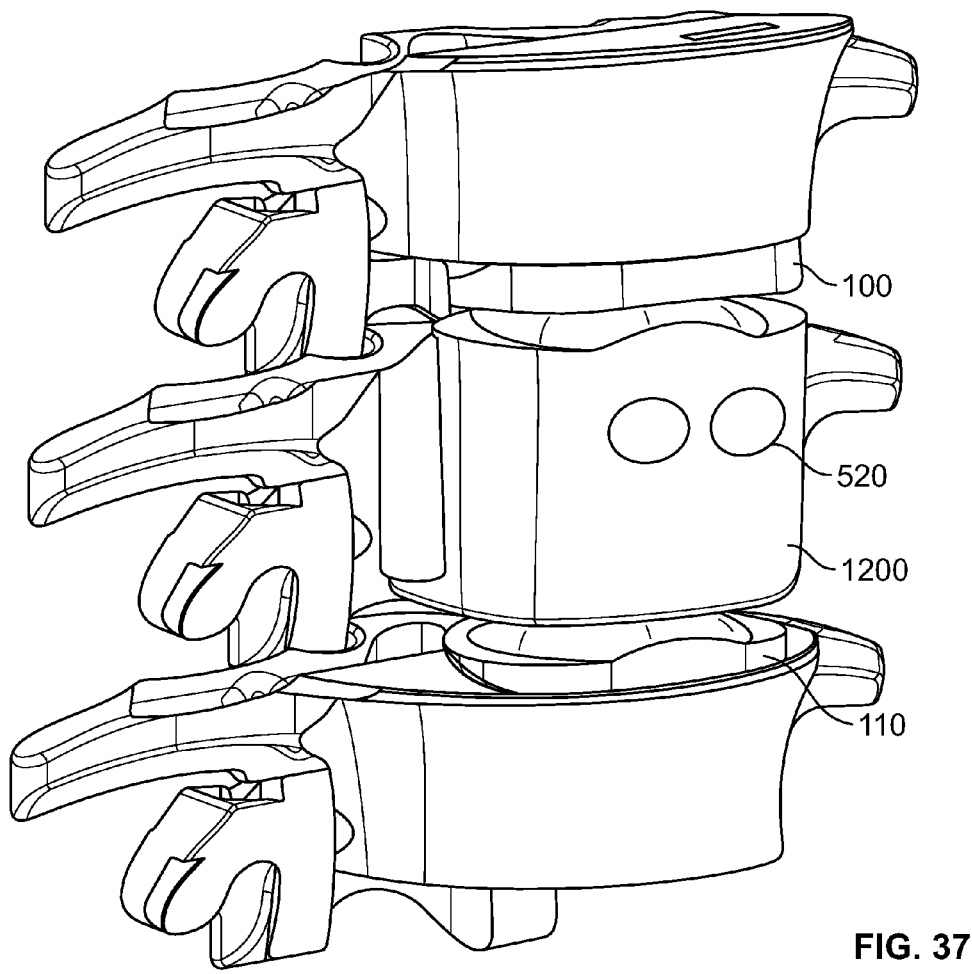
FIG. 37 is an anterolateral perspective view of a strut implant according to the present invention implanted within spine.
Figure 38:
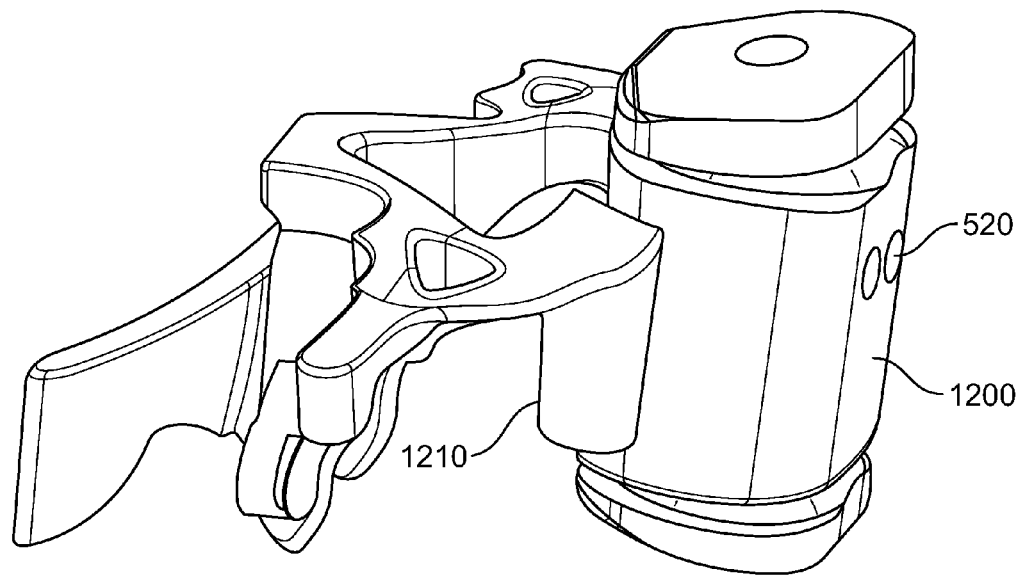
FIG. 38 is a lateral perspective view of the implant of FIG. 37.
Figure 39:
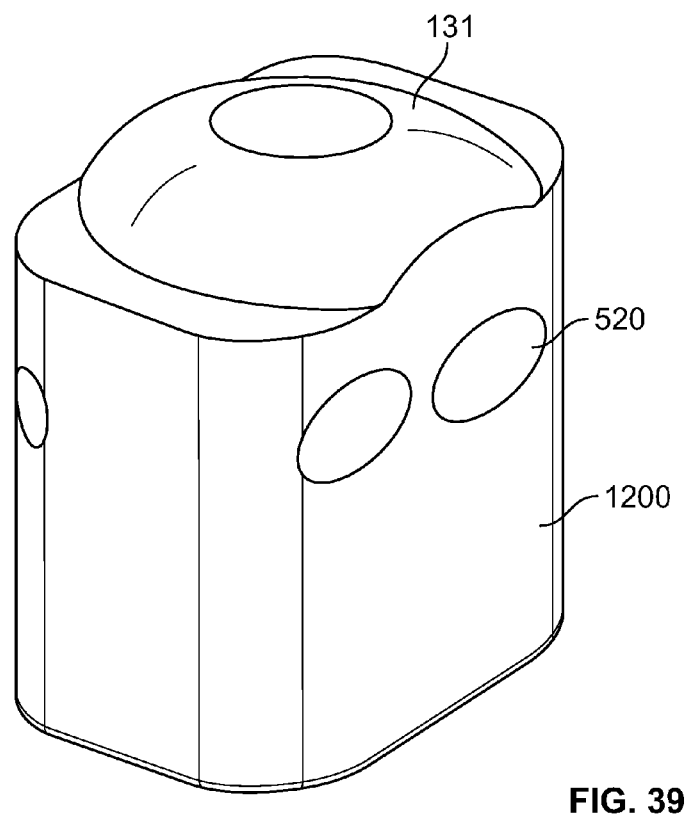
FIG. 39 is an anterolateral perspective view of an implant member of the implant of FIG. 37.
Figure 40:
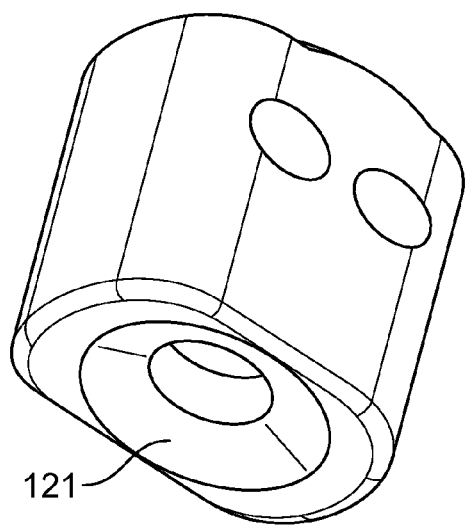
FIG. 40 is bottom perspective view of the implant member of FIG. 39.

The artificial disc device 001 may be configured for use when all or a portion of the vertebral body 144 is removed such as in a corpectomy surgery. As seen in FIGS. 37 and 38, the majority of a vertebral body 144 is removed and replaced with a vertebral strut 1200. The strut 1200 comprises any combination of convex articulation surfaces 131 and/or concave articulation surfaces 121. In addition, the body of the strut 1200 preferably comprises fastener apertures 520 to house bone fasteners 510 (not shown) secured into the remaining bone 1210 of the vertebrae 143 securing the vertebral strut 1200 in the predetermined position. Complementary shells 100, 110 articulate with the vertebral strut 1200. The vertebral strut may also comprise apertures for boney ingrowth or other osteo-conductive coatings or surfaces.

Figure 41:
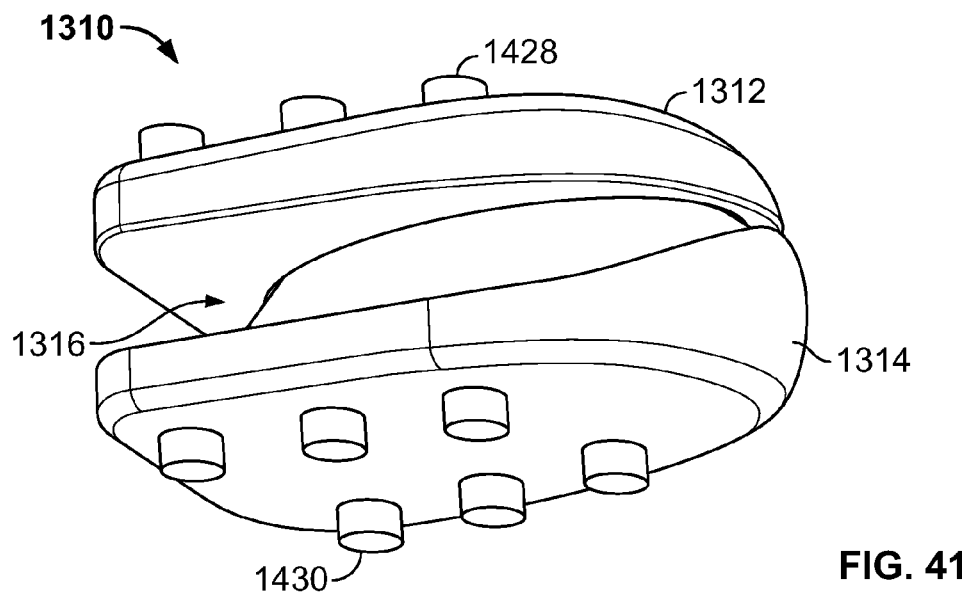
FIG. 41 is a posterolateral perspective view of an artificial disc implant according to the present invention.
Figure 42:
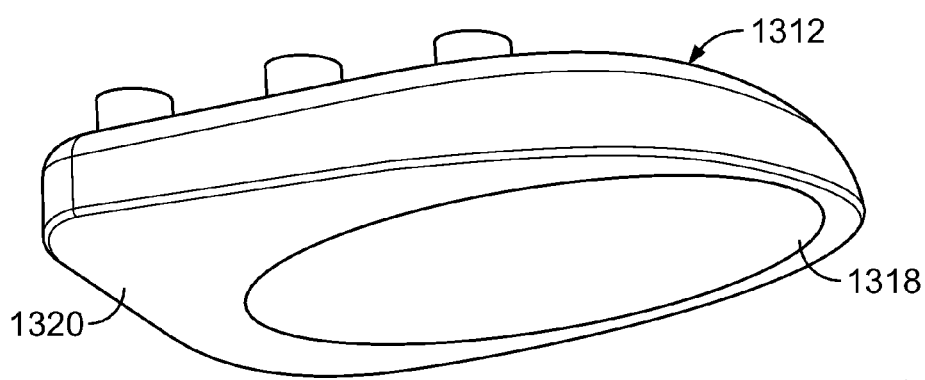
FIG. 42 is a posterolateral perspective view of the upper artificial disc implant member of FIG. 41.
Figure 43:
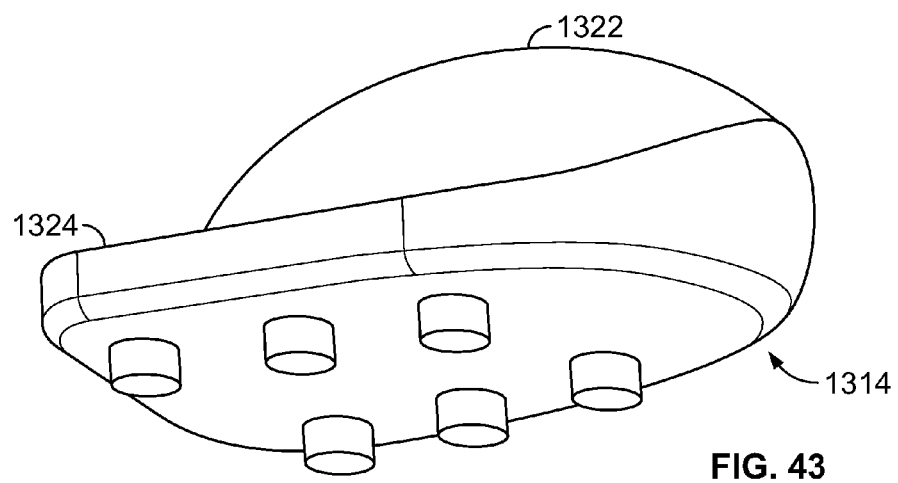
FIG. 43 is a posterolateral perspective view of the lower artificial disc implant member of FIG. 41.

FIG. 41 shows an artificial disc implant 1310 having an upper component or member 1312 and a lower component or member 1314 with the members 1312 and 1314 having a bearing interface 1316 therebetween that allows the members 1312 and 1314 to shift or articulate relative to each other when implanted and secured in an intervertebral space. The bearing interface 1316 can be in the form of a concave recess 1318 formed in the inner or lower surface 1320 of the upper disc member 1312 (FIG. 42), and a convex dome 1322 that projects up from inner or upper surface 1324 of the lower disc member 1314 (FIG. 43). Manifestly, the orientation of the bearing interface 1316, and specifically the concave recess 18 and convex dome 1322 can be reversed such that the recess 18 would be formed on the lower implant member 1314 while the dome 1322 would be formed on the upper member 1312. Preferably, the radius of curvature of the concave recess 1318 and convex dome 1322 are the same for smooth sliding engagement therebetween, although differences in the radius of curvature can also be utilized if desired.

Preferably, both the upper and lower disc members 1312 and 1314 are formed of a PEEK (polyetheretherketone) material which has been found to provide the disc implant 1310 with excellent strength and wear characteristics that are desirable for a joint that is intended for motion preservation such as the artificial disc implants described herein.

Figure 44:
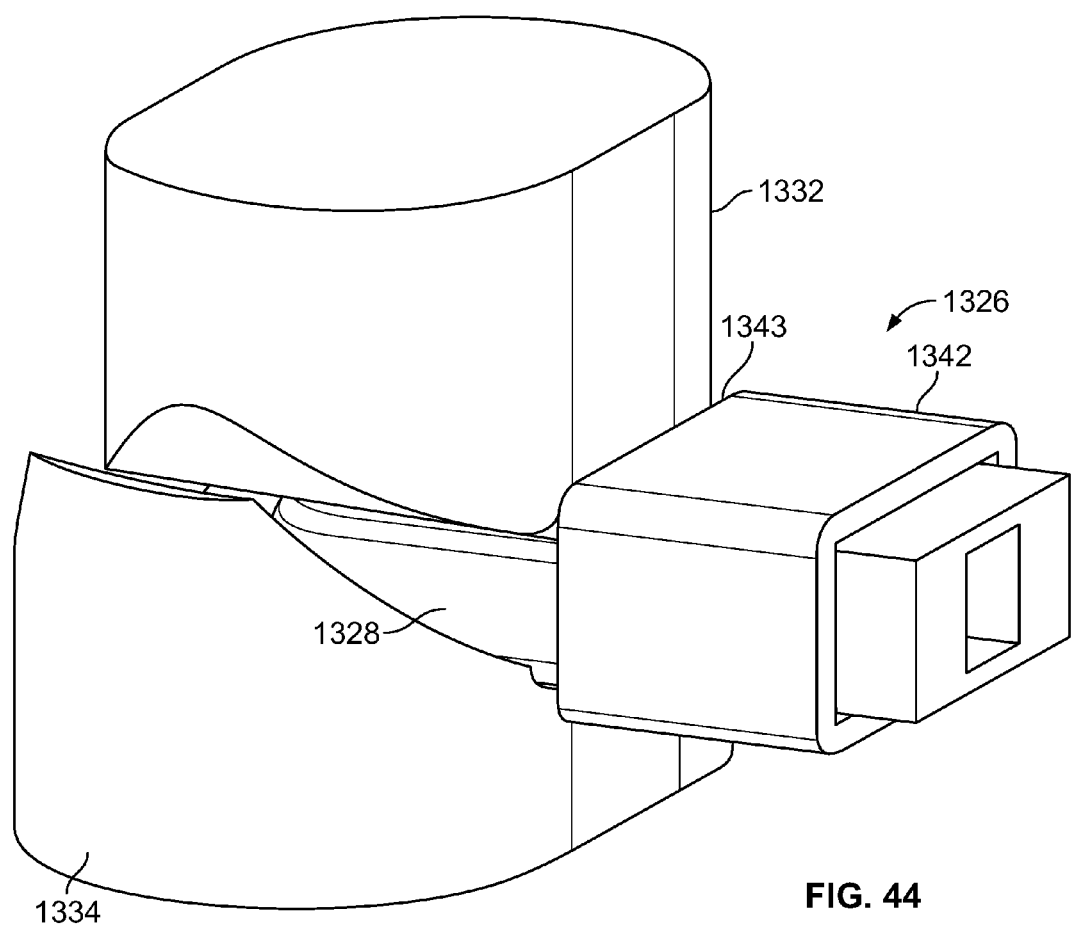
FIG. 44 is an anterolateral perspective view of a trial spacer assembly according to the present invention inserted between two adjacent vertebrae.
Figure 45:
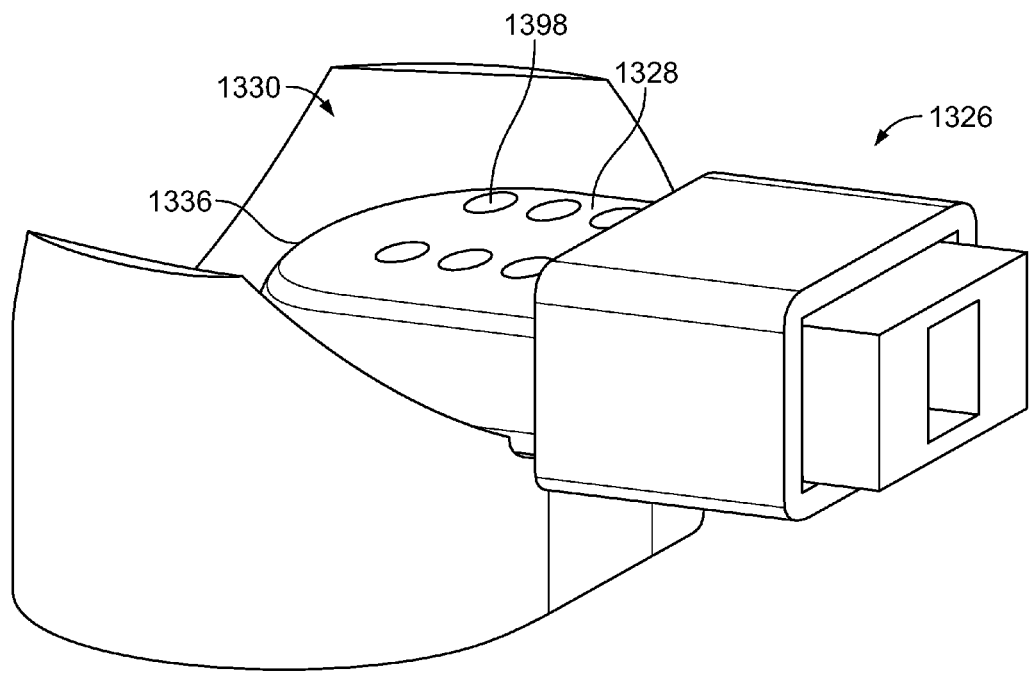
FIG. 45 is an anterolateral perspective view of the trial spacer assembly of FIG. 44 with the upper vertebra hidden for illustration purposes.
Figure 46:
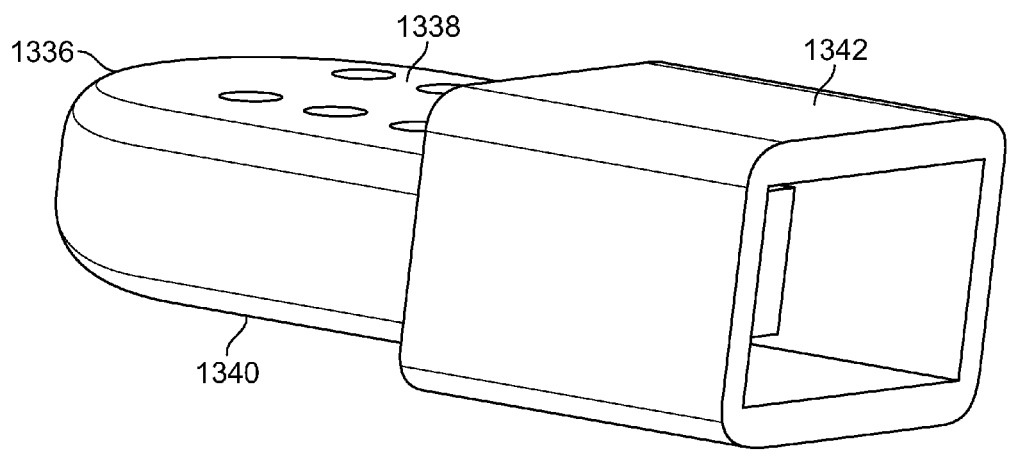
FIG. 46 is an anterolateral perspective view of the trial spacer assembly of FIG. 44.

Referring to FIG. 44, a trial spacer assembly 1326 is shown that includes a forward, trial spacer portion 1328 that is inserted into the intervertebral space 1330 between adjacent, upper and lower vertebral bodies 1332 and 1334. The trial spacer portion 1328 has a generally tongue-shaped configuration including a rounded distal end 1336 and generally flat upper and lower surfaces 1338 and 1340, as best seen in FIGS. 45 and 46. The outer surfaces of the trial spacer portion 1328 present a generally smooth, continuous periphery of the trial spacer portion 1328 for smooth insertion thereof into the intervertebral space 1330. This smooth tongue configuration for the trial spacer portion 1328 substantially corresponds to the peripheral configuration of the disc implant 1310 less the integrated securing mechanism thereof, as will be described hereinafter.

The forward trial spacer portion 1328 is connected to an enlarged rear portion 1342 that remains outside the intervertebral space 1330 after the trial spacer portion 1328 is fully inserted therein, as shown in FIG. 44. The trial spacer portion 1328 and rear portion 1342 have a hollow interior with the rear portion 1342 having a generally rectangular box-like configuration. As shown, there is a transverse shoulder surface 1343 between the trial spacer portion 1328 and rear portion 1342 that acts as a stop to engage the vertebral bodies 1332 and 1334 with the trial spacer portion 1328 fully inserted into the intervertebral space 1330.

Figure 47:
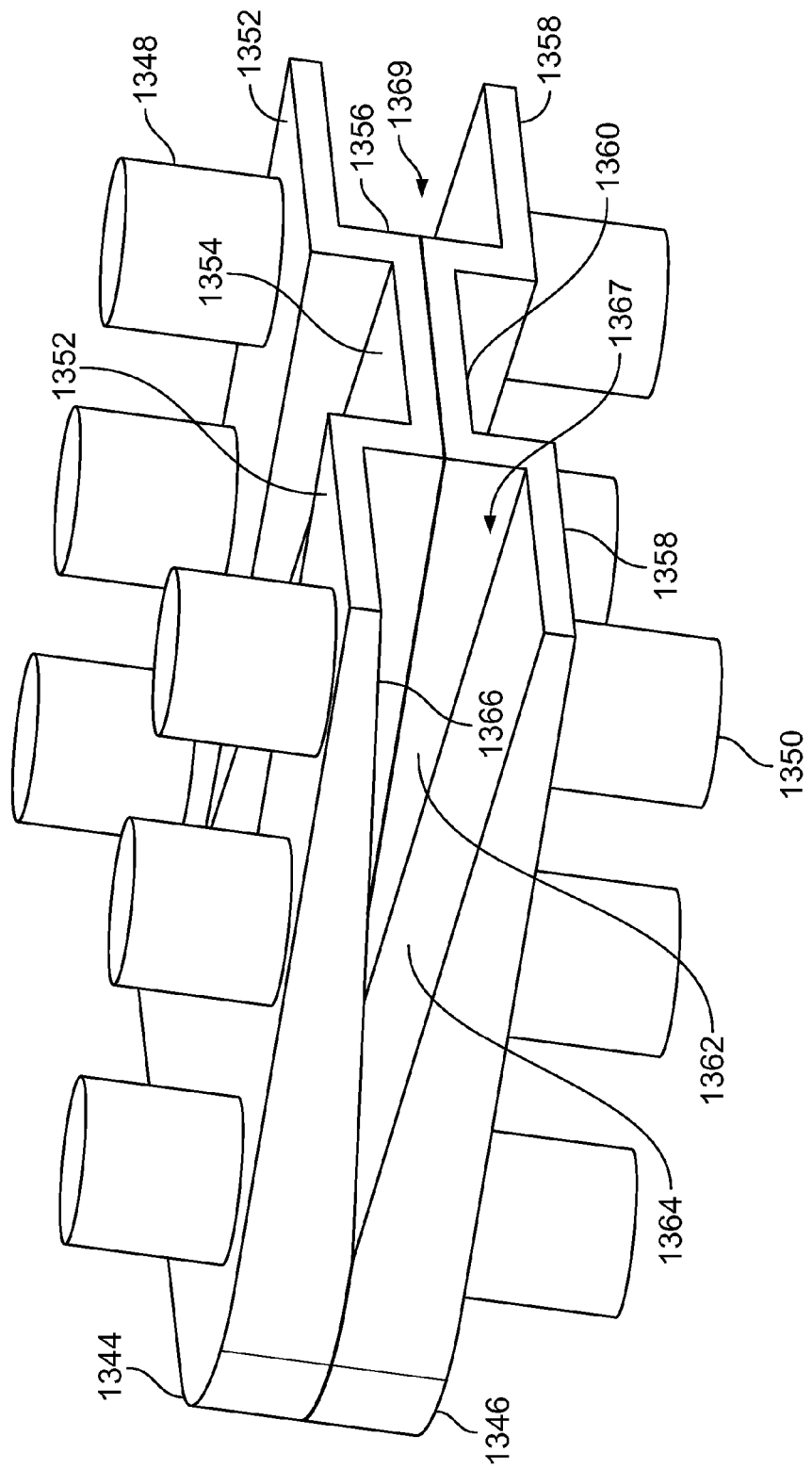
FIG. 47 is an anterolateral perspective view of the internal components of the trial spacer of FIG. 44.
Figure 48:
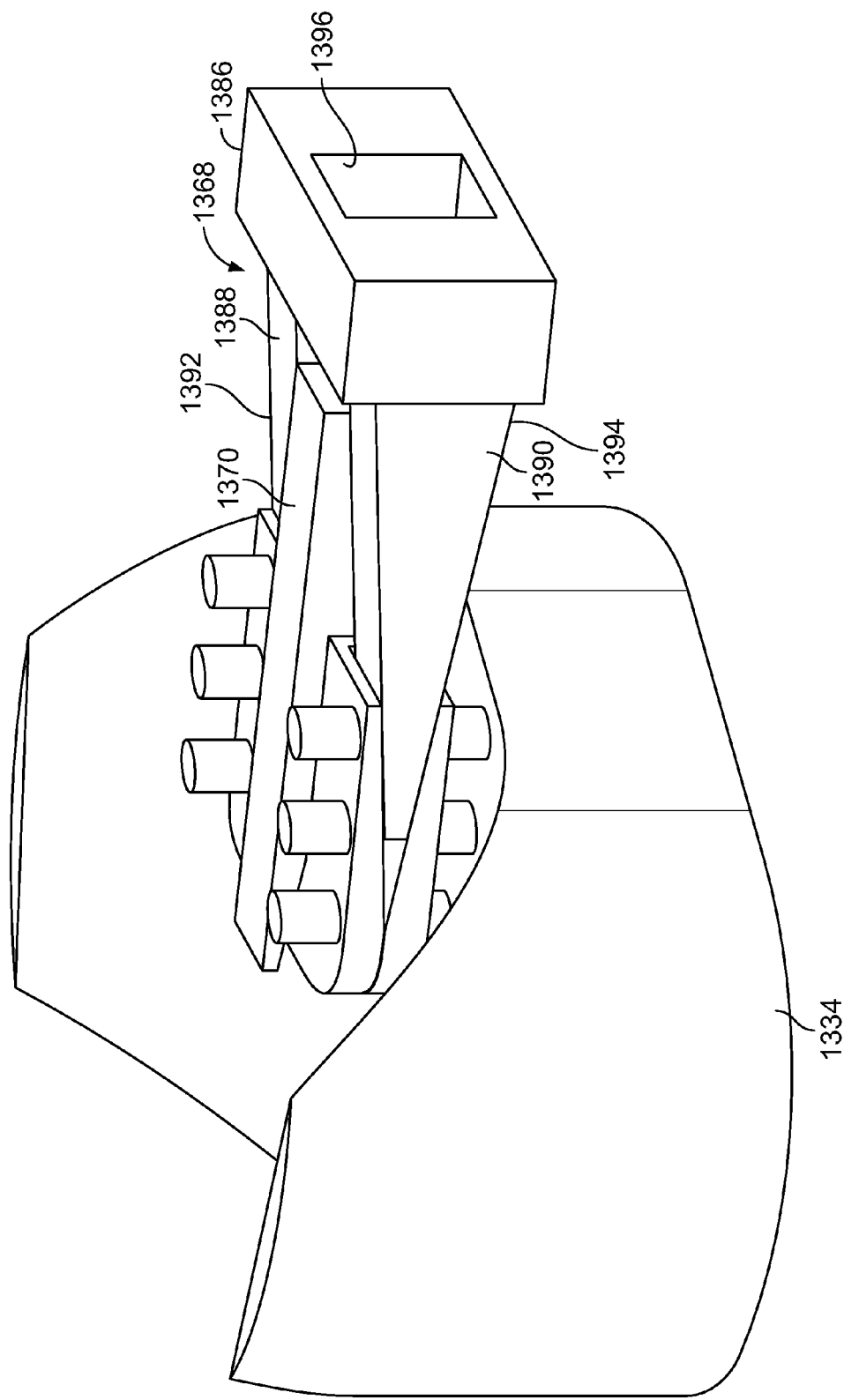
FIG. 48 is an anterolateral perspective view of the components of FIG. 47 including a spreader device disposed between the vertebrae.
Figure 49:
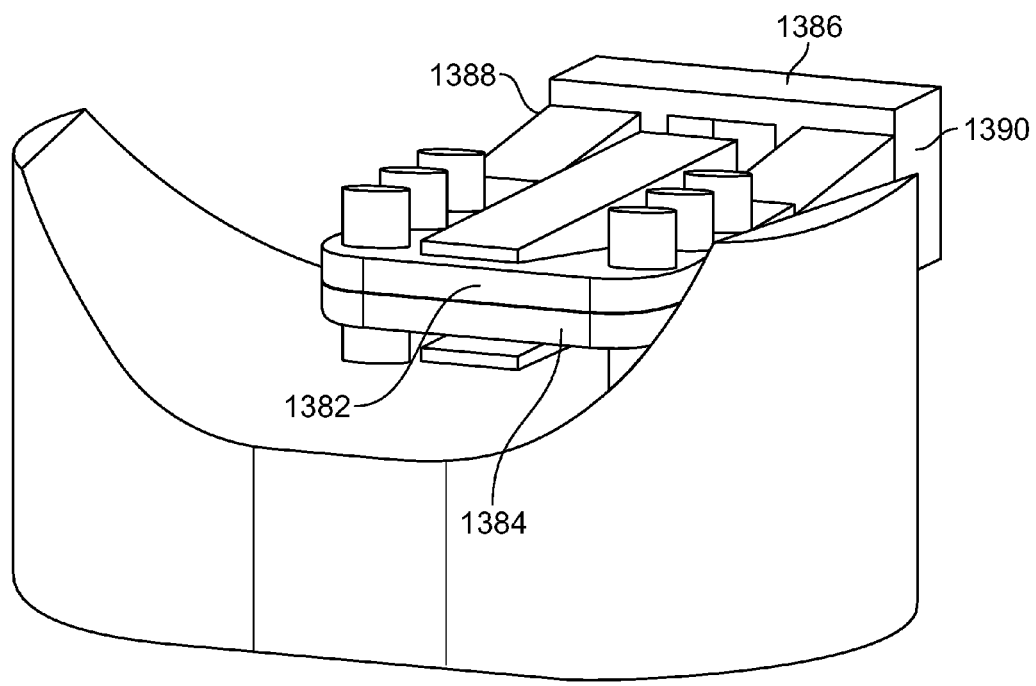
FIG. 49 is a posterolateral perspective view of the trial spacer internal components of FIG. 47.

The hollow portion of the tongue 1328 contains a pair of plates 1344 and 1346 with the upper plate 1344 including several upstanding posts 1348 and the lower plate 1346 including several depending posts 1350 corresponding in positioning to the posts 1348, as can be seen in FIGS. 47-49. The posts 1348 and 1350 are used to form correspondingly spaced openings in the facing surfaces of the vertebral bodies 1332 and 1334. As shown, the posts 1348 and 1350 have blunt end surfaces, although other configurations for these ends can also be used to ease driving of the posts 1348 and 1350 into the bone surfaces.

Referring to FIG. 47, the upper plate 1344 includes raised side platform portions 1352 each having three posts 1348 equally spaced therealong and upstanding therefrom. A central ramp portion 1354 is recessed from the raised side portions 1352 at its rear end and extends at an incline upwardly and forwardly toward the forward end 1382 of the upper plate 1344. Intermediate vertical wall portions 1356 extend along either side of the ramp portion 1354 to interconnect the ramp portion 1354 and the side platform portions 1352 of the upper plate 1344. The lower plate 46 has a similar configuration to the upper plate 1344 in that it also has lowered, side platform portions 1358 that each include three posts 1350 equally spaced therealong and depending therefrom. A central ramp portion 1360 extends between the side portions 1358 and is raised at its rearward end and extends at an incline downwardly and forwardly toward the forward end 1384 of the lower plate 1346. Intermediate vertical wall portions 1352 interconnect the side platform portions 1358 and the central ramp portion 1360.

The corresponding platform portions 1352 and 1358 of the plates 1344 and 1346 cooperate to form a wedge-shape elongate openings or channels 1367 and 1369 by way of their facing inclined surfaces 1364 and 1366. More specifically, the corresponding wall portions 1356 and 1362 and the inclined surfaces 1364 and 1366 cooperate to form wedge-shaped side channels 1367 and 1369 which are used to drive the plates 1344 and 1346 apart for creating the indentations or pocket openings in the vertebral bodies, as described further hereinafter.

Figure 50:
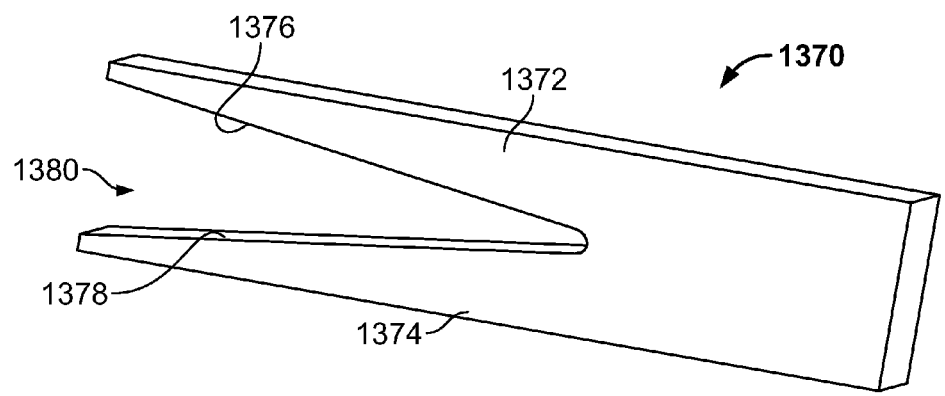
FIG. 50 is a perspective view of the closing device of the trial spacer assembly.

Referring to FIG. 48, in addition to the upper and lower plates 1344 and 1346, the internal components of the trial spacer assembly 1326 include a spreader device 1368, and a generally block-shaped, closing device 1370 shown in their compact or insertion/removal configuration. Referring to FIG. 50, the closing wedge device 1370 has upper and lower projecting arms 1372 and 1374 including inclined facing surfaces 1376 and 1378, respectively. The surfaces 1376 and 1378 cooperate to form a V-shaped opening 1380. In the insertion configuration, the closing device 1370 has the ramp portions 1354 and 1360 of the plates 1344 and 1346 fully received in the V-shaped opening 1380 with the surfaces 1376 and 1378 fully engaged on the ramp portions 1354 and 1360, as shown in FIGS. 48 and 49. In this manner, the plates 1344 and 1346 are held together with the respective forward ends 1382 and 1384 in engagement, as is best seen in FIG. 49.

The spreader device 1368 has an enlarged rear, box-shaped portion 1386 that fits in the hollow space defined by a box-shaped portion 1342 of the trial spacer assembly 1326. The spreader device 1368 also includes forwardly projecting arms 1388 and 1390 laterally spaced so that the wedge device 1370 fits therebetween, as can be seen in FIGS. 48 and 49. As best seen in FIG. 48, the arms 1388 and 1390 have a wedge configuration so that they fit into the corresponding wedge channels 1367 and 1369 formed on either side of the plates 1344 and 1346. In this regard, each of the wedge arms 1388 and 1390 have inclined surfaces 1392 and 1394 that extend from their rear ends at the portion 1386 and taper down toward each other at their forward ends in the channels 1367 and 1369.

Accordingly, to drive the plates 1344 and 1346 apart, the spreader device 1368 and wedge device 1370 are moved in opposite directions with the wedge device 1370 being advanced forwardly so that the inclined surfaces 1392 and 1394 cam against the corresponding plate inclined surfaces 1364 and 1366 to drive the upper plate 1344 in an upward direction toward the vertebral body 1332 and the lower plate 1346 downwardly toward the vertebral body 1334. The rear portion 1386 of the spreader device 1368 has a window opening 1396 to allow the closing device 1370 to fit therethrough so that as the spreader device 1368 is advanced, the wedge device 1370 can be retracted off of the ramp portions 1354 and 1360 of the plates 1344 and 1346 and through the window opening 1396 to allow the plates 1344 and 1346 to be spread apart. In addition, the trial spacer portion 1328 is provided with through openings 1398 so that the posts 1348 and 1350 can be driven therethrough and into the facing surfaces of the vertebral bodies 1332 and 1334. As can be seen in FIG. 45, openings 1398 are shown in the upper portion of the trial spacer portion 1328 through which the upper posts 1350 are driven. Similar openings are provided in the lower portion of the trial spacer portion 1328 for the lower posts 1350.

To remove the trial spacer portion 1328 from the intervertebral space 1330, the trial spacer assembly 1326 is shifted back from its spread or expanded configuration to its insertion/removal or compact configuration with the plates 1344 and 1346 held together with the closing device 1370. For this purpose, the operation of the spreader device 1368 and the closing device 1370 is reversed with the closing device 1370 being advanced forwardly through the window opening 1396 of the spreader device 1368 and the spreader device 1368 being retracted rearwardly until the plate ends 1382 and 1384 are brought together as shown in FIG. 49 with the surfaces 1376 and 1378 of the closing device 1370 once more fully engaged on the ramp surfaces 1354 and 1360. As the trial spacer assembly 1326 is shifted back to its compact configuration, the posts 1348 and 1350 are retracted back through their corresponding openings 1398 in the trial spacer portion 1328 and into the hollow space therein.

After the trial spacer assembly 1326 is utilized as described above to form openings or indentations 1398 in the facing surfaces of the vertebral bodies 1332 and 1334, the implant 1310 is inserted into the intervertebral space 1330 via inserter tool 1400. The inserter tool 1400 has an elongate shaft 1402 and an enlarged head 1404 at its end in which it carries the disc implant 1310 for insertion thereof. Shaft 1402 and the head 1404 are formed by an upper elongate tool member 1406 and a lower elongate tool member 1408 having shaft portions 1410 and 1412, respectively, and an associated head portion 1414 and 1416 at their respective ends. The upper and lower tool members 1406 and 1408 are able to slidingly reciprocate relative to each other for removal of the disc 1310 from the intervertebral space 1330, as will be described more fully hereinafter.

Figure 51:
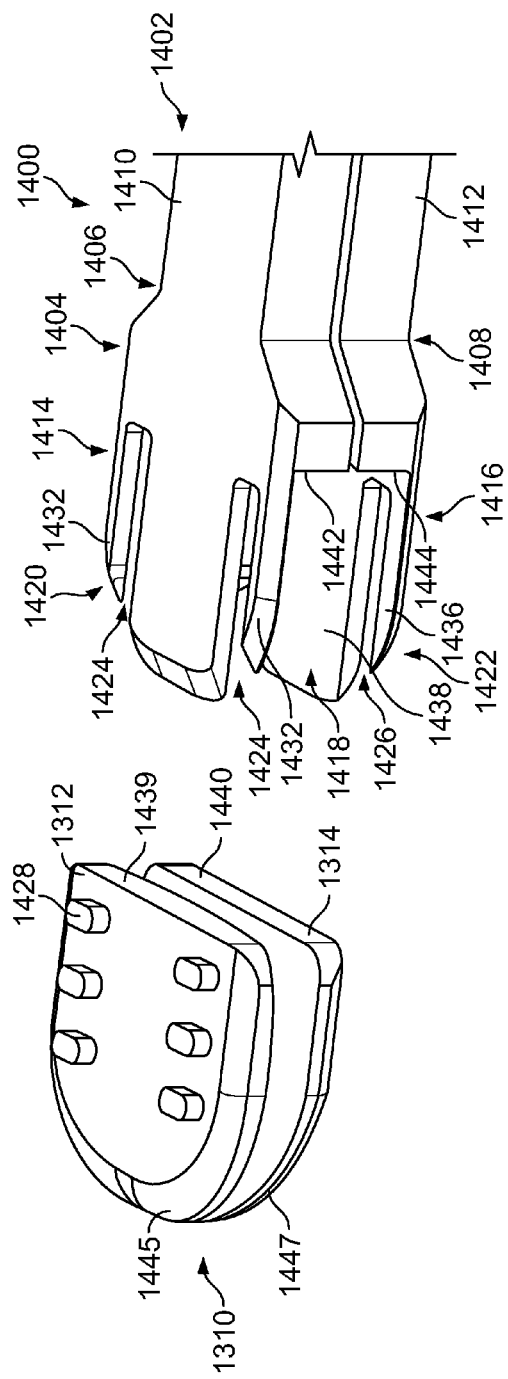
FIG. 51 is an anterolateral perspective view of the artificial disc implant of FIG. 41 with the implant inserter.

As shown in FIG. 51, the tool head 1404 has a forward opening 1318 between upper and lower plate portions 1420 and 1422 of the respective upper and lower head portions 1414 and 1416. The opening 1418 between the plate portions 1420 and 1422 is sized to receive the implant 1310 therein. In this regard, each plate portion 1420 and 1422 has respective side slots 1424 and 1426 formed therein. The slots 1424 and 1426 allow the securing mechanism, in the form of upstanding posts 1428 that are integral with and project up from the upper disc member 1312, and depending posts 1430 that are integral with and project downwardly from the lower disc member 1314, to fit therein. The slots 1424 and 1426 are defined by side prongs that extend along either side of a central projection of each of the tool member head portions 1414 and 1416. More specifically, the upper head portion 1414 has side prongs 1432 on either side of central projection 1434, and the lower head portion 1416 has side prongs 1436 on either side of central projection 1438. The posts 1428 are formed in two rows of three equally spaced posts 1428 on either side of the upper disc member 1312, and the lower posts 1430 are formed similarly in two rows of three equally spaced lower posts 1430 on lower disc member 1314 so that the posts 1428 and 1430 correspond to the spacing and positioning of the posts 1348 or 1350 of the plates 1344 and 1346, and the openings 1398 that they form in the vertebral bodies 1332 and 1334.

As shown in FIG. 51, the implant 1310 is arranged so that the straight upper and lower ends 1438 and 1440 thereof are facing rearwardly so that they abut against the shoulder abutment walls 1442 and 1444 at the rear end of the disc receiving opening 1418 in the tool head 1404. In this regard, the upper and lower actuator ends 1445 and 1447 are arranged forwardly so as to be at the trailing end of the disc implant 1310 as it is inserted into the tool head opening 1418. So that the upper plates 1420 and 1422 substantially match the configuration of the upper and lower disc members 1312 and 1314, the prongs 1432 and 1436 do not extend as far forwardly as the adjacent central projection 1434 and 1438, respectively. In addition, the peripheral edges of the side prongs 1432 and 1436 and the respective central projections 1434 and 1438 have an actuate chamfer to match that of the ends 1445 and 1447 of the disc members 1312 and 1314, respectively. In this manner, with the disc 1310 fully received in the tool head opening 1418 as shown in FIG. 52, the projecting ends 1445 and 1447 of the disc implant 1310 present a substantially smooth, continuous surface in combination with the corresponding, adjacent edges of the prongs 1432 and 1436 and central projections 1434 and 1438.

Figure 52:
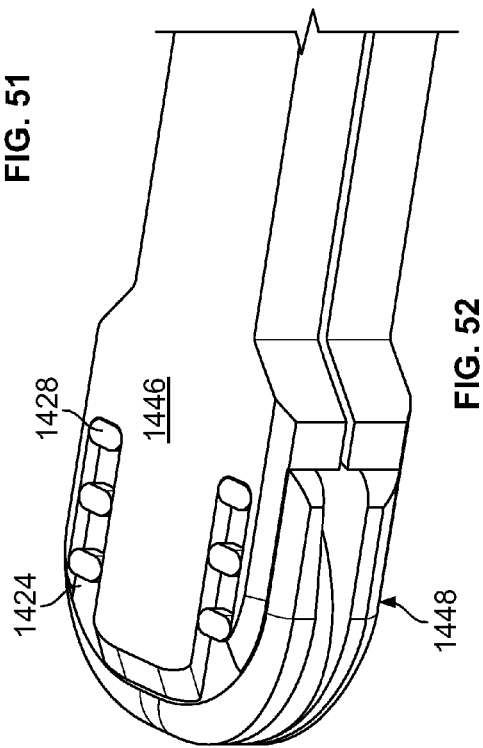
FIG. 52 is an anterolateral perspective view of the implant of FIG. 41 loaded in the inserter of FIG. 51.
Figure 53:
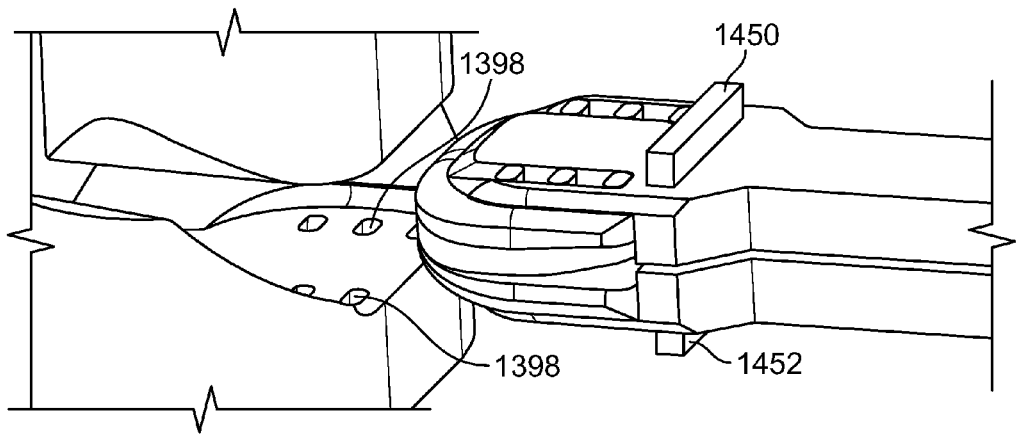
FIG. 53 is an anterolateral perspective view of the implant of FIG. 41 loaded in the inserter of FIG. 51 adjacent the intervertebral space prior to insertion.

Referring to FIG. 52, the implant posts 1428 and 1430 are received in the respective slots 1424 and 1426. As shown, the rearmost posts 1428 abut against the end of the slots 1424 with the upper and lower disc member ends 1439 and 1440 engaged against the shoulder walls 1442 and 1444 with the disc implant 1310 fully received in the tool head opening 1418. Similarly, the rearmost lower posts 1430 are engaged at the end of lower slots 1426 with the upper and lower disc ends 1439 and 1440 engaged against the shoulder walls 1442 and 1444 with the disc implant 1310 fully received in the tool head opening 1418. As shown, the spacing the plates 1420 and 1422 is such that with the posts 1428 and 1430 received in the slots 1424 and 1426, the upper ends of the posts 1428 and 1430 will be substantially flush with the top and bottom surfaces 1446 and 1448 of the plate portion 1420 and 1422, respectively. In this manner, the disc implant 1310 is smoothly inserted into the intervertebral space 1330 with the inserter tool 1400. Also, the inserter tool plates 1420 and 1422 are spaced so as to distract the vertebral bodies 1332 and 1334 apart for fitting the disc implant 1310 therebetween. In other words, the spacing between the surfaces 1446 and 1448 of the respective plates 1420 and 1422 is slightly greater than the spacing between the surfaces 1338 and 1340 of the trial spacer portion 1328 of the trial spacer assembly 1326. This allows the disc posts 1428 and 1430 to be fit into the openings 1398.

More specifically, the upper and lower tool members 1406 and 1408 preferably include respective, laterally extending stop members 1450 and 1452 that are spaced slightly rearwardly of the rear ends of the slots 1424 an 1426. The tool 1400 is advanced forwardly to fit the tool head 1404 and artificial disc 1310 carried thereby into the intervertebral space 1330. The tool 1404 continues to be advanced forwardly until the stops 1450 and 1452 abut against the vertebral bodies 1332 and 1334 to provide the user an indication that the tool head 1404 and the artificial disc 1310 carried thereby are fully received in the intervertebral space 1330. With the stops 1450 and 1452 engaged against the respective vertebral bodies 1332 and 1334, the posts 1428 and 1430 are now properly aligned with the pocket openings 1398 formed in each of the vertebral bodies 1332 and 1334.

Figure 54:
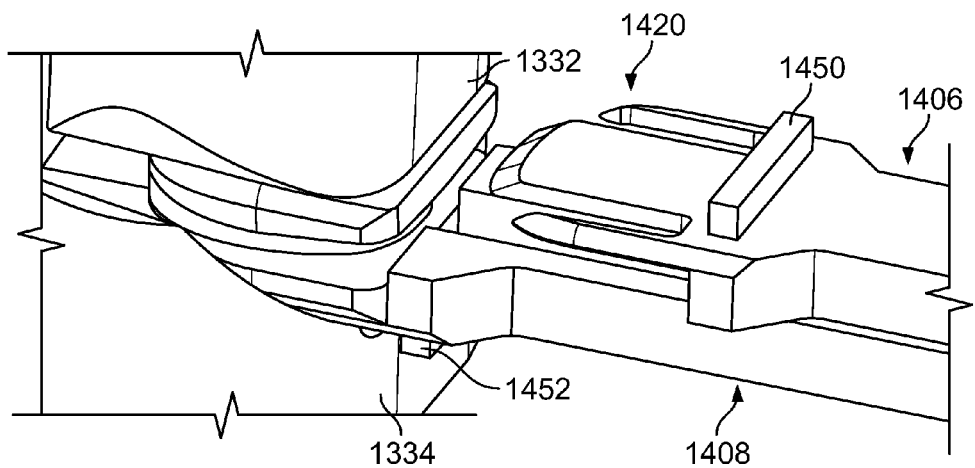
FIG. 54 is an anterolateral perspective view of the implant and inserter of FIG. 53 with the upper arm of the inserter retracted from the implant.
Figure 55:
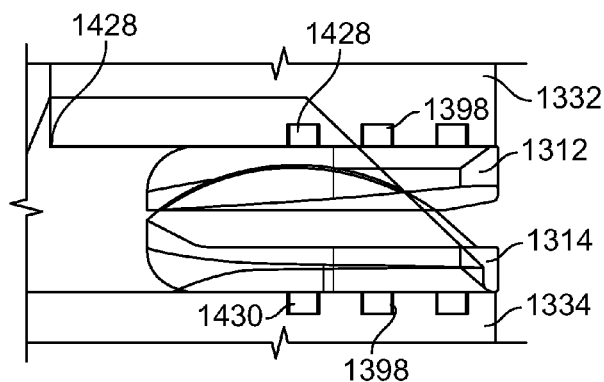
FIG. 55 is a side view of the implant of FIG. 41 implanted within the intervertebral space.

As previously mentioned, the tool members 1406 and 1408 are slidable relative to each other so that one of the members 1406 and 1408 can be retracted while the other member 1406 or 1408 remains in its advanced position with the corresponding stop 1450 or 1452 engaged against the corresponding vertebral body 1332 or 1334. As shown in FIG. 54, upper tool member 1406 is retracted while the lower tool member 1408 remains in its advanced position with the stop 1452 thereof engaged against the vertebral body 1334. With the plate 1420 retracted out from the intervertebral space 1330, the distracted vertebral body 1332 will shift down toward the vertebral body 1334 causing the posts 1428 of the disc upper member 1312 to be received in the corresponding preformed pocket openings 1398 in the vertebral body 1332. Thereafter, the lower tool member 1408 is retracted to pull the plate member 1422 out from the intervertebral space 1330 so that the posts 1430 can fall into the corresponding preformed pocket openings 1398 formed in the vertebral body 1334, as shown in FIG. 55. With the disc implant 1310 secured to the vertebral bodies 1332 and 1334 in the intervertebral space 1330 therebetween via the fitting of the posts 1428 and 1430 into the pocket openings 1398, the risk that the disc 1310 will be extruded out from the intervertebral space 1330 is substantially minimized as the vertebral bodies 1332 and 1334 move relative to each other via the bearing interface 16 between the secured upper and lower disc members 1312 and 1314.

Figure 56:
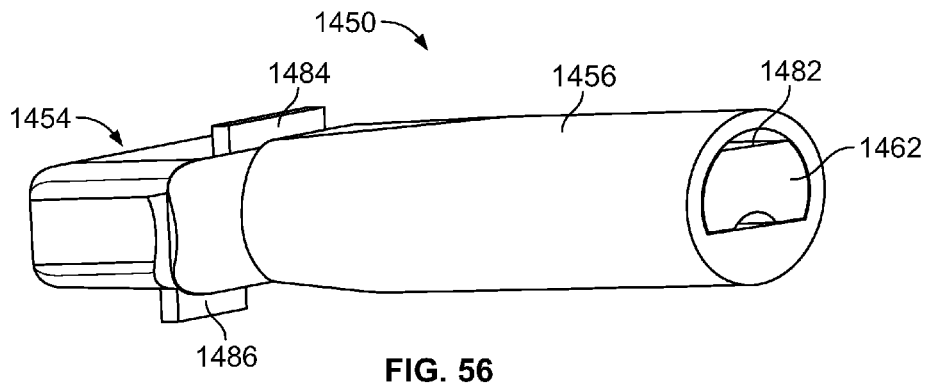
FIG. 56 is an anterolateral perspective view of a trial spacer assembly according to the present invention.

In the next trial spacer and disc implantation and securing system, a trial spacer assembly 1450 as shown in FIG. 56 is employed. The trial spacer assembly 1450 also is utilized to form features in the vertebral bodies 1334 and 1336 for receipt of the securing mechanism that is associated with the artificial disc implant 1452 (FIG. 52). The disc implant 1452 only varies from the disc implant 1310 in the securing mechanism employed so that the common features between the disc implants 1310 and 1452 will not be described in detail hereinafter.

Figure 58:
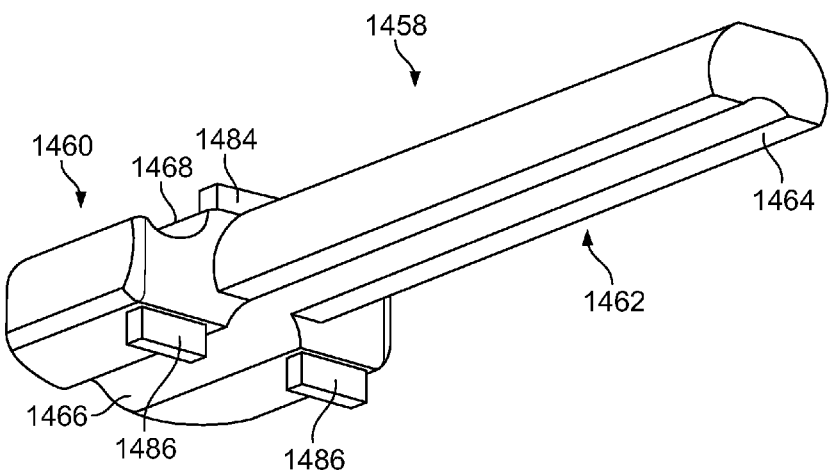
FIG. 58 is a anterolateral perspective view of the trial spacer assembly of FIG. 56 with the shaft handle removed.
Figure 59:
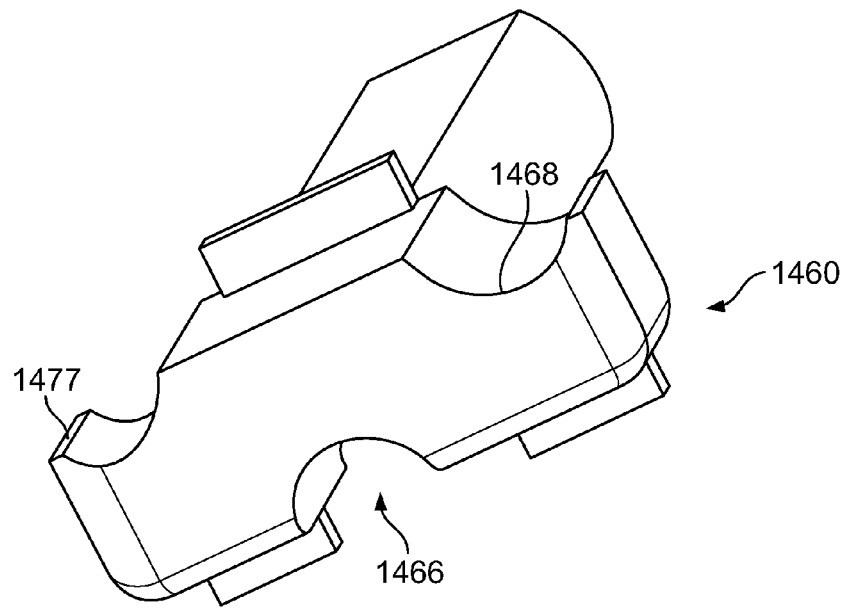
FIG. 59 is a posterolateral perspective view of the trial spacer assembly of FIG. 58.

The trial spacer assembly 1450 has a forward, trial spacer portion 1454 that has an outer, peripheral configuration substantially matching that of the disc implant 1452 less the securing mechanism thereof. The trial spacer assembly 1450 also includes a rearwardly extending shaft portion 1456. The trial spacer assembly 1450 is formed from two components. As shown in FIG. 58, the main trial spacer member 1458 includes a head trial spacer portion 1460 and a rearwardly extending shaft portion 1462. The shaft portion 1458 has an elongate lower groove 1464 formed along its entire length, and the head portion 1460 also includes an elongate lower groove 1466 aligned with the shaft groove 1464, as shown in FIG. 58. In addition, the head portion 1460 has a pair of upper grooves 1468 and 1470 on either side thereof. The grooves 1464-1470 are used to form features in the vertebral bodies 1332 and 1334 for receipt of the securing mechanism of the disc implant 1452, as described more fully hereinafter.

Figure 60:
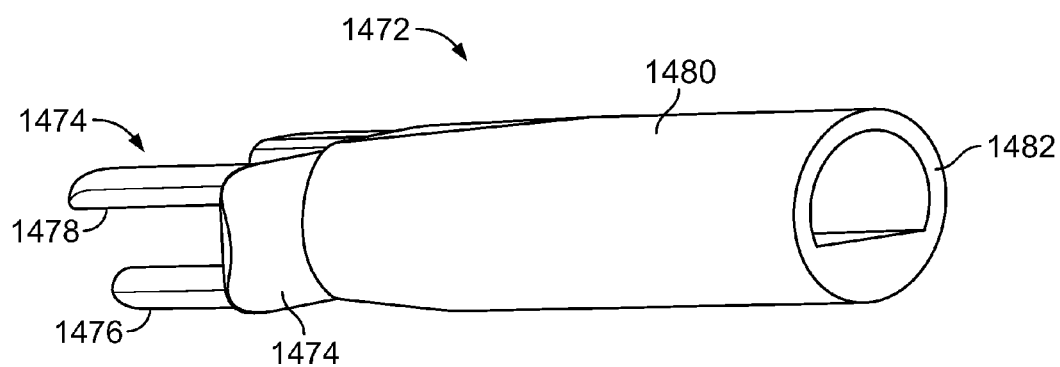
FIG. 60 is an anterolateral perspective view of the shaft handle of the trial spacer assembly of FIG. 56.

The second component of the trial spacer assembly 1450 is a head cover and handle member 1472. The member 1472 includes a head cover portion 1474 that consists of a laterally extending, rear flange portion 1474 from which a central lower prong 1476 and a pair of upper prongs 1478 extend forwardly. Shaft handle portion 1480 extends rearwardly from the flange portion 1474 and has a hollow throughbore 1482 extending therethrough opening to the flange portion 1474, as seen in FIGS. 60 and 61.

Figure 57:
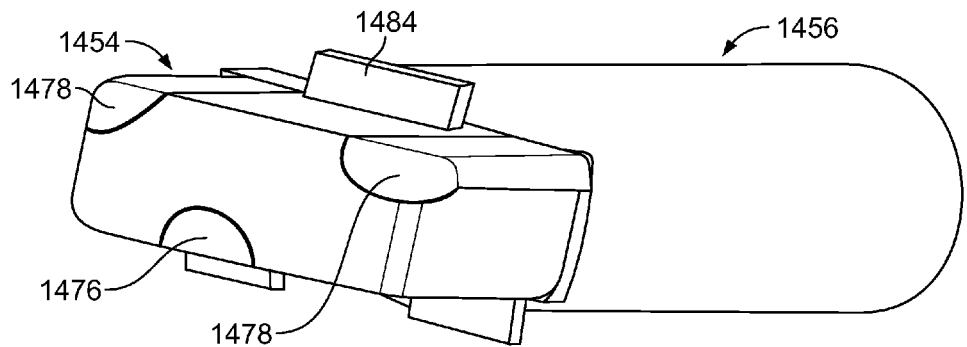
FIG. 57 is a posterolateral perspective view of the trial spacer assembly of FIG. 56.

The trial spacer assembly 1450 is assembled by sliding the head cover and handle member 1472 over the trial spacer member 158 with the shaft portion 1462 fitting into the throughbore 1482 and the prongs 1476 and 1478 fitting into the corresponding grooves 1466-1470 of the trial spacer head portion 1460. Referring to FIG. 56, the throughbore 1482 has a generally D-shaped configuration so that the shaft portion 1462 is non-rotatably received therein. Further, as can be seen in FIG. 57, the prongs 1476 and 1478 fit into the corresponding grooves 1466-1470 such that the outer, peripheral surface of the trial spacer portion 1454 has no sharp or discontinuous surfaces that might otherwise gouge the vertebral bodies 1332 and 1334 during insertion of the trial spacer portion 1454 into the intervertebral space 1330. Also, the trial spacer portion 1460 is provided with three laterally extending stop members including central, upper stop member 1484 that extends laterally between the upper grooves 1468 and 1470, and side, lower stop members 1486 that extend laterally on either side of the central lower groove 1466 with all three stop members 1484 and 1486 being adjacent the rear end of the trial spacer portion 1460.

FIG. 62 shows the trial spacer portion 1454 inserted into the intervertebral space 1330 between adjacent vertebral bodies 1332 and 1334 for assessing the size of the intervertebral space 1330 so as to be able to accurately select an appropriately sized artificial disc 1452 for implantation therein. As shown in FIG. 62, the trial spacer portion 1454 is fully received in the intervertebral space 1330 with the stops 1484 and 1486 engaged against the vertebral bodies 1332 and 1334 and the shaft portion 1462 extending outside the intervertebral space 1330 and away therefrom. Thereafter, the head cover and handle member 1472 are slid off and removed from the trial spacer member 1458 leaving the grooved trial spacer portion 1460 in the intervertebral space 1330 with the shaft portion 1462 extending rearwardly therefrom, as shown in FIG. 63.

Figure 64:
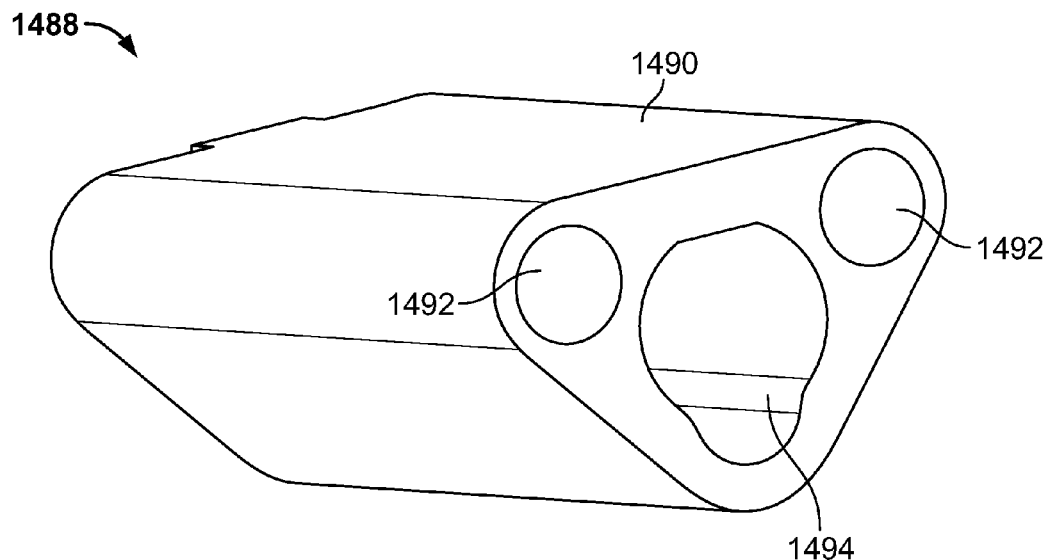
FIG. 64 is an anterolateral perspective view of a drill guide according to the present invention.
Figure 65:
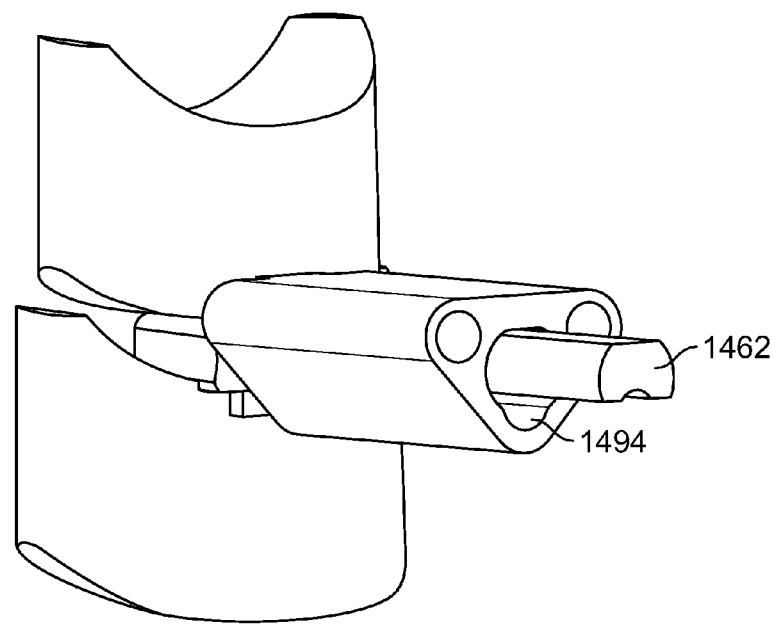
FIG. 65 is an anterolateral perspective view of the drill guide of FIG. 64 inserted over the trial spacer assembly.
Figure 66:
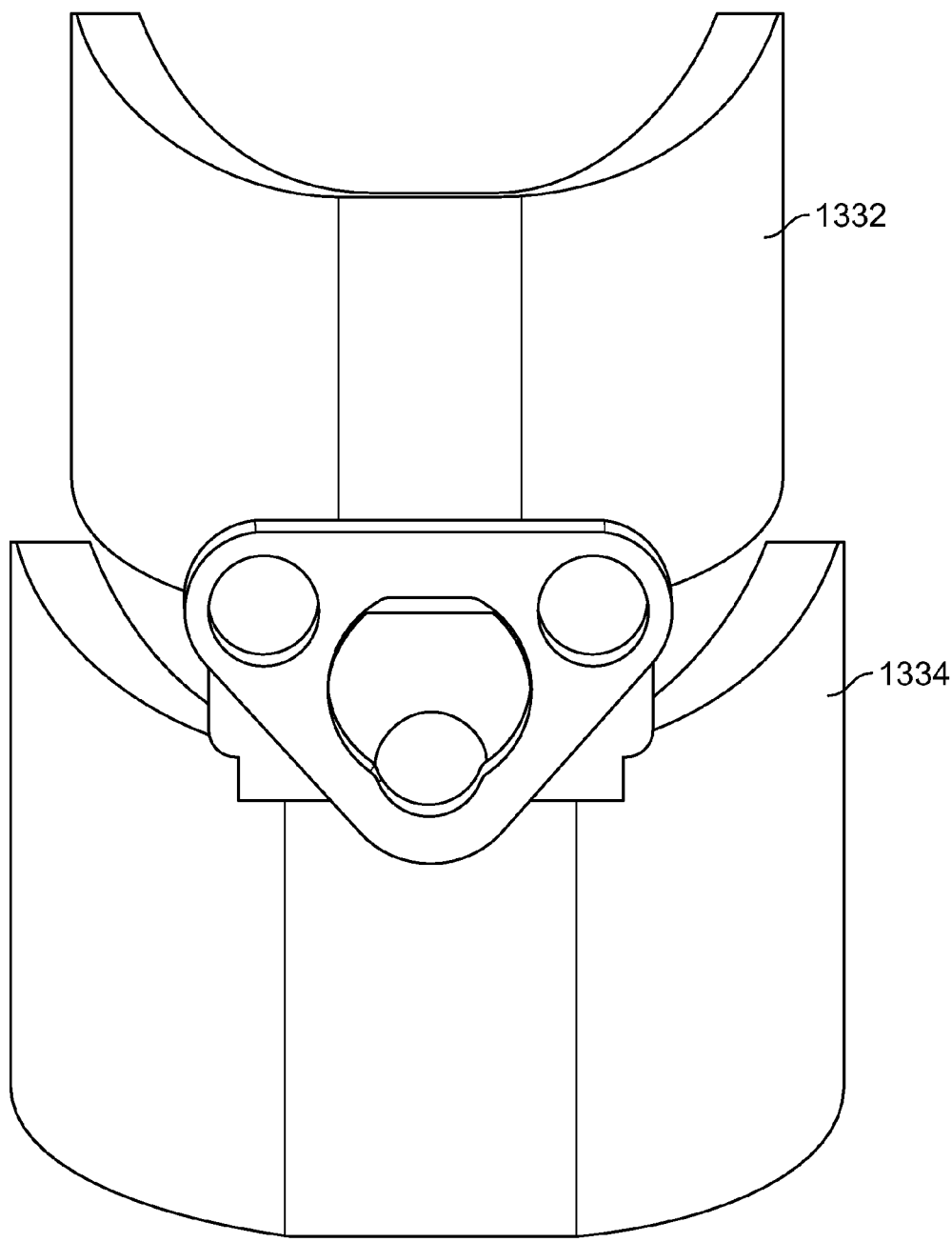
FIG. 66 is an anterior view of the trial spacer and drill guide of FIG. 65.
Figure 67:
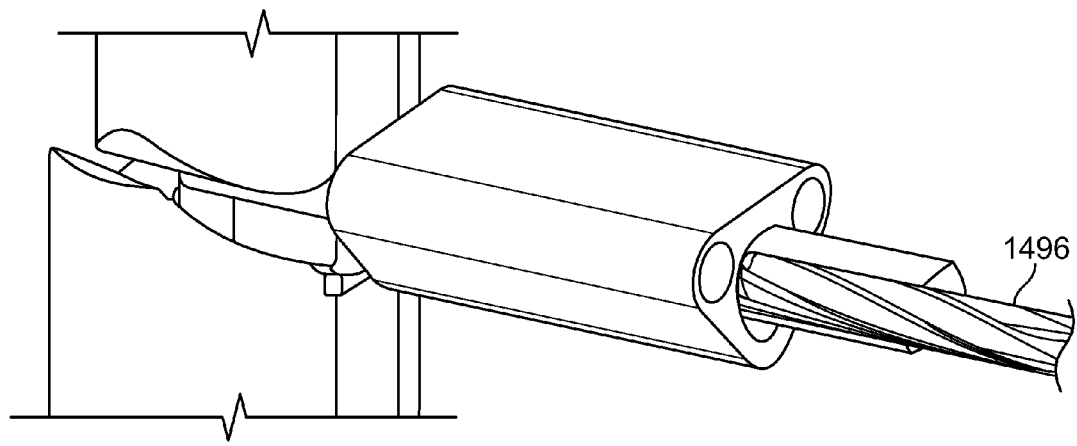
FIG. 67 is an anterolateral perspective view of the trial spacer and drill guide of FIG. 65 with a drill.
Figure 68:
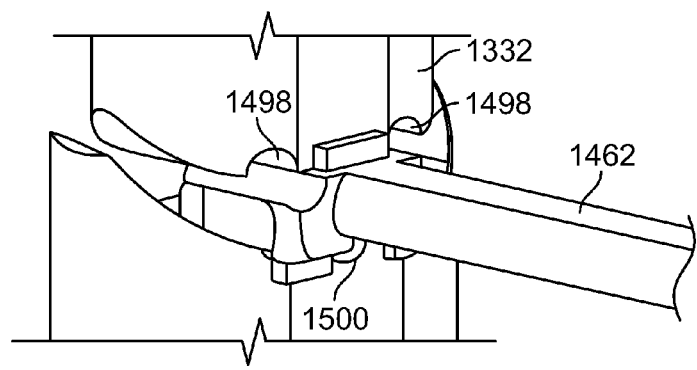
FIG. 68 is an anterolateral perspective view of the trial spacer of FIG. 67 after the grooves have been drilled and the drill guide is removed.

At this point, the trial spacer member 1458 is used in cooperation with a drill guide 1488 for drilling grooves in the vertebral bodies 1332 and 1334 at the facing surfaces thereof. Referring to FIG. 64, the drill guide 1488 has a triangular-block body 1490 with a pair of upper throughbores 1492 extending through the body 1490, and an irregularly-shaped, enlarged central throughbore 1494 between and below the upper, side throughbores 1492. The enlarged, central throughbore 1494 is sized so that the drill guide 1488 can be slid along the trial spacer member 1458 with the shaft portion 1462 fitting in the upper portion of the central throughbore 1494, as shown in FIG. 65. Referring next to FIG. 66, it can be seen that the upper side throughbores 1492 are aligned with the upper grooves 1468 and 1470 in the trial spacer portion 1460 to cooperate therewith in guiding a drill 1496 (FIG. 67) for cutting grooves in the upper vertebral body 1332. Similarly, the lower portion of the central throughbore 1494 of the drill guide 1488 cooperates with the lower groove 1464 in the shaft portion 1462 and lower groove 1466 in the trial spacer portion 1460 to form an opening through which the drill bit 1496 is guided for cutting a groove in the lower vertebral body 1334. FIG. 68 shows the pair of upper grooves 1498 formed along either side of the facing surface of the vertebral body 1332 and the lower groove 1500 formed centrally in the facing surface of the lower vertebral body 1334 with the drill guide 1488 removed from the shaft portion 1462 for purposes of illustrating the grooves 1490 and 1500.

Figure 70:
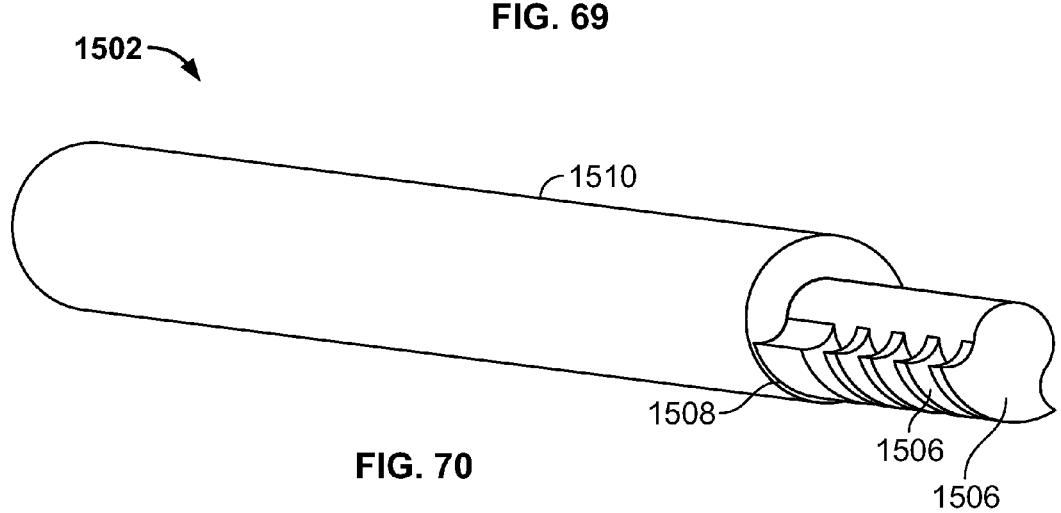
FIG. 70 is a perspective view of the cam cutter of FIG. 69.

Next, a cam cutter 1502 is advanced through the bores 1492 and 1494 in a manner similar to the drill bit 1496. The cam cutter 1502 has a reduced size, radially offset cutting end 1504 including several cutting blade portions 1506, and a counter bore cutting portion 1508 at the rear thereof. An enlarged shaft 1510 extends rearwardly from adjacent to the counter bore cutting portion 1508. The shaft 1510 is sized to fit into the openings through the drill guide 1488 formed in cooperation with the trial spacer member 1458, as previously described with respect to the drill bit 1496. FIG. 70 is a view of the cam cutter 1502 showing the bell-shaped configuration of the cutting blade portions 1506 and counter bore cutting blade portion 1508. The cam cutter 1502 is operable to cut radially enlarged recesses 1512 in the grooves 1498 and 1500 as well as enlarged counter bore portion 1514 at the rear end of the grooves 1498 and 1500. Alternately, the drill bit 1496 can be provided with a stepped configuration to form the counter bore 1514 simultaneously with the drilling of the grooves 1498 and 1500. Similarly, the cam cutter 1502 can be avoided altogether if the securing mechanism for the artificial disc implant 1452 is provided with cutting-type cams, as will be described hereinafter.

Figure 72:
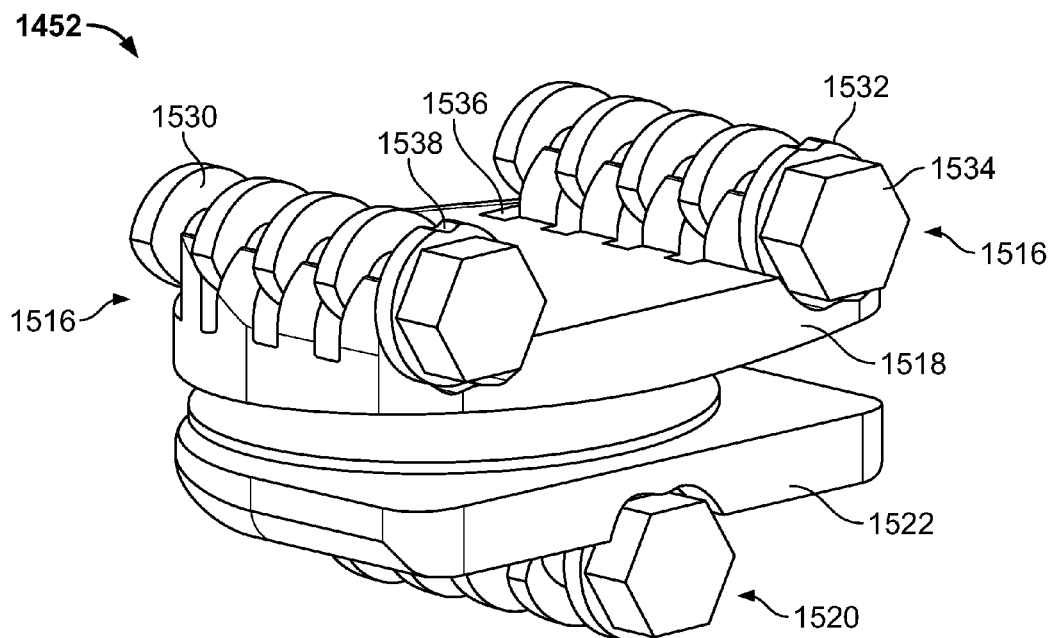
FIG. 72 is an anterolateral perspective view of an artificial disc implant according to the present invention including a securing mechanism in the form of three cam shafts with deployable cam lobe members.
Figure 73:
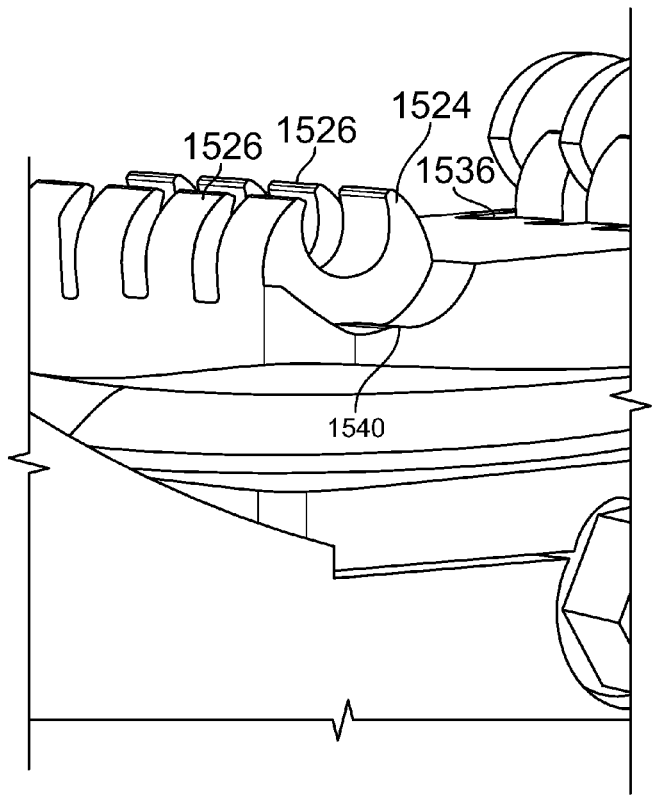
FIG. 73 is an enlarged anterolateral perspective view of the artificial disc implant of FIG. 72 with one cam shaft removed to show the retainer members.

Referring to FIG. 72, the securing mechanism of the disc implant 1452 takes the form of upper cam shafts 216 secured on either side of upper disc implant member 1518, and lower cam shaft 1520 secured centrally to the lower disc implant member 1522. To hold the cam shafts 1516 and 1520 to the respective disc members 1518 and 1522, each is provided with a plurality of spaced upwardly open, U-shaped retainer members 1524. The retainer members 1524 have upwardly extending arms 1526 that are spaced from each other so that the shaft portion 1528 of the cam shafts 1516 and 1520 will be received by a friction fit therebetween. In this regard, the preferred PEEK material from which the disc members 1518 and 1522 including the retainer members 1524 thereof are formed will provide the arms 1526 with sufficient strength and resiliency to provide a secure friction fit with the shaft portions 1528 snap-fit therebetween while allowing for the shaft portions to be rotated to secure the disc members 1518 and 1522 to the corresponding vertebrae 1332 and 1334.

Figure 74:
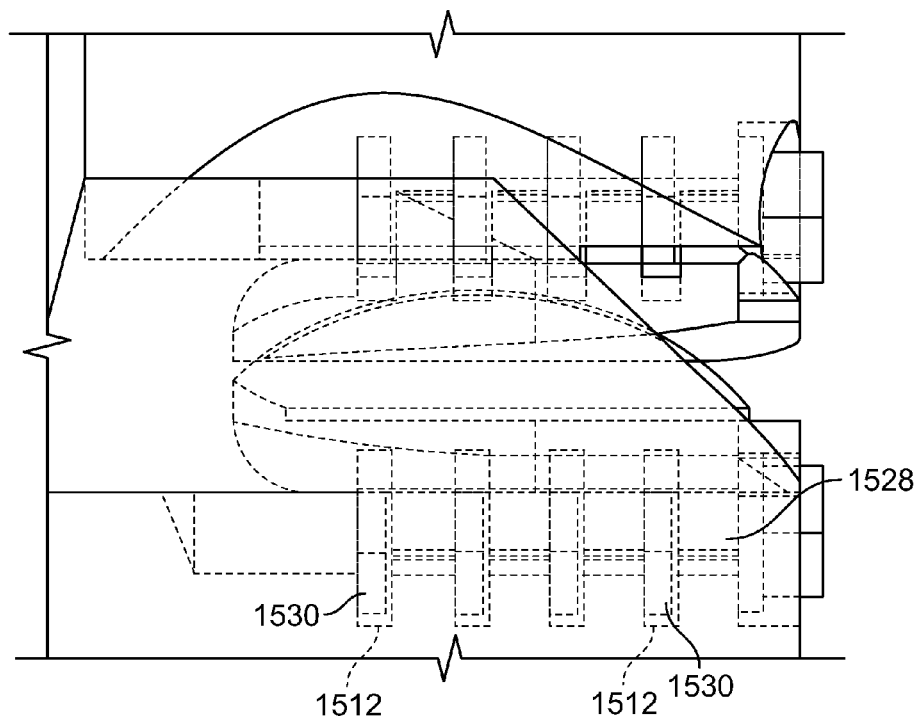
FIG. 74 is lateral view of the implant of FIG. 72 as implanted in the intervertebral space.

More specifically, the cam shafts 1516 and 1522 each include several cam lobe members 1530 spaced along the length thereof and a proximate disc indicator member 1532 adjacent drive head 1534. Initially, the cam shafts 1516 and 1520 are oriented 1480 degrees from their orientation shown in FIG. 72 for insertion of the artificial disc 1452 into the intervertebral space 1330 with the cam shafts 1516 and 1520 received in the corresponding grooves 1498 and 1500 of the vertebral bodies 1332 and 1334. In this regard, the cam lobes 1530 are rotated down into recessed slots 1536 formed in the upper surface of the upper disc member 1518. Rotating the cam shafts 1516 and 1520 via the hex drive heads 1534 thereof by 1480 degrees from their insertion orientation to their secured orientation shifts the cam lobes 1530 into the recesses 1512 cut into the vertebral body grooves 1498 and 1500, as shown in FIG. 74. In this manner, the artificial disc implant 1452 is secured in the intervertebral space 1330 against extrusion out therefrom during articulation of the upper and lower disc members 1518 and 1522 relative to each other as the upper and lower vertebrae 1332 and 1334 shift via the arcuate bearing interface formed between the members 1518 and 1522. The disc indicator member 1532 is sized to be received in the counter bore portion 1514 of the grooves 1498 and 1500. The disc member 1532 can be provided with a pair of diametrically opposite notches 1538 about its periphery that cooperate with a raised nub 1540 on the disc member 1518 so that the user is provided with a tactile indication that the cam shafts 1516 and 1520 have been rotated by 1480 degrees from their insertion orientation to shift the cam lobes 1530 so that they are substantially fully received in the groove recesses 1512.

Figure 75:
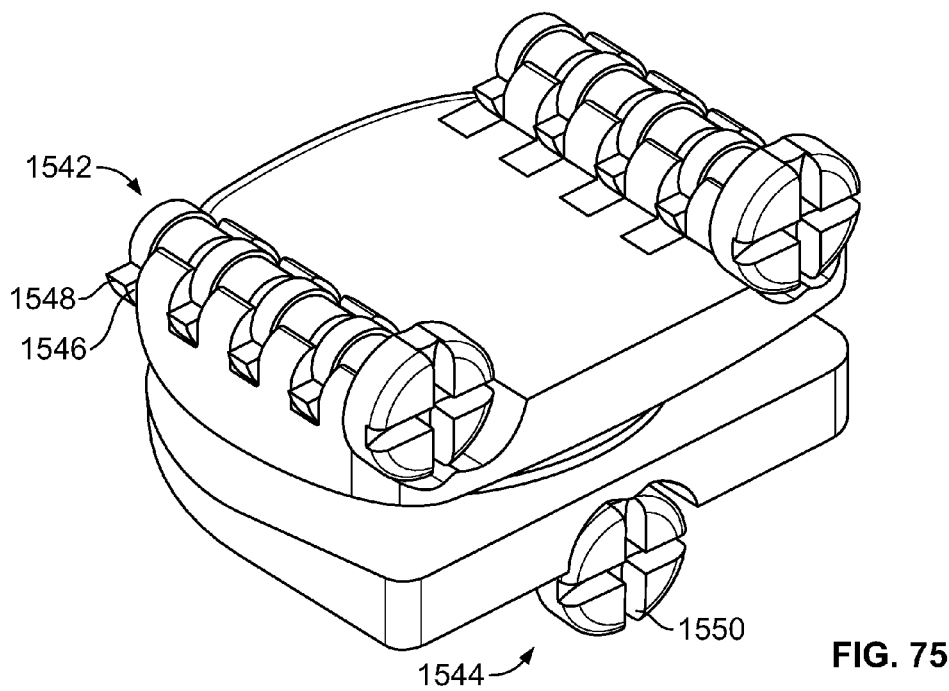
FIG. 75 is an anterolateral perspective view of the implant of FIG. 72 with cam members with sharpened edges for cutting into bone when deployed into the vertebra.
Figure 76:
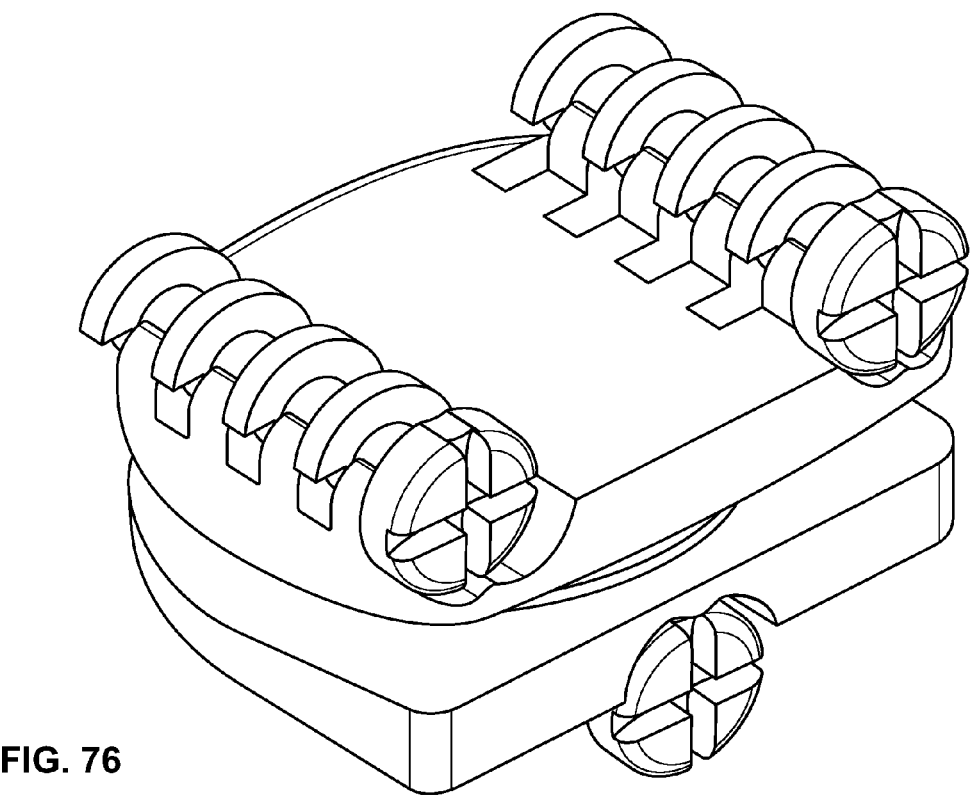
FIG. 76 is an anterolateral perspective view of the implant of FIG. 75 with the cam members fully deployed.

FIGS. 75 and 76 show alternative upper cam shafts 1542 and an alternative lower cam shaft 1544. In this form, the cam members 1546 have more of a flat mushroom-like configuration with sharp corner edges 1548 for cutting into the vertebral bodies 1332 and 1334. In this manner, the separate cam cutter 1502 need not be used for cutting the recesses 1512 in the vertebral body grooves 1498 and 1500. Also, it can be seen that the drive head 1534 can have a cruciform drive recess 1550 rather than having the hex drive configuration of the drive head 1534.

Figure 77:
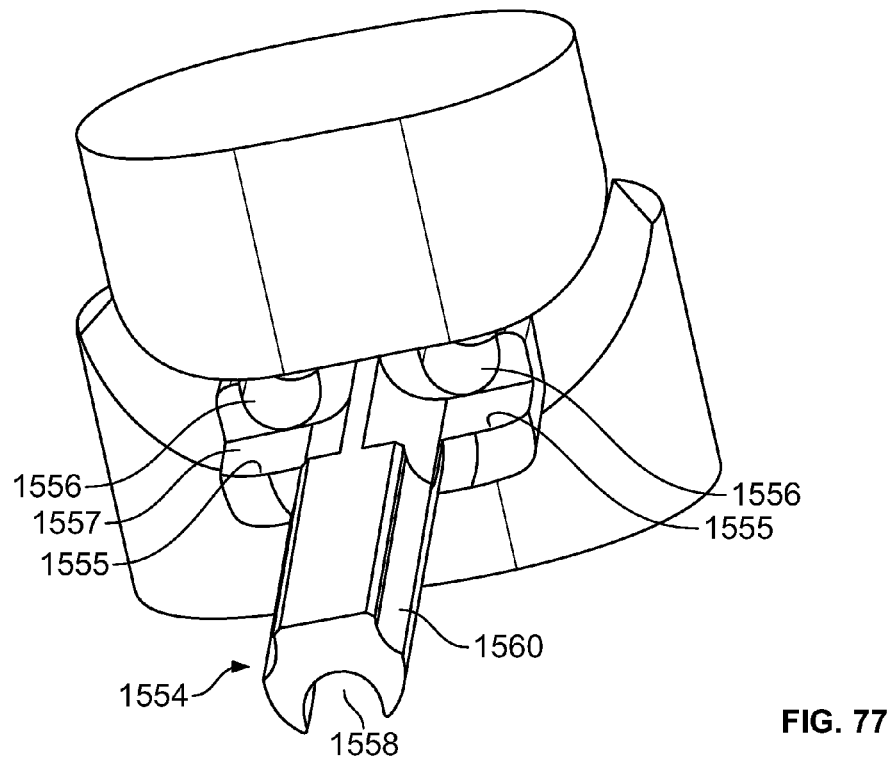
FIG. 77 is an anterior perspective view of a trial spacer member according to the present invention inserted into the intervertebral space.
Figure 85:
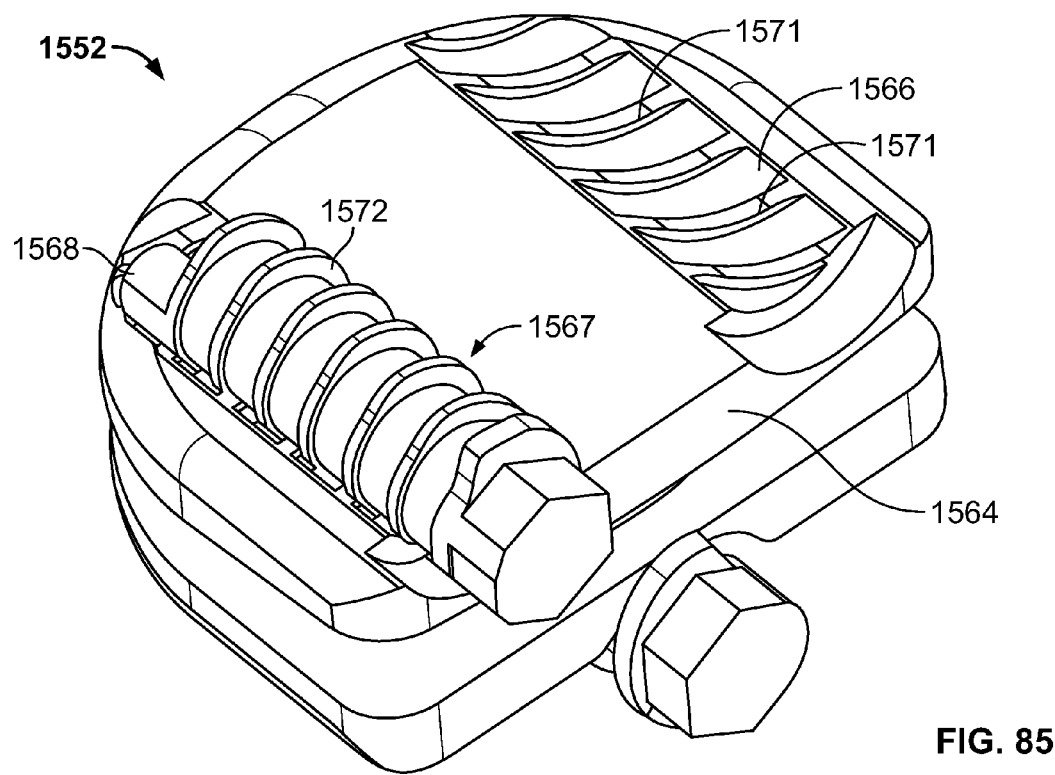
FIG. 85 is an anterolateral perspective view of an artificial disc implant according to the present invention with one cam shaft hidden, wherein the cam shafts are first imbedded into the vertebrae before the implant is inserted.
Figure 86:
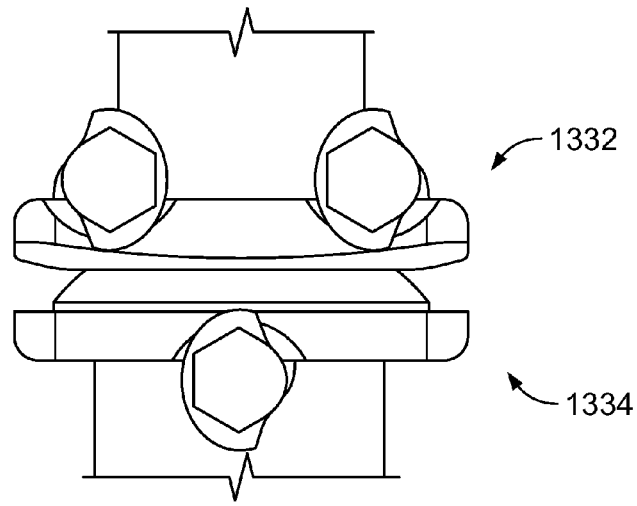
FIG. 86 is an anterior view of the artificial disc implant of FIG. 85 wherein the cam shafts have been rotated 90 degrees to secure the implant with respect to the vertebrae.
Figure 87:
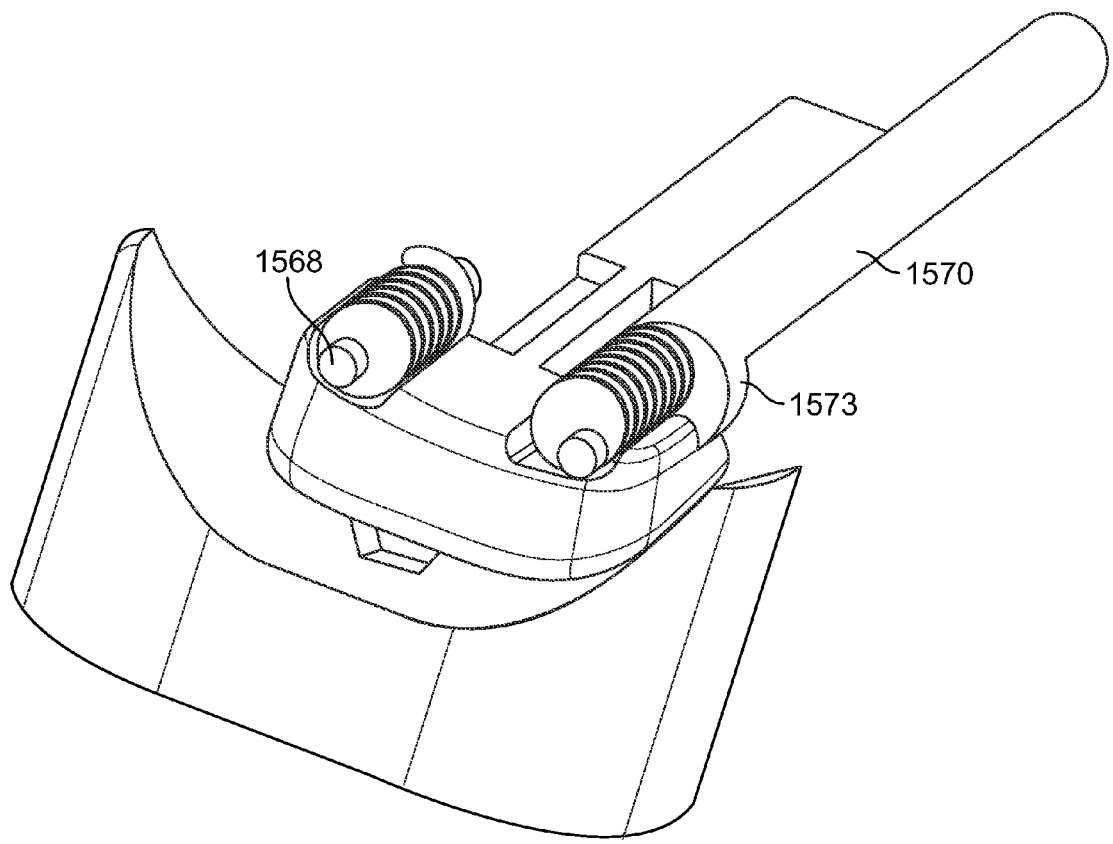
FIG. 87 is a posterolateral view of the trial spacer of FIG. 79 with the cam shaft driver driving one of the cam shafts up into the upper vertebrae, which is hidden for illustration purposes.

The next trial spacer and artificial disc implantation and securing system is similar to the previous system except that the securing mechanism is not associated with the artificial disc as it is inserted into the intervertebral space 1330, but rather is first inserted into the preformed features formed in the vertebral bodies 1332 and 1334 and thereafter deployed therefrom to interconnect the vertebral bodies and the artificial disc implant 1552 (FIG. 85). Referring to FIG. 77, a trial spacer member 1554 is shown having upper side grooves 1556 in the forward head portion 1557 thereof and a lower central groove 1558 that extends in the rear shaft portion 1560 thereof as well as in the forward head portion 1557. The cover and handle member for the trial spacer member 1554 is not shown for illustration purposes but otherwise is similar to the previously described cover and handle member in that it is configured to ensure that the forward trial spacer portion including the grooved head portion 1557 can be inserted smoothly into the intervertebral space 1330 without gouging the vertebral bodies 1332 and 1334.

Figure 78:
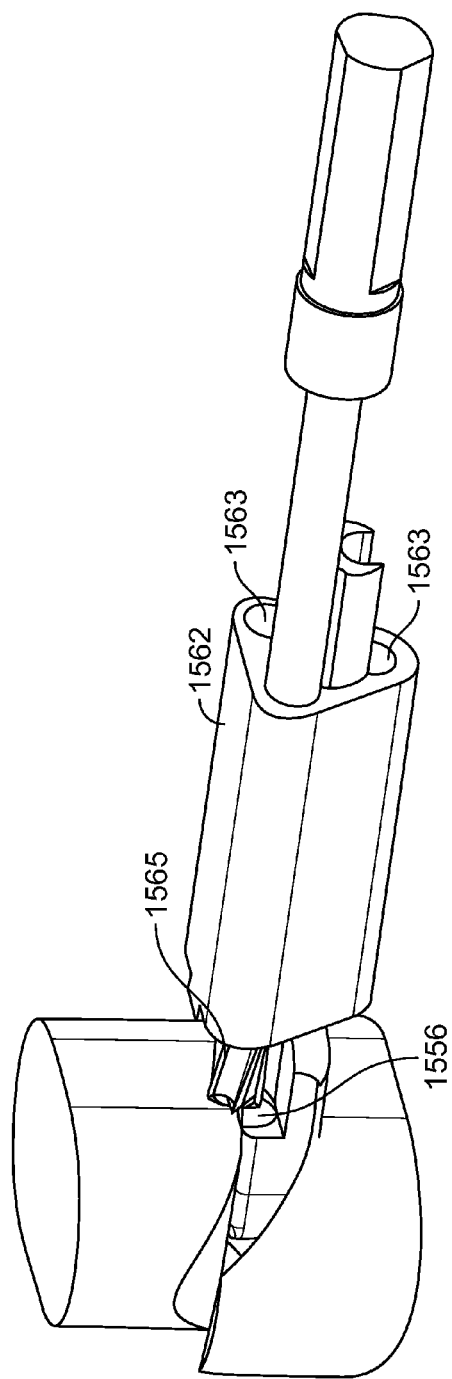
FIG. 78 is an anterolateral perspective view of a trial spacer member of FIG. 77 with a drill guide inserted over the trial spacer for drilling offset grooves into the vertebrae for installing cam shafts directly into the vertebrae.

As shown in FIG. 78, the shaft member 1560 receives a drill guide 1562 thereon which has throughbores 1563 that are slightly offset from the corresponding grooves 1556 and 1558 of the trial spacer member 1554. Accordingly, drill 1565 is guided through the bores 1563 to drill grooves 1569 into the vertebral body 1332 that are slightly offset upwardly from the upper grooves 1556 of the trial spacer member and a groove 1569 into the vertebral body 1334 that is slightly offset downwardly from the lower groove 1558 of the trial spacer member 1554.

Figure 79:
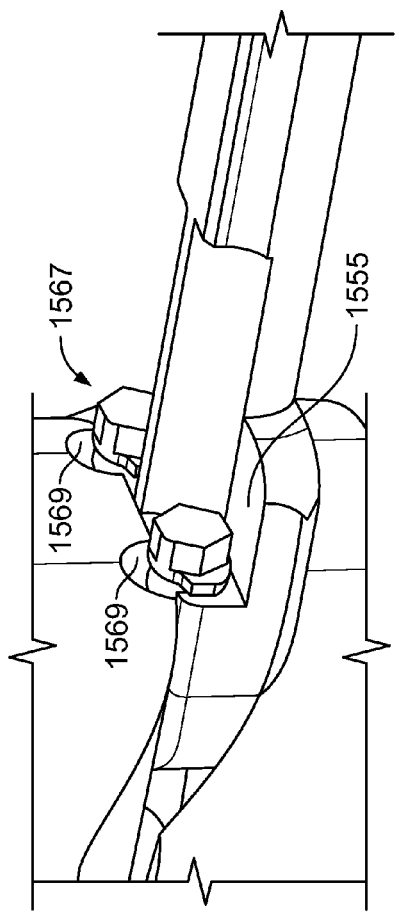
FIG. 79 is an anterolateral perspective view of a trial spacer member of FIG. 77 with the cam shafts inserted into the trial spacer for being imbedded in the vertebra prior to insertion of the implant.
Figure 80:
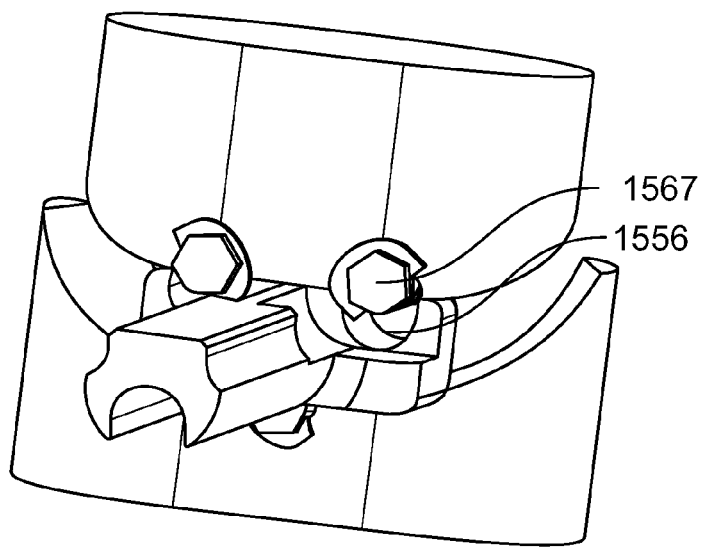
FIG. 80 is an anterolateral perspective view of a trial spacer of FIG. 79 with the cam shafts imbedded into the offset grooves in the vertebrae.

Next, cam shafts 1567 are inserted into the intervertebral space 1330 guided by the grooves 1556 and 1558 of the trial spacer member 1554, and then they are rotated and cammed up into the offset grooves 1569 formed in the upper vertebral body 1332 and down into the offset groove 1569 formed in the lower vertebral body 1334, as shown in FIGS. 79 and 80. The camming action of the cam shafts 1567 is shown in FIGS. 81-84.

Figure 81:
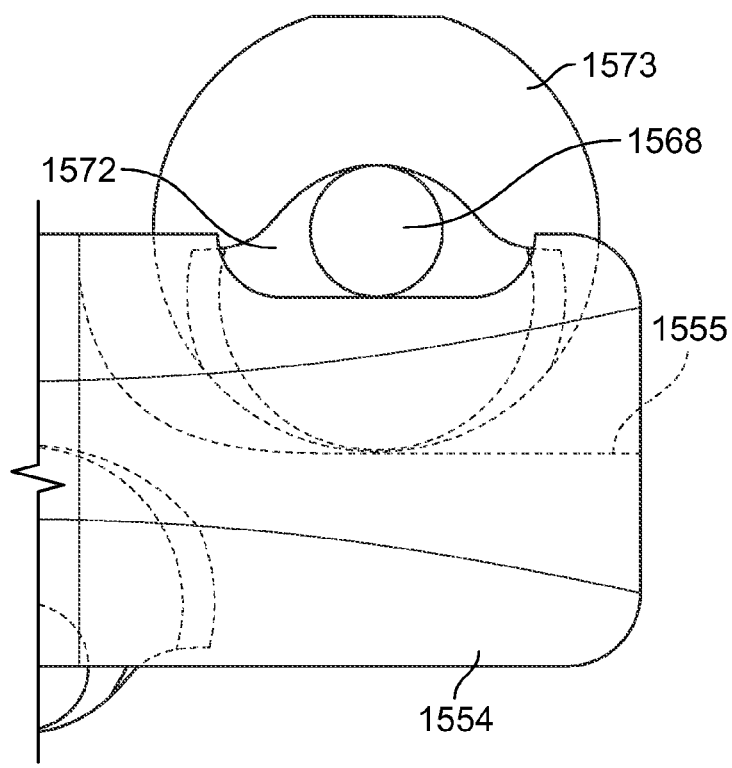
FIGS. 81-84 show a sequence from a posterior viewpoint detailing the operation of the cam shafts from an initial resting point on the trial spacer in FIG. 81 to being cammed up into the vertebrae in FIGS. 82 and 83, and being imbedded into the vertebrae in FIG. 84 so that the trial spacer may be removed and the implant may be inserted.
Figure 82:
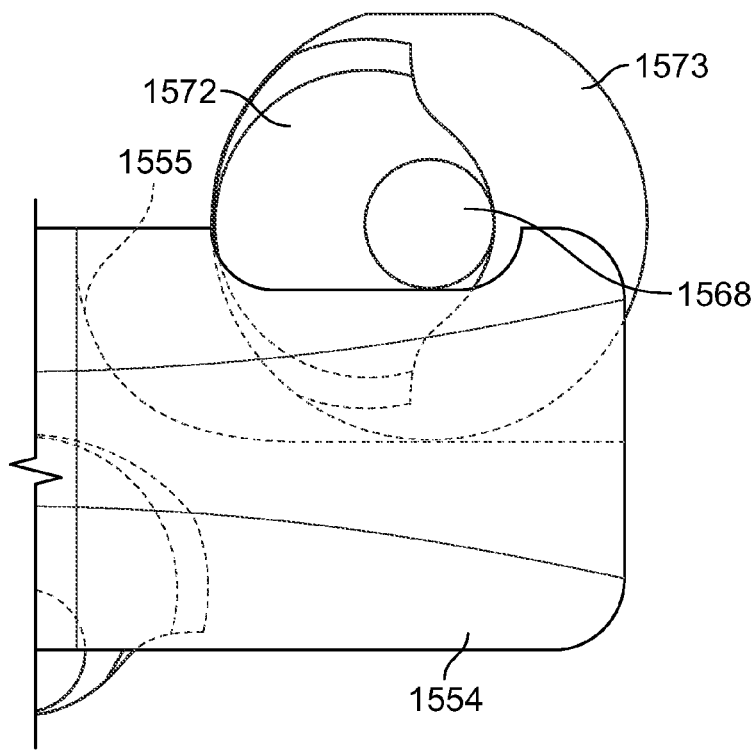
Figure 83:
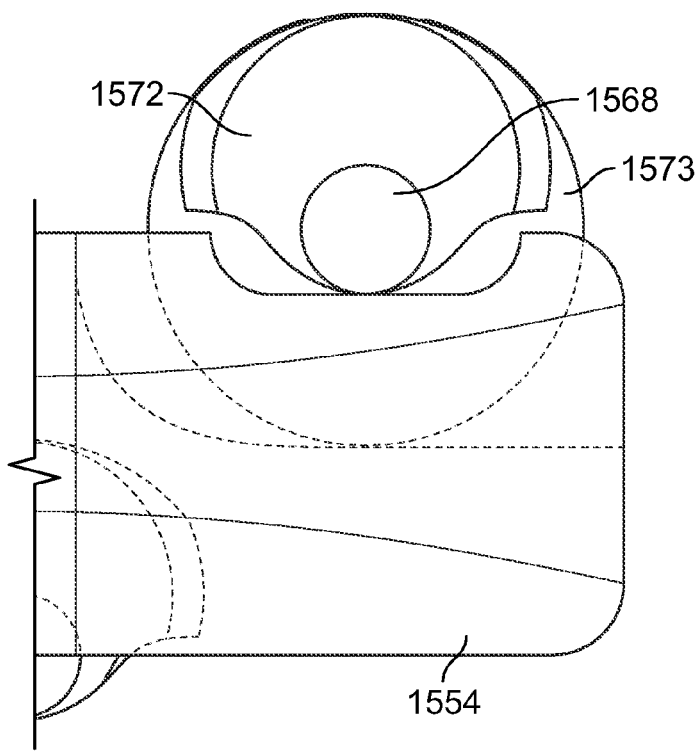
Figure 84:
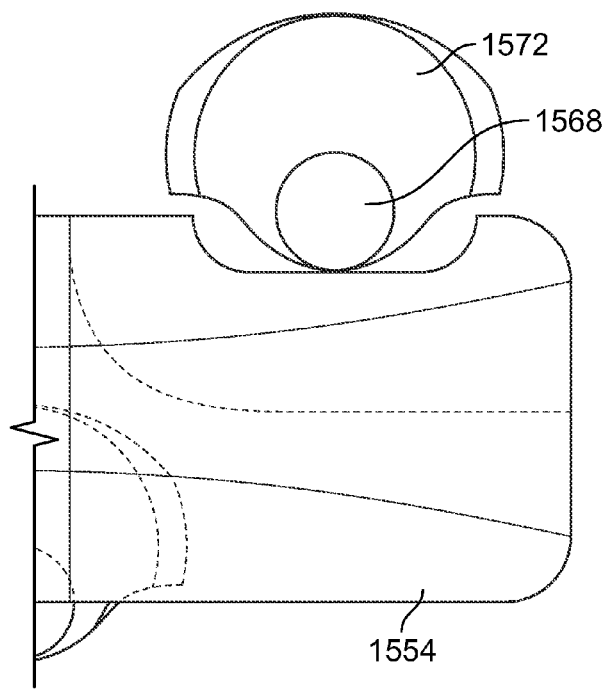

In FIG. 81, a cam shaft 1567 is shown from a posterior viewpoint in its initial position resting in the groove 1556 of the trial spacer member 1554. The head of the cam shaft is engaged by the drive tool 1570 having an eccentric cam 1573 (FIG. 87) for camming against an anterior platform or ledge 1555 (FIGS. 77 and 79) on the trial spacer member 1554. The cam shafts 1567 are cammed at both their distal shaft ends 1568 as shown in FIGS. 81-85 and 87, as well as at their proximate ends where they interface with drive tool 1570. In FIG. 82, the drive tool 1570 has been rotated clockwise 90 degrees along the anterior platform 1555 of the trial spacer member 1554. This causes the cam shaft 1567 to rotate 90 degrees and the cam lobes 1572 begin to engage and imbed themselves the upper vertebra. In FIG. 83, the cam shaft 1567 is shown fully rotated 180 degrees from its initial position in FIG. 81. At this point, the cam lobes 1572 are embedded into the vertebra, and are held in place due to the frictional engagement between the cam lobes 1572 and the bone. Finally, the driver 1570 may be removed, as is shown in FIG. 84. Once the cam shafts 1567 have been fully rotated 180 degrees, the cam lobes 1572 are completely removed from the body of the trial spacer member 1554. Thus, the trial spacer 1554 may be removed.

With the cam shafts 1567 rotated as shown in FIG. 84 so that the sharp cam lobes 1572 thereof are rotated up (or down) into the vertebral bodies via a cutting action generated by the cams during such rotation, the disc implant 1552 is then inserted into the intervertebral space 1330. As shown in FIG. 85, the upper disc member 1564 has spiral cutouts 1566 in the upper surface thereof so that rotating the cam shafts 1562 again causes the cam lobes 1572 to be engaged in both the grooves of the vertebral bodies 1332 and 1334 as well as tightly engaged or embedded into the raised ribs 1571 defining the spiral cutouts 1566 so that the implant 1552 is securely held and retained in the intervertebral space 1330 during articulation thereof.

Figure 88:
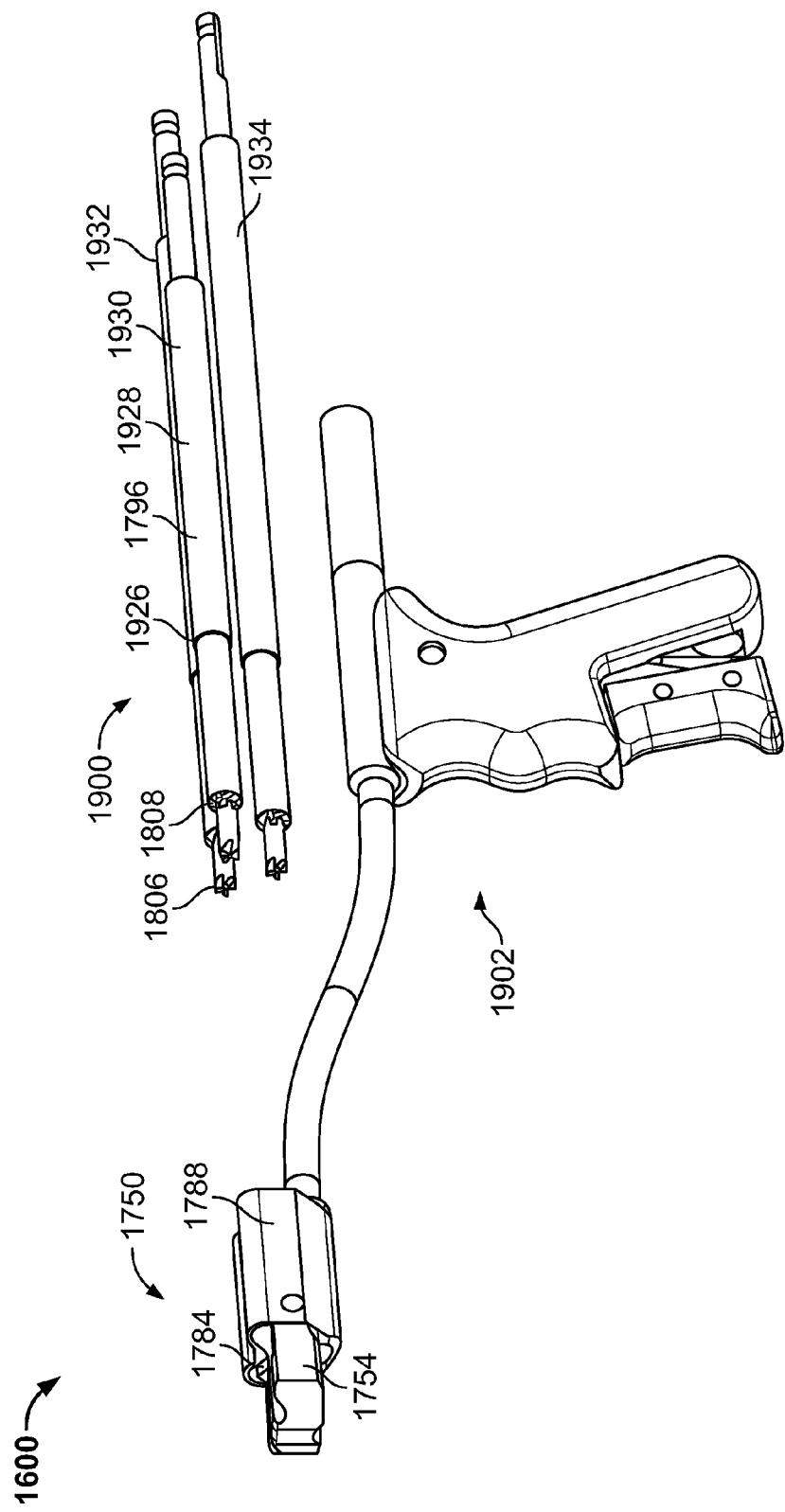
FIG. 88 is a side perspective view of the trial spacer system comprised of a trial spacer assembly, a drill set, and a trial spacer inserter tool.

In another form, a trial spacer system 1600 is shown in FIG. 88 is employed for sizing and preparing an implantation site for an implant. The trial spacer system 1600 includes a trial spacer assembly 1750, a drill set 1900, and an insertion tool 1902. As in the embodiment disclosed in FIG. 56, the trial spacer assembly 1750 is utilized to form features in the vertebral bodies 1330, 1332 for receipt of the securing mechanism that is associated with the artificial disc implant 1752. A principal difference between the trial spacer assembly 1450 of FIG. 56 and the present trial spacer assembly 1750 is that present assembly eliminates the shaft portion 1462 and integrates the drill guide 1488 together with the trial spacer portion 1454. Additional features that vary from the previous embodiment of the trial spacer assembly 1450, including the insertion tool 1902, will be described below.

Figure 89:
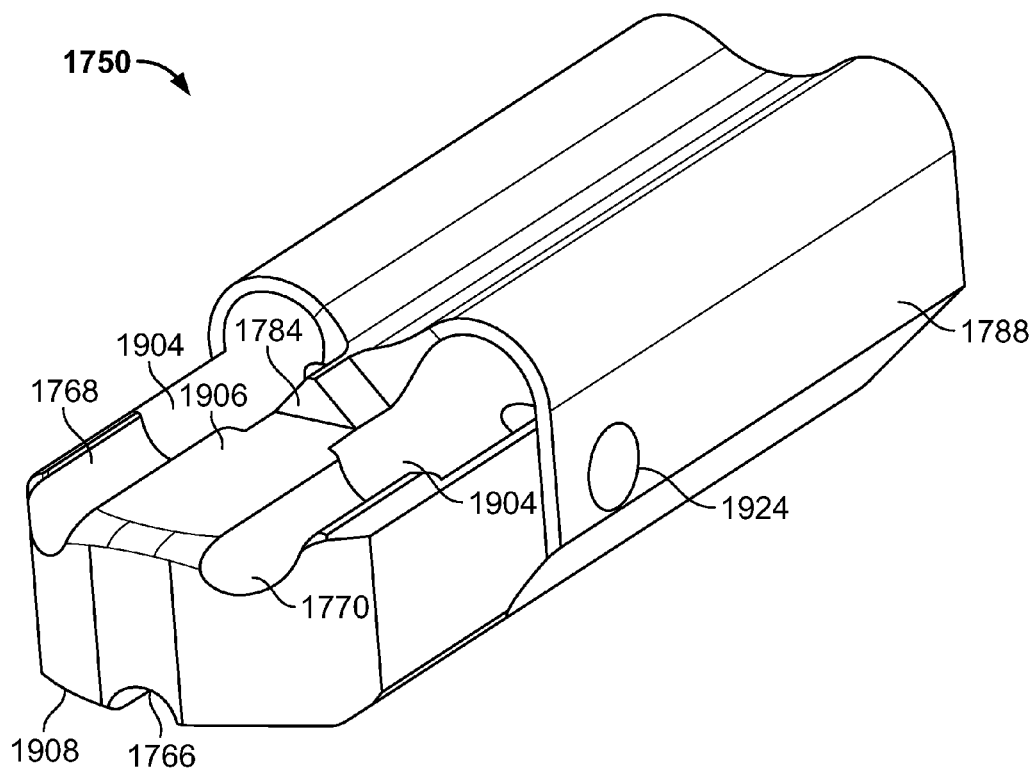
FIG. 89 is a posterolateral perspective view of the trial spacer assembly of FIG. 88.

The trial spacer assembly 1750 generally has a forward trial spacer portion 1754 for insertion into the intervertebral space 1330 and rearward drill guide 1788 integrated with the forward trial spacer portion 1754. The forward trial spacer portion 1754 varies little from the previously described embodiment in FIG. 56, and therefore will not be described in full detail here. However, one feature notably different in geometry from the previous embodiment is the upper stop member 1784, shown in FIG. 89 located on the upper surface of the trial spacer portion between the upper grooves 1768, 1770. In addition, both the upper grooves 1768, 1770 and the lower groove 1766 have a rearward counterbored portion 1904 for accommodating drill bits 1930, 1932, 1934 having a forward cutting portion 1806 and a rearward counterbored portion 1808. Also, the upper and lower faces 1906, 1908 of the trial spacer portion 1754 may be skewed with respect to one another to mimic the lordotic angle of the spine to improve the fit of the trial spacer 1754. Preferably, the angle between the upper and lower faces 1906, 1908 is about 5 degrees. The trial spacer assembly 1750 is preferably made with titanium or stainless steel. In addition, the assembly is preferably colorized using an anodization process, such that different sized trial spacer assemblies are color coded for ease of identification.

Figure 90:
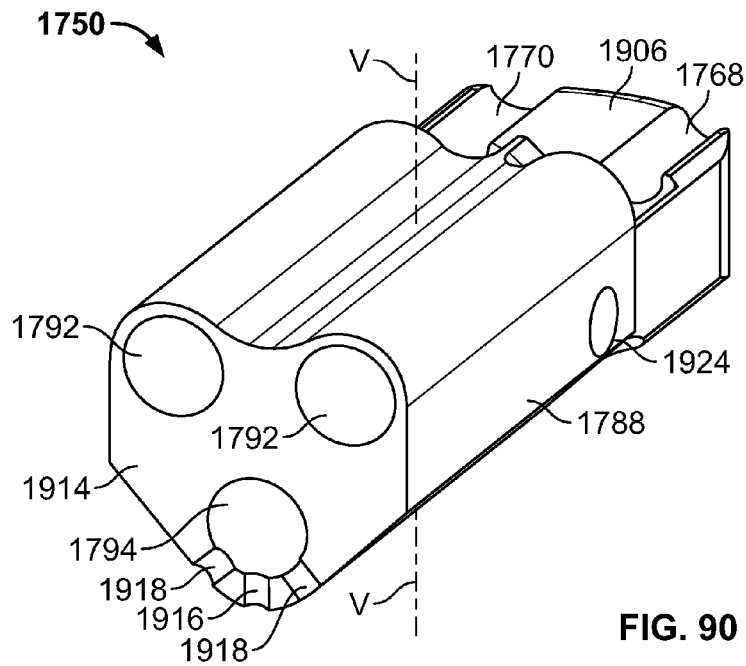
FIG. 90 is an anterolateral perspective view of the trial spacer assembly of FIG. 88.
Figure 91:
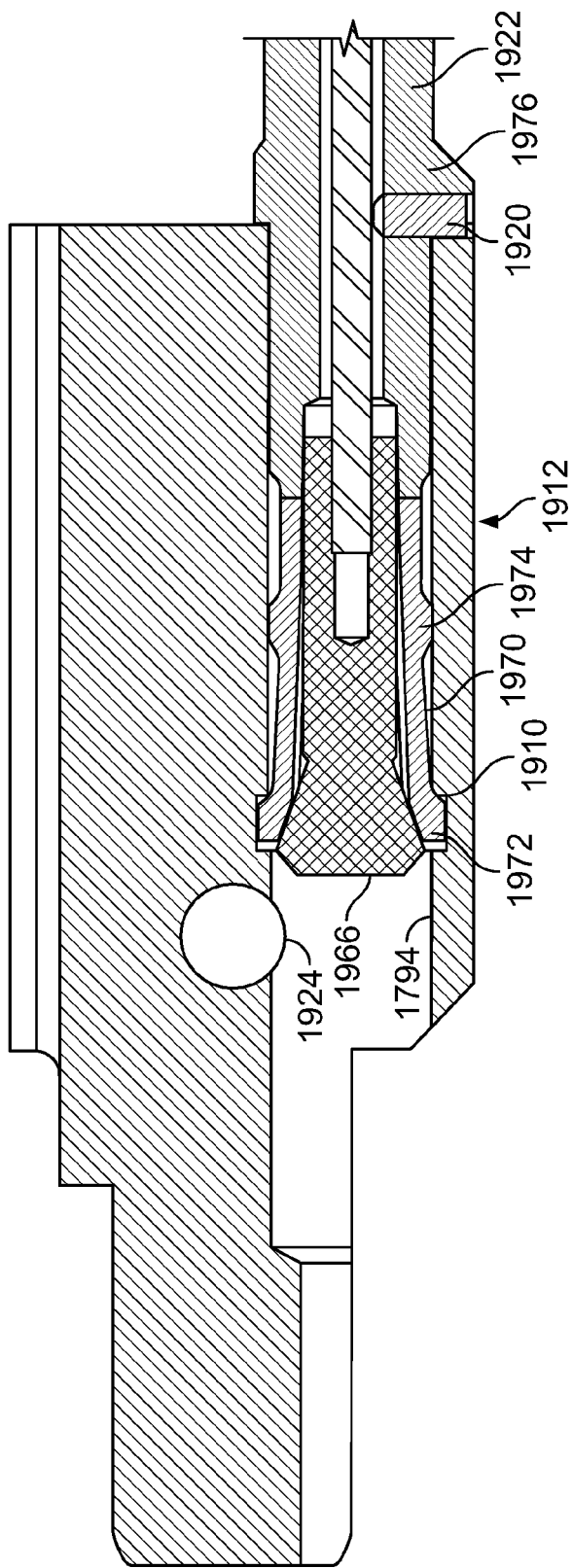
FIG. 91 is an enlarged longitudinal cross-sectional view of the trial spacer assembly of FIG. 88 with the gripping mechanism of the inserter tool inserted therein.

The drill guide portion 1788 of the of the trial spacer assembly 1750 is similar from the drill guide 1488 of FIG. 64, except for a few notable features. For instance, the present drill guide portion 1788 replaces the irregularly-shaped throughbore 1494 with a lower throughbore 1794 similar in diameter to the upper throughbores 1792, as shown in FIG. 90. As shown in FIG. 91, the lower throughbore 1794 has an annular recessed portion 1910 for accepting the gripping mechanism 1912 of the insertion tool 1902 to allow the tool 1902 to securely attach to the trial spacer assembly 1750. Now referring to FIG. 90, the drill guide portion 1788 has a rear face 1914 wherein each throughbore 1792, 1794 terminates. On the face 1914 adjacent to the lower throughbore 1794 are a set of three recesses 1916, 1918 for providing three positions at which the inserter tool 1902 may engage the trial spacer assembly 1750. Each recess 1916, 1918 is sized to mate with a single corresponding guide pin 1920 on the barrel 1922 of the inserter tool 1902. When the middle recess 1916 is engaged by the pin 1920 of the inserter tool 1902 (as in FIG. 91), the trial spacer assembly 1750 is held at a neutral angle, with the vertical axis (denoted with a "v") of the assembly parallel with the vertical axis of the inserter tool 1902. The two remaining recesses 1918 to either side of the middle recess 1916 allow the user to grip the trial spacer assembly 1750 at 45 or −45 degrees with respect to the vertical axis. This allows the surgeon to manipulate the trial spacer 1750 in multiple positions, and gives the tool 1902 greater flexibility. Accordingly, the tool 1902 has a plurality of relative positions between the tool barrel 1922 and the trial spacer assembly 1750. The drill guide portion 1788 also defines a lateral bore 1924 for providing a point of reference for the surgeon when viewing the trial spacer 1750 using fluoroscopy to help position the assembly 1750 once inserted into the patient's body. A bore 1924 is used because the trial spacer assembly 1750 is preferably made out of stainless steel or titanium.

Now referring to FIG. 88, each drill bit 1930, 1932, 1934 of the set 1900 has identical cutting surfaces 1806, 1808 on the forward end of the shaft 1928. The forward cutting portion 1806 consists of a cutting surface at the tip of the bit 1796 suitable for cutting an elongate groove 1498 in the vertebra 1332, 1334 for the forward portion of the securing mechanism of the implant 1752. At the rear end of the first cutting portion 1806 begins the counterbore cutting portion 1808 for creating a counterbore in the vertebra to provide clearance for the head of the securing mechanism.

Each drill bit 1796 has a collar 1926 for providing an abutment surface to restrict the distance the bit 1796 may be inserted into the trial spacer assembly 1750. The collar 1926 is an enlarged portion of the drill bit shaft 1928 and abuts the rear face 1914 of the trial spacer assembly 1750 when the drill bit 1796 is fully inserted. This keeps the surgeon from unintentionally drilling too far and damaging surrounding tissue, bone, nerves, and other vital areas.

As shown in FIG. 88, the drill set 1900 is comprised of three drill bits 1930, 1932, 1934 having shafts 1928 of differing lengths. The length of each shaft 1928 is different so the bits 1930-34 may be left in the drill guide 1788 and used sequentially, from shortest to longest, without interfering with the drill. The first and shortest bit 1930 is used to create the first groove 1798 in the upper vertebra 1332, the second and intermediate bit 1932 to create the second groove 1798 in the upper vertebra 1332, and the third and longest bit 1934 to create the groove 1800 in the lower vertebra 1334. This way, the first and second drill bits 1930, 1932 need not be removed from the trial spacer assembly 1750 prior to insertion of the third drill bit 1934. Once the first and second drills have cut grooves 1798 into the upper vertebra 1332, they remain in place to act as placeholders in the newly formed grooves 1798. In this manner, the drill bits 1900 help to secure the trial spacer 1750 in place to prevent movement of the trial spacer assembly 1750 with respect to the vertebrae 1332, 1334 while the other grooves are being cut and while the inserter tool 1902 is being removed. Advantageously, no other fixation means, such as bone screws, are necessary to secure the trial spacer 1750 to the vertebrae 1332, 1334.

Figure 92:
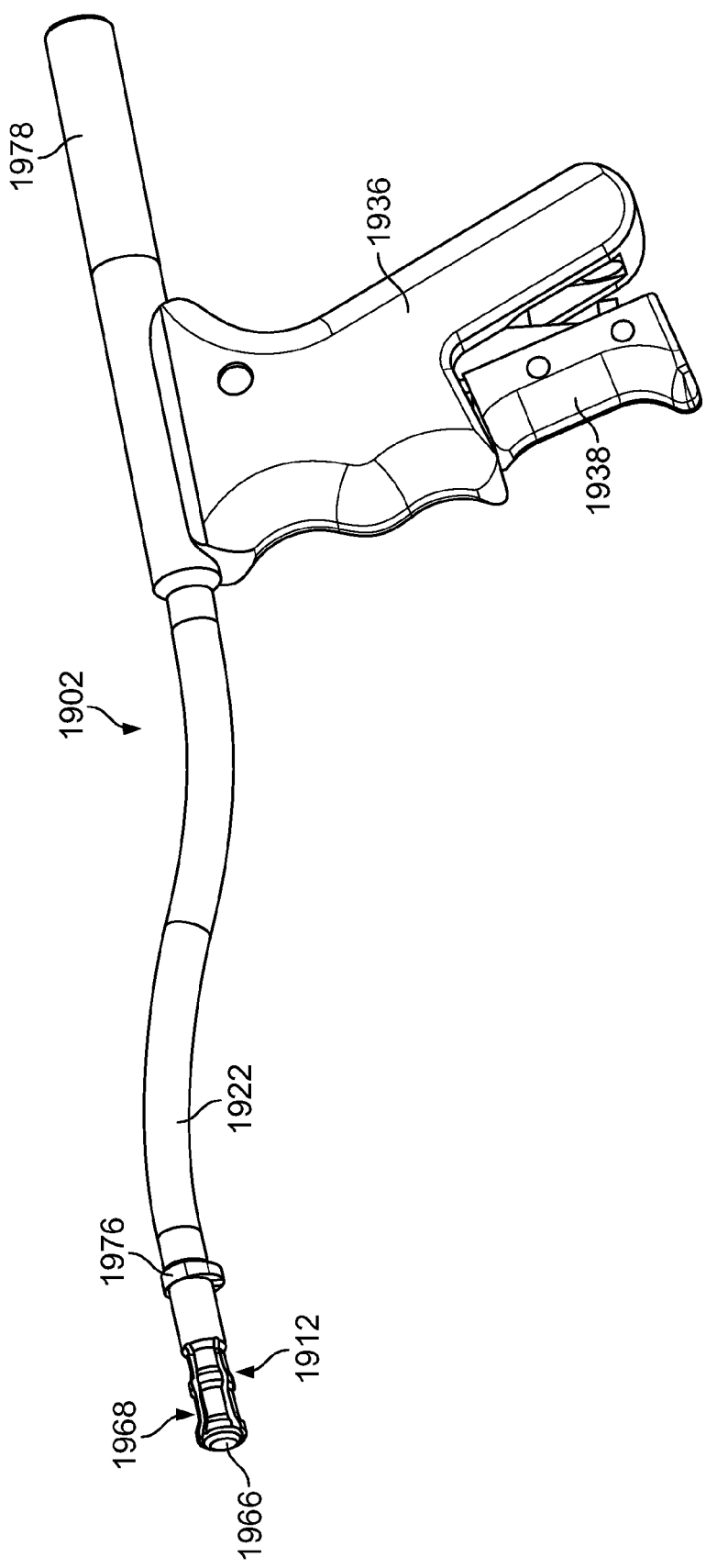
FIG. 92 is a side perspective view of the inserter tool of FIG. 88.
Figure 93:
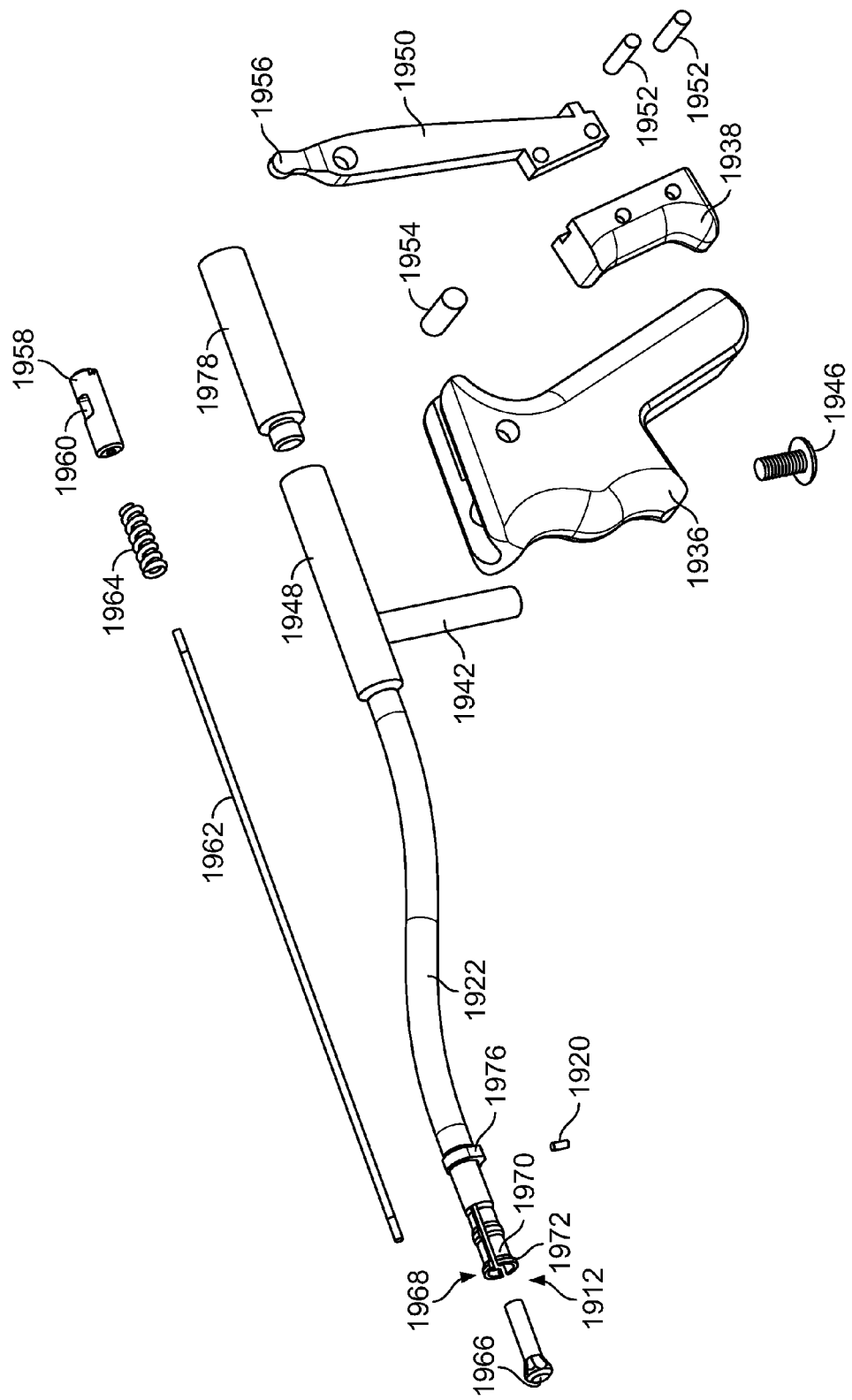
FIG. 93 is an exploded view of the inserter tool of FIG. 88.
Figure 94:
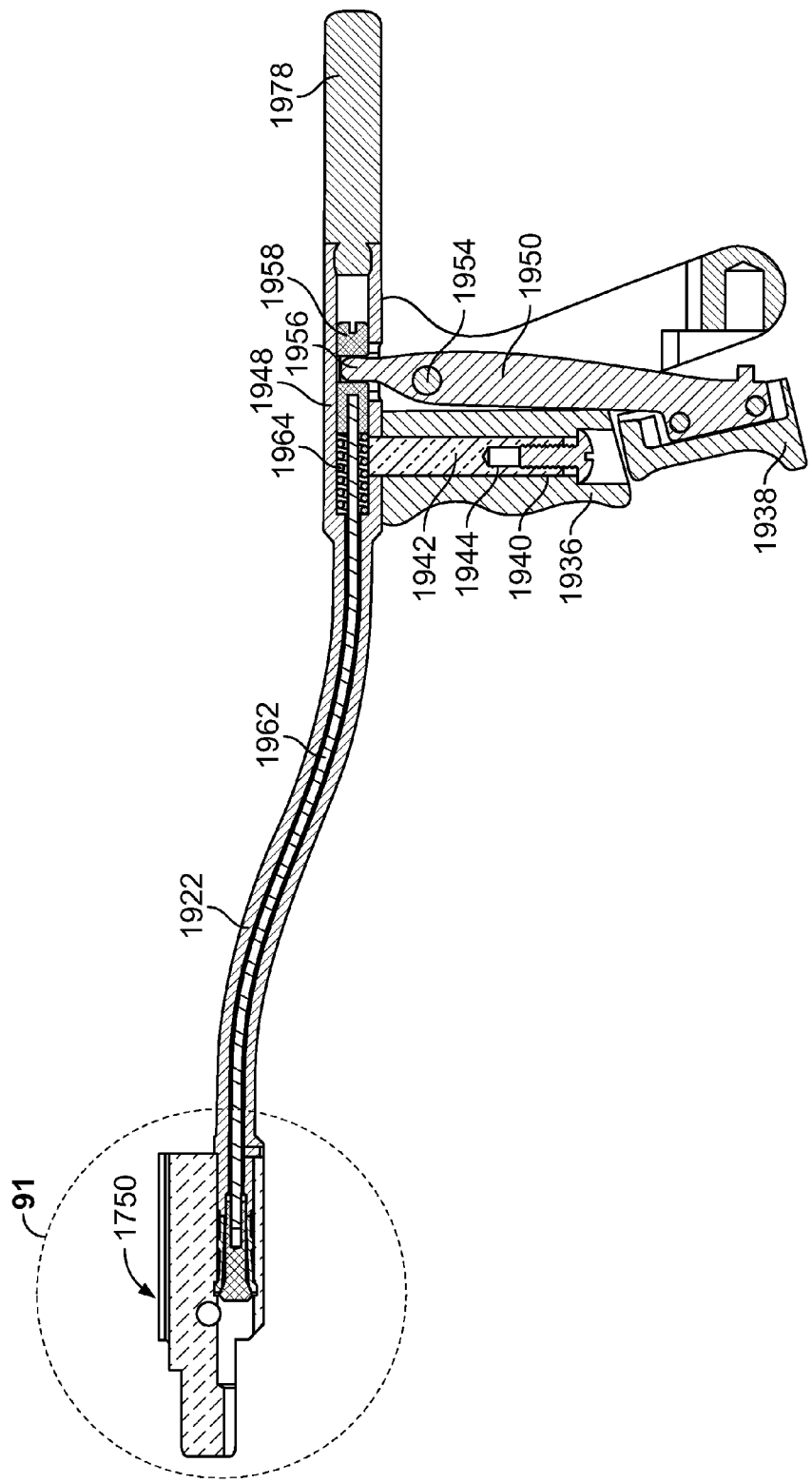
FIG. 94 is a longitudinal cross-sectional view of the inserter tool and trial spacer assembly of FIG. 88.
Figure 95:
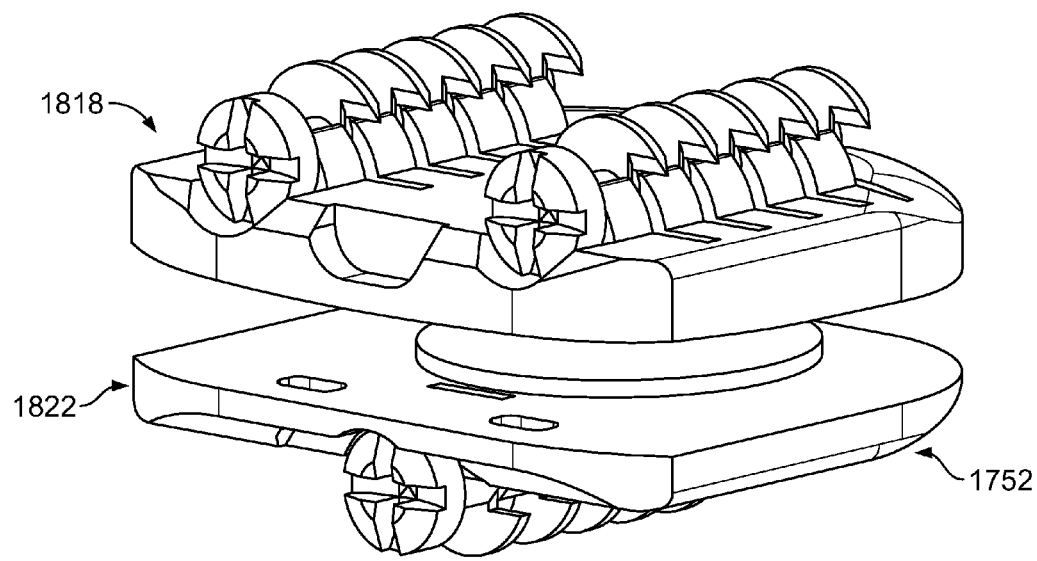
FIG. 95 is an anterolateral perspective view of an artificial disc implant according to the present invention with the securing mechanisms fully deployed.

Now referring FIG. 92, the trial spacer inserter 1902 comprises a gripping assembly 1912 connected by a barrel 1922 to a handle 1936 and an actuator in the form of a trigger 1938. As shown in FIGS. 93 and 94, the handle 1936, preferably made of a polymer, such as Radel®, has a partially hollow interior including an annular recess 1940 for accepting a downwardly extending handle shaft 1942 having a threaded recess 1944 at the bottom. A fastener 1946 affixes the handle 1936 to the downwardly extending handle shaft 1942 by threading the fastener 1946 into the threaded end 1944. The handle shaft 1942 is welded or otherwise integrated into the yoke housing 1948 of the inserter 1902. The trigger 1938 is attached to an elongate trigger link 1950 at the link's lower end with two pins 1952. The trigger link 1950 is disposed partially within the interior of the handle 1936 and pivots about a hinge pin 1954 which protrudes through the trigger link 1950 and is captured within the handle 1936. At its upper end, the trigger link 1950 has an actuating head portion 1956 for actuating the gripping mechanism 1912.

Specifically, the head portion 1956 of the trigger link 1950 directly engages the yoke 1958 to move it within the yoke housing 1948 to actuate the gripping mechanism. The yoke 1958 is a cylindrical body having a bore 1960 for accepting the head portion 1956 of the trigger link 1950 and is directly propelled thereby. The yoke 1958 is attached to the push rod 1962 at the rear portion of the yoke's forward end. A spring 1964 disposed between the yoke 1958 and the internal end wall of the yoke housing 1948 provides a biased resistance to the trigger 1938 when the yoke 1958 is actuated by the trigger link 1950.

The yoke housing 1948 is connected to the barrel 1922, which defines an internal bore 1960 for guiding the push rod 1962 through the barrel 1922. The push rod 1962 is preferably made of a flexible material, such as Nitinol. The push rod 1962 extends through the internal bore 1960 within the barrel 1922 from the yoke 1958 to the gripping mechanism 1912. The gripping mechanism 1912 includes a wedge shaped plunger 1966 connected to the push rod 1962 and an expandable flared end 1968. The flared end 1968 has a plurality of flexible tabs 1970 each having a protrusion 1972 at the forward end of the tab 1970 for engaging the recessed portion 1910 within the lower throughbore 1794 of the trial spacer assembly 1750 as shown in FIG. 91. The tabs 1970 also have a stabilizing ridge 1974 for engaging the internal surface of the lower throughbore 1974 to further stabilize the trial spacer assembly 1750 to prevent unwanted movement between the assembly 1750 and the inserter tool 1902. The flared end 1968 is sized to fit within the lower throughbore 1794 when the plunger 1966 is not retracted. The flexible tabs 1970 are splayed radially outwards by the wedge-shaped plunger 1966 when the plunger 1966 is pulled inwards towards the rear. When the plunger 1966 is retracted, the flexible tabs 1970 engage the internal surfaces of the lower throughbore 1794.

The barrel 1922 includes an insertion guide 1976 disposed on the barrel 1922 near the gripping mechanism 1912 for abutting the rear face 1914 of the drill guide portion 1788 to prevent inserting the barrel 1922 too far into the lower throughbore 1794. In addition, the insertion guide 1976 comprises a guide pin 1920 as described above for engaging the recesses 1916, 1918 in the rear face 1914 of the drill guide portion 1788 to increase maneuverability and stability of the trial spacer assembly 1750.

A solid cylindrical end cap 1978 at the rear end of the tool 1902 is connected to the yoke housing 1948 to provide a contact surface for the surgeon to strike during insertion of the trial spacer assembly 1750.

Figure 69:
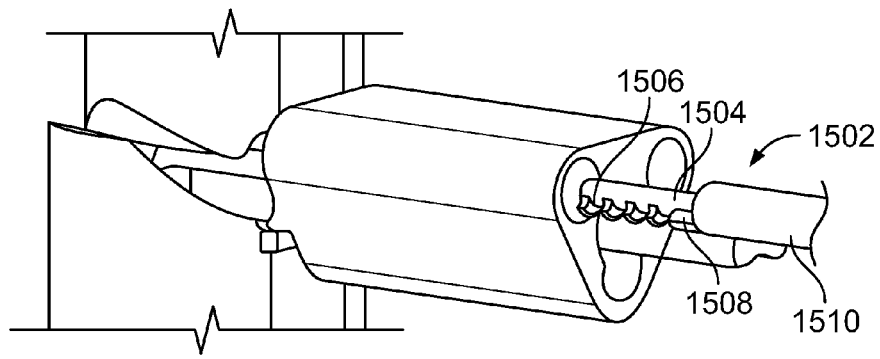
FIG. 69 is an anterolateral perspective view of the trial spacer of FIG. 68 with the cam cutter guide slid over the shaft and a cam cutter prior to cutting cams into the vertebrae.
Figure 71:
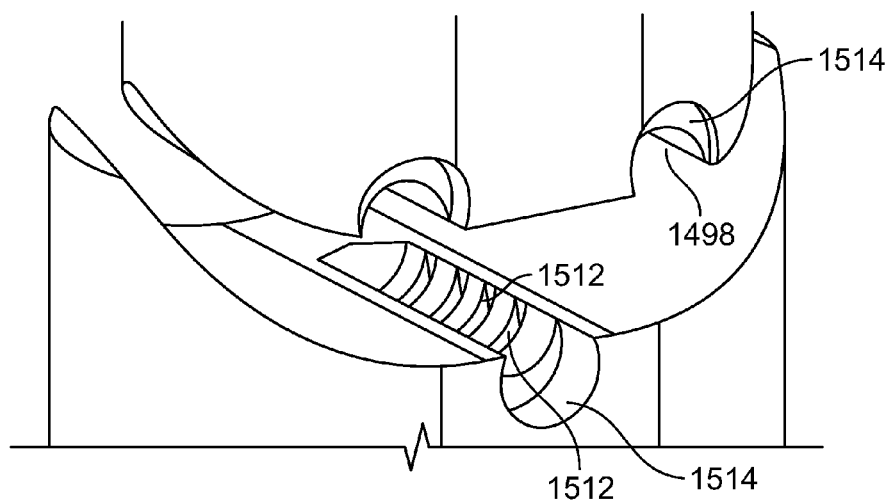
FIG. 71 is an anterolateral perspective view of the intervertebral space after the grooves and cams have been cut by the drill and the cam cutter.

In operation, the gripping mechanism 1912 is inserted into the lower throughbore 1794 of the trial spacer assembly 1750 with the trigger 1938 depressed to push the plunger 1966 forward to disengage the flexible tabs 1970 of the gripping mechanism 1912. Once the inserter end is fully inserted into the trial spacer assembly 1750, the trigger 1938 is released, causing the plunger 1966 to be pulled back and splaying the flexible tabs radially outward. The flexible tabs 1970 are forced into gripping engagement with the internal surfaces of the lower throughbore 1794, and the guiding pin 1920 engages one of the recesses 1916, 1918 in the rear face 1914 of the drill guide portion 1788 for providing additional stability and control. The trial spacer 1750 is then inserted into the intervertebral space 1330. If the spacer 1750 is the appropriate size, the surgeon will then prepare the vertebrae 1332, 1334 for the implant 1752. While continuing to hold the trial spacer assembly 1750 in place with the trial spacer inserter 1902, the first drill bit 1930 is affixed to the drill, and then inserted into one of the upper throughbores 1792 of the trial spacer assembly 1750. The first groove 1798 is drilled. While the drill bit 1930 is still fully within the trial spacer assembly 1750, the drill bit 1930 is released from the drill and left in place. Next, the second intermediate drill bit 1932 is attached to the drill and the second upper groove 1798 is then drilled. Again, the second drill bit 1932 is left in place. The inserter 1902 is then removed from the trial spacer assembly 1750. This is done by pulling the trigger 1938 to disengage the gripping mechanism 1912 and pulling the inserter 1902 away. The inserter tool 1902 is then removed and the lower groove 1800 is drilled, using the third and longest drill bit 1934. Once all of the grooves have been drilled, all three of the drill bits 1930-34 are removed by hand. In a preferred embodiment, the cam cutting step described in FIGS. 69-71 is omitted because the artificial disc implant 1752 is provided with cutting-type cams 1846 as previously described. Then, to remove the trial spacer assembly 1750, the insertion tool 1902 is reinserted into the lower throughbore 1794, the trigger 1938 is released to grip the trial spacer assembly 1750, and the assembly 1750 is pulled out using the insertion tool 1902. The surgical site is then preferably irrigated in preparation for insertion of the implant 1752.

The artificial disc implant 1752 of the present embodiment varies in only a few respects compared with the artificial disc implant shown in FIGS. 72-76. For instance, the present embodiment has a different form of disc indicator member 232. The following embodiments provide tactile feedback regarding the position of the securing mechanism to the surgeon as the securing mechanism is deployed. Because the bone is relatively soft compared to the projections being deployed into the bone, the bone provides little resistance to the projections as they are deployed into the bone. Therefore, it is important to provide the surgeon with tactile feedback so that he does not over or under deploy the projections, causing the implant 1752 to be improperly affixed to the bone. In addition, it is important to provide the securing mechanism with positive retraction blocking structure. Because the vertebral bone provides only a limited amount of resistance to the deployable projections, the projections may be prone to retract, derotate, or otherwise begin to return to their original undeployed position over time. Thus, retraction blocking structures are provided on the disc implant 1752 to avoid this condition.

Figure 96:
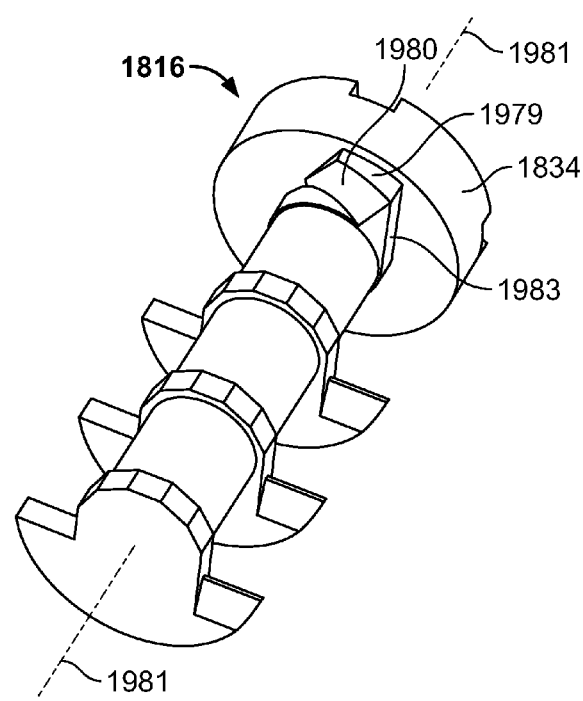
FIG. 96 is a posterolateral perspective view of a cam shaft securing mechanism according to the present invention illustrating a camming surface.
Figure 97:
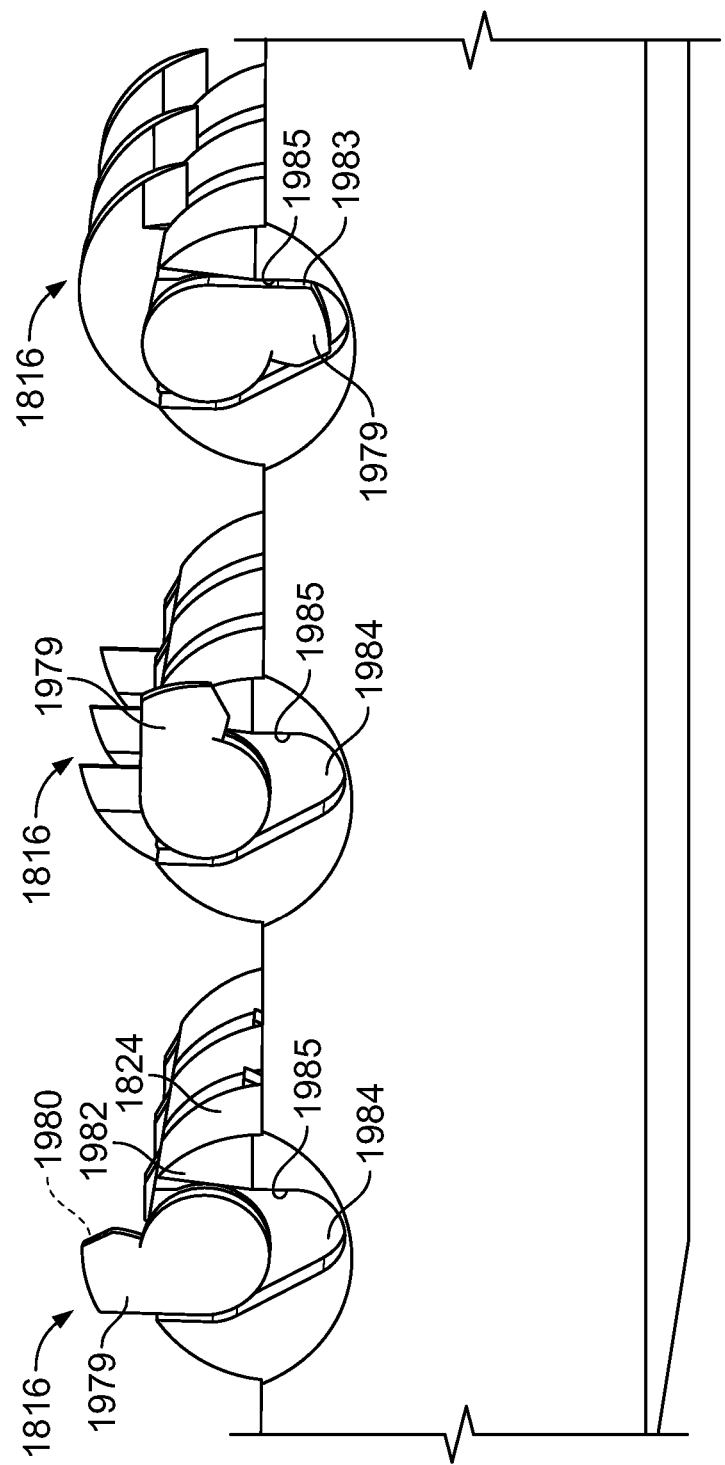
FIG. 97 is an anterolateral perspective view of the cam shaft of FIG. 96 with the head hidden disposed in a test block mimicking a securing mechanism for an implant for illustration of the operation of the cam shaft. The cam shaft is shown in an undeployed position, a partially deployed position, and fully deployed, from left to right.

The securing mechanism may take many forms. In one embodiment according to FIG. 96, the securing mechanism takes the form of a cam shaft 1816. The cam shaft 1816 has a radially extending cam projection 1979 including a tactile feedback creating surface in the form of a wedge-shaped camming surface 1980 adjacent the drive head 1834. The camming surface 1980 frictionally engages a corresponding camming surface 1982 disposed on the adjacent retainer member 1824 shown in FIG. 97 (in a test block for demonstrative purposes with heads 1834 of the cam shafts 1816 hidden) as the cam shaft 1816 is rotated from its undeployed starting position (on left side of FIG. 97), to a partially deployed position, and then to its fully deployed position 180 degrees from its starting position. The camming surfaces 1980 and 1982 are inclined relative to the longitudinal axis 1981 so that as the camming surfaces 1980, 1982 engage and cam against each other, the cam shaft 1816 is shifted axially towards the anterior direction (as installed in the spine).

This frictional interaction between the camming surfaces 1980, 1982 and a biasing force exerted by the retainer members 1824 on the cam shaft 1816 caused by the deformation of the retainer members 1824 provides tactile feedback to the surgeon. The deformation of the retainer members is preferably elastic, such that the retainer members 1824 will return to their original shape when the cam shaft 1816 is in its fully deployed position. Alternatively, the deformation could be plastic, wherein the retainer members 1824 undergo some irreversible deformation. This is acceptable when the securing mechanism is not deployed and retracted repeatedly.

Once the cam shaft 1816 is turned a full 180 degrees, the cam shaft camming surface 1980 snaps into a recess 1984 formed in the adjacent retainer member 1824, due to the biasing force exerted on the cam shaft 1816 by the flexed retainer members 1824. The recess 1984 and cam shaft camming surface 1980 is formed such that the camming surface 1980 becomes trapped in the recess 1984 and blocks derotation of the cam shaft 1816. More specifically, the cam projection 1979 has a straight, trailing edge surface 1983 that is turned toward the straight edge surface 1985 of recess 1984. Once the trailing edge surface 1983 clears the recess surface 1985, the cam surface 1980 will have traveled past the corresponding camming surface 1982 so that the cam surfaces 1980 and 1982 are disengaged from one another. This removes the axial biasing force that their camming engagement generates, so that the cam projection 1979 travels or snaps axially back into the recess 1984. In this orientation, the flat edge surfaces are in confronting relation to each other so that the cam projection 1979 can not be moved back out of the recess 1984.

Figure 98:
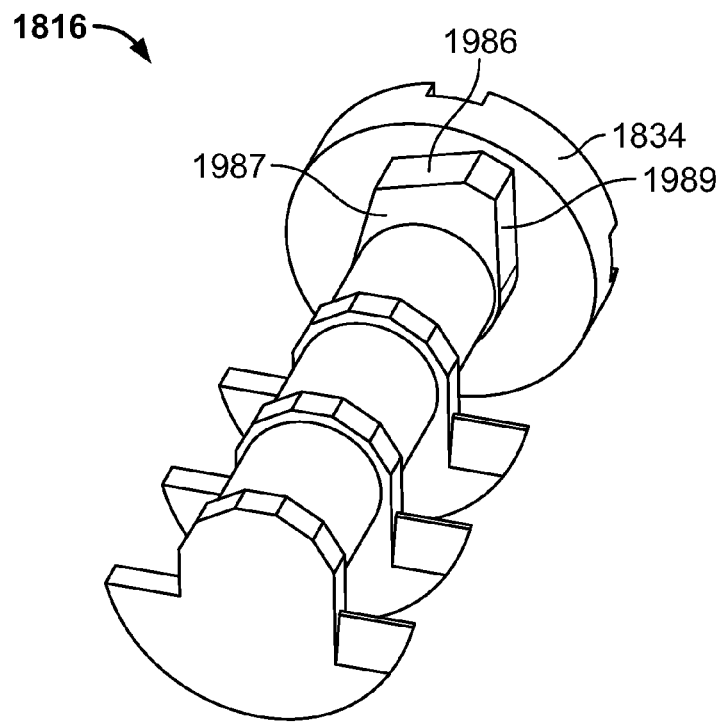
FIG. 98 is a posterolateral perspective view of a cam shaft securing mechanism according to the present invention illustrating a flat camming surface.
Figure 99:
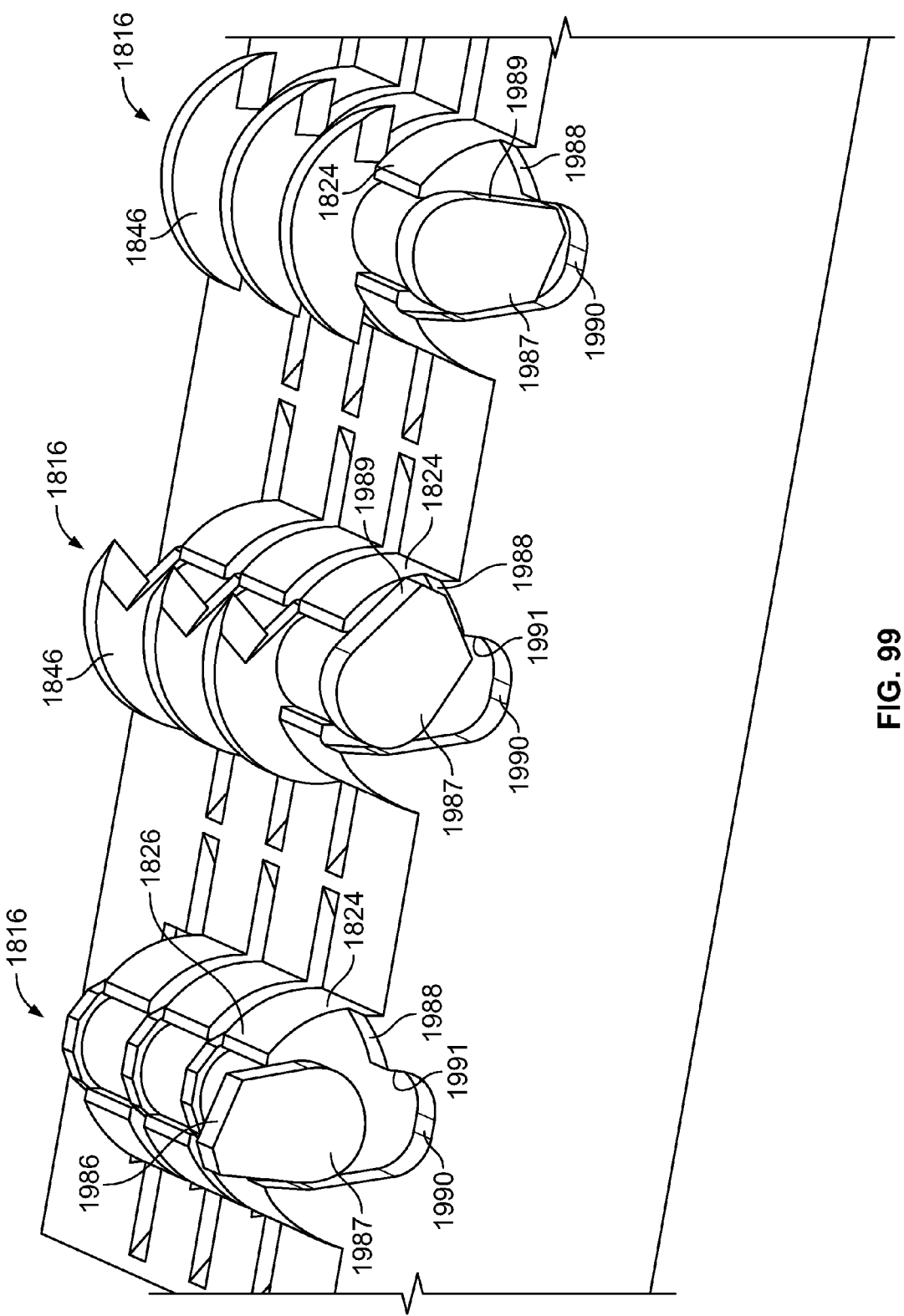
FIG. 99 is an anterolateral perspective view of the cam shaft of FIG. 98 with the head hidden disposed in a test block mimicking a securing mechanism for an implant for illustration of the operation of the cam shaft. The cam shaft is shown in an undeployed position, a partially deployed position, and fully deployed, from left to right.

Now referring to FIGS. 98 and 99, another embodiment of the securing mechanism for providing tactile feedback to the surgeon and preventing retraction of the securing mechanism is disclosed. The cam shaft 1816 has a flat camming surface 1986 adjacent the drive head 1834. As shown in FIG. 99 (in a test block arrangement similar to FIG. 97), the flat camming surface 1986 frictionally engages a corresponding camming surface 1988 formed in the adjacent retainer member 1824. The camming surfaces 1986, 1988 operate similarly to the wedge shape camming surface 1980 and corresponding camming surface 1982, except that instead of biasing the cam shaft 1816 axially, they bias the cam shaft 1816 generally vertically. As the cam shaft 1816 is rotated from its starting position to the fully deployed position (at 180 degrees from its undeployed starting position), the flat camming surface 1986 of the cam shaft 1816 engages the corresponding camming surface 1988 of the retainer member 1824. This pushes the cam shaft 1816 generally upward away from the retainer members 1824, which biases the cam shaft 1816 against the upwardly extending arm 1826 of the retaining members 1824, providing tactile feedback to the surgeon in the form of increased resistance to the rotation of the cam shaft 1816 until the shaft is almost turned a full 180 degrees. The resistance dissipates quickly as the camming surfaces begin to disengage each other. In fact, the deformation of the retaining members 1824 may help to propel the cam shaft into a fully deployed position. This propulsion and dissipation of resistance constitutes additional tactile feedback which varies during the deployment of the securing mechanism and informs the surgeon that the cam members 1846 are fully deployed. Once the cam shaft 1816 is turned a full 180 degrees, the flat camming surface 1986 snaps into a recess 1990 formed in the adjacent retainer member 1824, due to the generally vertical biasing force exerted by the flexed retainer members 1824. The recess 1990 and cam shaft camming surface 1986 are formed such that the camming surface 1986 becomes trapped in the recess 1990 and prevents derotation of the cam shaft 1816.

More specifically, the cam projection 1987 has a straight, trailing edge surface 1989 that is turned toward the straight edge surface 1991 of recess 1990. Once the trailing edge surface 1989 clears the recess surface 1991, the cam surface 1986 will have traveled past the corresponding camming surface 1988 so that the cam surfaces 1986 and 1988 are disengaged from one another. This removes the vertical biasing force that their camming engagement generates, so that the cam projection 1987 travels or snaps axially down into the recess 1990. In this orientation, the straight edge surfaces 1989, 1991 are in confronting relation to each other so that the cam projection 1987 can not be moved back out of the recess 1990.

Figure 100:
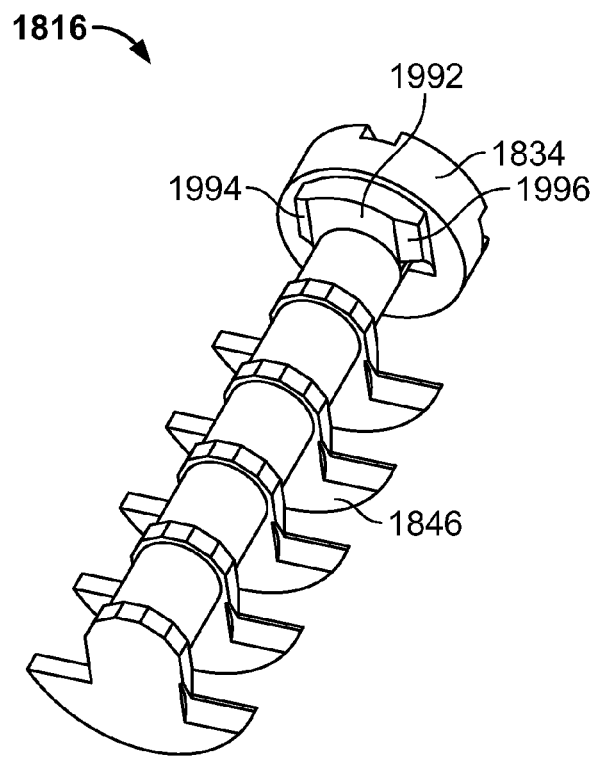
FIG. 100 is a posterolateral perspective view of a cam shaft securing mechanism according to the present invention illustrating a dual chamfered camming surface.
Figure 101:
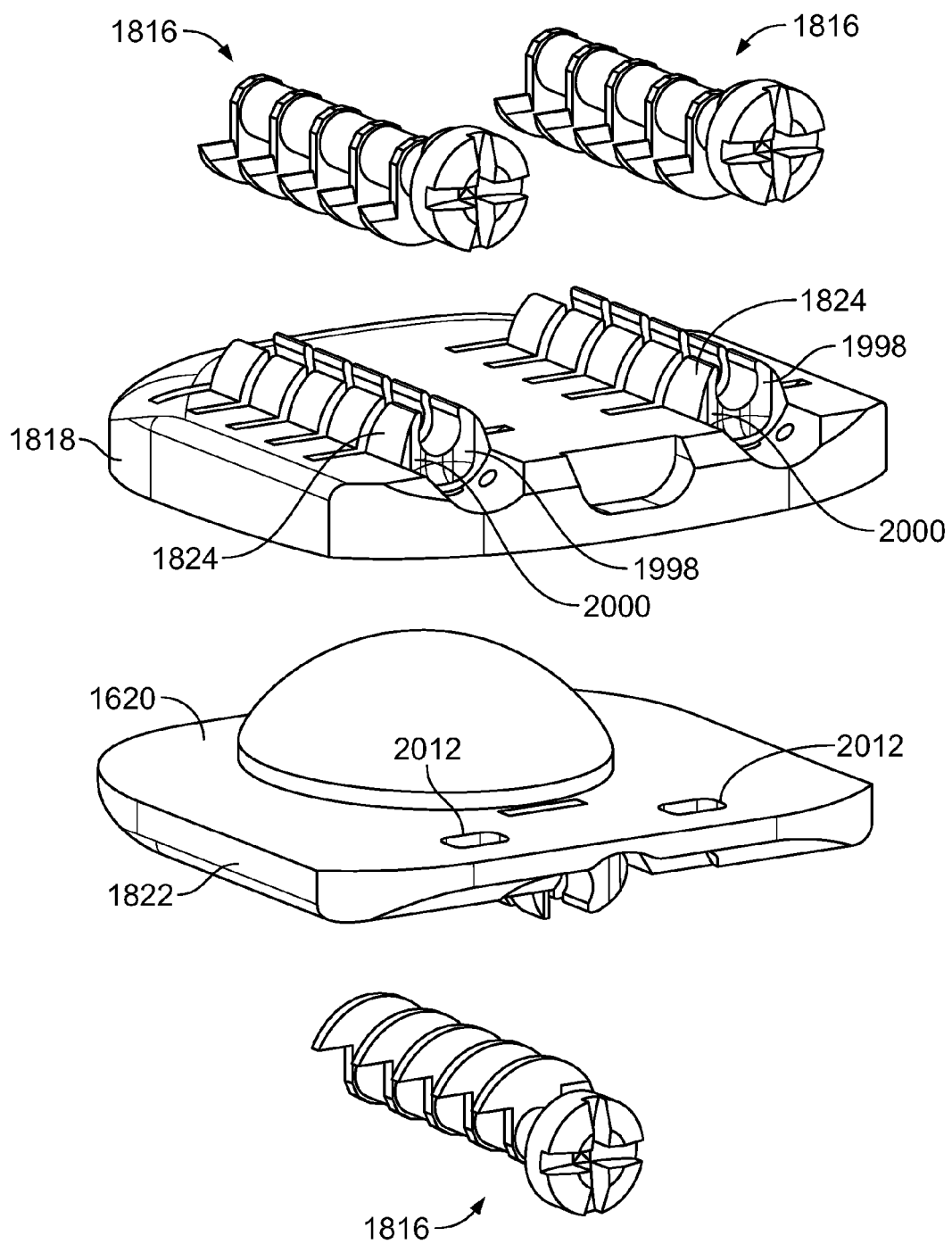
FIG. 101 is an anterolateral exploded view of the artificial disc implant of FIG. 95.

In another form shown in FIGS. 100 and 101, the cam shaft 1816 has a dual chamfered camming surface 1992 for providing tactile feedback to the surgeon and preventing derotation of the cam shaft 1816. In this embodiment, a chamfered surface 1994 for providing resistive feedback during deployment of the cam lobes 1846 is provided on one side of the camming surface 1992, which is engaged when the cam shaft 1816 is rotated in a clockwise direction. Another chamfered surface 1996 is provided on the other side of the camming surface 1992 for providing resistive feedback during retraction of the cam lobes 1846, which is engaged when the cam shaft 1816 is rotated in a counterclockwise direction. Like the embodiments described directly above, the camming surface 1992 engages a corresponding generally concave camming surface 1998 formed in the adjacent retainer member 1824. The corresponding camming surface 1998 is formed such that the chamfered camming surface 1992 adjacent the drive head engages the corresponding camming surface 1998 causing the cam shaft 1816 to bias against the retainer members 1824 and provide tactile or resistive feedback as described above. Unlike the embodiments above, the cam 1816 may be manually retracted by turning the cam shaft 1816 back 180 degrees in the counterclockwise direction. This is desirable if the surgeon wishes to adjust the implant 1752 or prepare the implantation site further. Over-rotation and rotation in the wrong direction is prevented by leaving a raised surface 2000 on the opposite side of the corresponding camming surface 1998 such that it is virtually impossible to turn the cam shaft 1816 in the wrong direction due to interference between the camming surface 1992 on the cam 1816 and the raised surface 2000.

Figure 102:
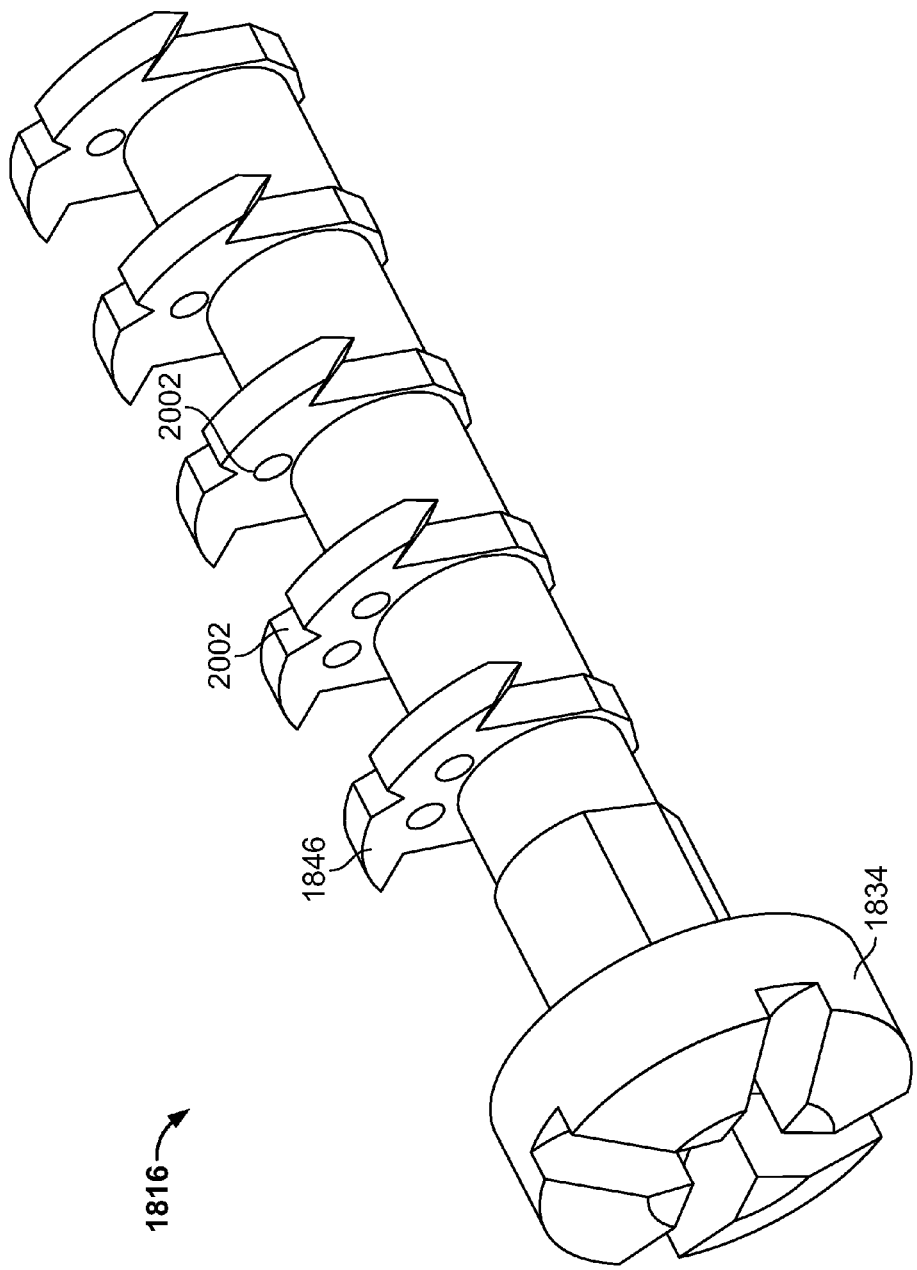
FIG. 102 is an anterolateral perspective view of an alternate embodiment of a cam shaft securing mechanism according to the present invention.
Figure 103:
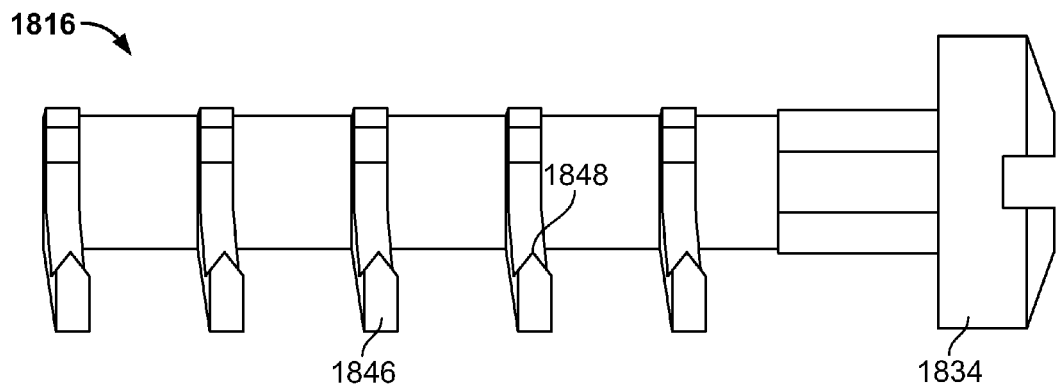
FIG. 103 is a side view of an alternate embodiment of a cam shaft securing mechanism according to the present invention illustrating cupped cam members.
Figure 104:
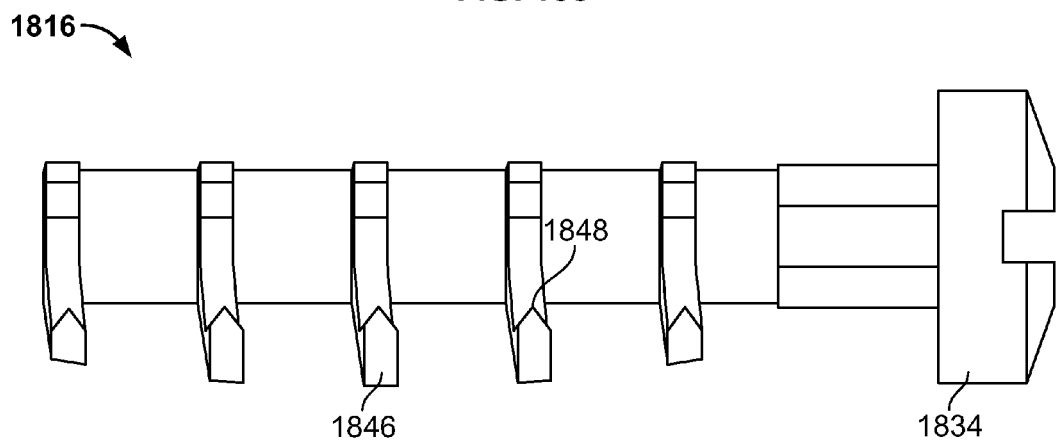
FIG. 104 is a side view of an alternate embodiment of a cam shaft securing mechanism according to the present invention illustrating contoured cam members.
Figure 105:
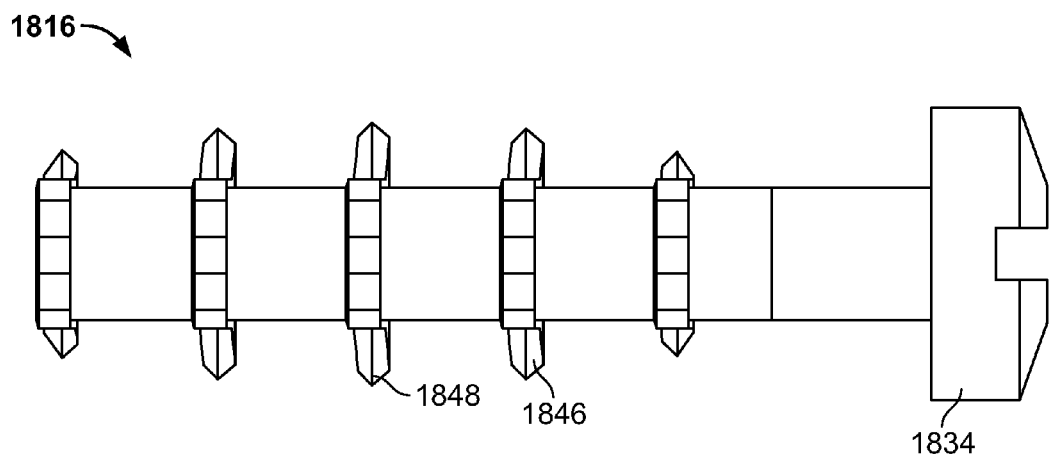
FIG. 105 is a top view of an alternate embodiment of a cam shaft securing mechanism according to the present invention illustrating contoured cam members.

The cam shafts 1816, cam members, lobes, or fins 1846 may take on different geometries and orientations to improve performance of the securing mechanism. For example, the camming fins may include serrations 2002, as shown in FIG. 102, divots, or recesses 2002 to promote boney ingrowth. The serrations 2002 may also help to cut the bone when the cam 1816 is rotated. In addition, the camming fins 1846 may be cupped or slanted, as shown in FIG. 103, to further promote anchoring of the implant 1752 to the vertebrae 1332, 1334. In a preferred embodiment, the camming fins 1846 are cupped about 8 degrees. Further, as shown in FIGS. 104 and 105, the camming fins 1846 may have an outside contour, such that shape or size of the cam fins 1846 varies from one end of the cam shaft 1816 to the other. The contour may match the profile of the endplates to take advantage of the softer bone in the center of the vertebrae 1332, 1334 as opposed to the harder-denser bone at the periphery of the vertebrae 1332, 1334. Further, the cam shafts 1816 may have any number of cam members 1846. In a preferred embodiment, each cam shaft 1816 may have between three and five cam members 1846. Larger implants may have five members 1846 per cam shaft 1816, while smaller implants may have only three. The cam shafts 1816 are preferably made from titanium or stainless steel, and may be coated with a bone-growth promoting substance, such as hydroxyapatite, tricalcium phosphates, or calcium phosphates.

Cam members 1846 that cut or imbed themselves into the bone provide advantages over other securing mechanisms. For instance, securing mechanisms that use static projections such as spikes and keels may rely on the subsidence of the bone around the securing mechanism to secure the implant. Static securing mechanisms are less desirable because they may not properly secure the implant to the bone until the bone begins to subside around the securing mechanism. Thus, the implant may tend to migrate prior to bone subsidence. However, dynamic securing mechanisms like cam members 1846 with cutting surfaces 1848 actively cut into or imbed themselves into the bone, instead of relying on the subsidence of the bone. In this manner, dynamic securing mechanisms create a much more reliable and stable connection between the implant 1752 and the vertebra 1332, 1334. These benefits translate into a more robust and reliable implant 1752, which means quicker recovery times and increased mobility for the patient.

Figure 106:
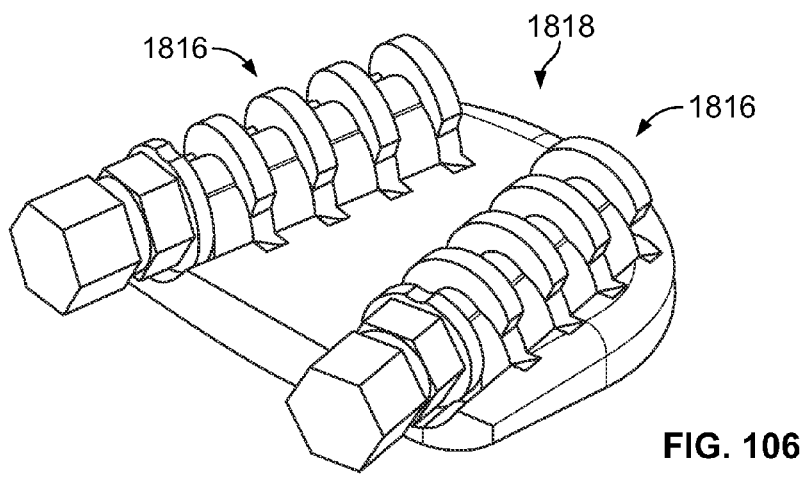
FIG. 106 is an anterolateral perspective view of an alternate embodiment of the artificial disc implant according to the present invention.

In another form, the cam shafts 1816 on the upper disc implant member 1818 may be disposed at converging or diverging angles, such as shown in FIG. 106. This orientation prevents migration of the implant 1752 not only in an anterior/posterior direction, but also substantially in the lateral direction as well. Naturally, the lower disc implant member 1822 may employ such a configuration.

It should be noted that the cam shafts 1816 provide certain advantages over other securing mechanisms, such as screws. For instance, screws do not provide a significant level of tactile feedback. It is very difficult for a surgeon to determine how far a screw has been turned, and therefore he may over- or under-rotate the screw, increasing the risk of implant migration and failure. In addition, metal screws may damage the implant if over-tightened. If the implant is made of a relatively soft material, such as PEEK, the metal screws will easily strip and damage the implant if over-tightened. Moreover, a surgeon is more likely to over-tighten a screw housed within a polymer because the screw is so much harder than the polymer that he will not be able to feel when the screw has been over-tightened. To alleviate this problem, the implant 1752 may be fabricated with a metal portion for housing the screw combined with a polymer, but this greatly increases the difficulty in manufacturing the implant 1752, as well as its cost, and is therefore less desirable. In addition, over-rotation of a screw may advance the screw beyond its intended range of motion, and may cause it to protrude from the implant and cause damage to vital areas in and around the spine. Because the cams do not advance or retreat as they are rotated, there is no danger that the cams 1846 will be accidentally projected into other vital areas.

Figure 107:
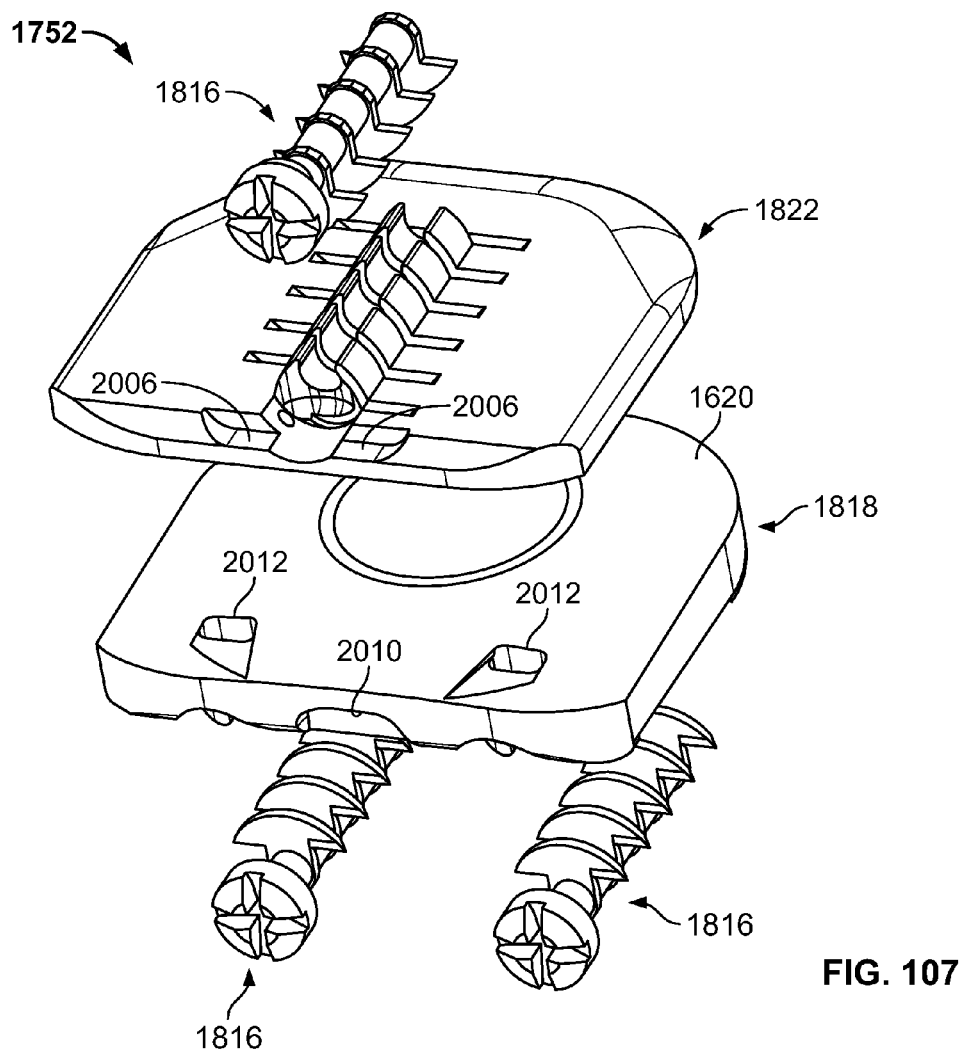
FIG. 107 is an inverted anterolateral exploded view of the artificial disc implant of FIG. 95.
Figure 108:
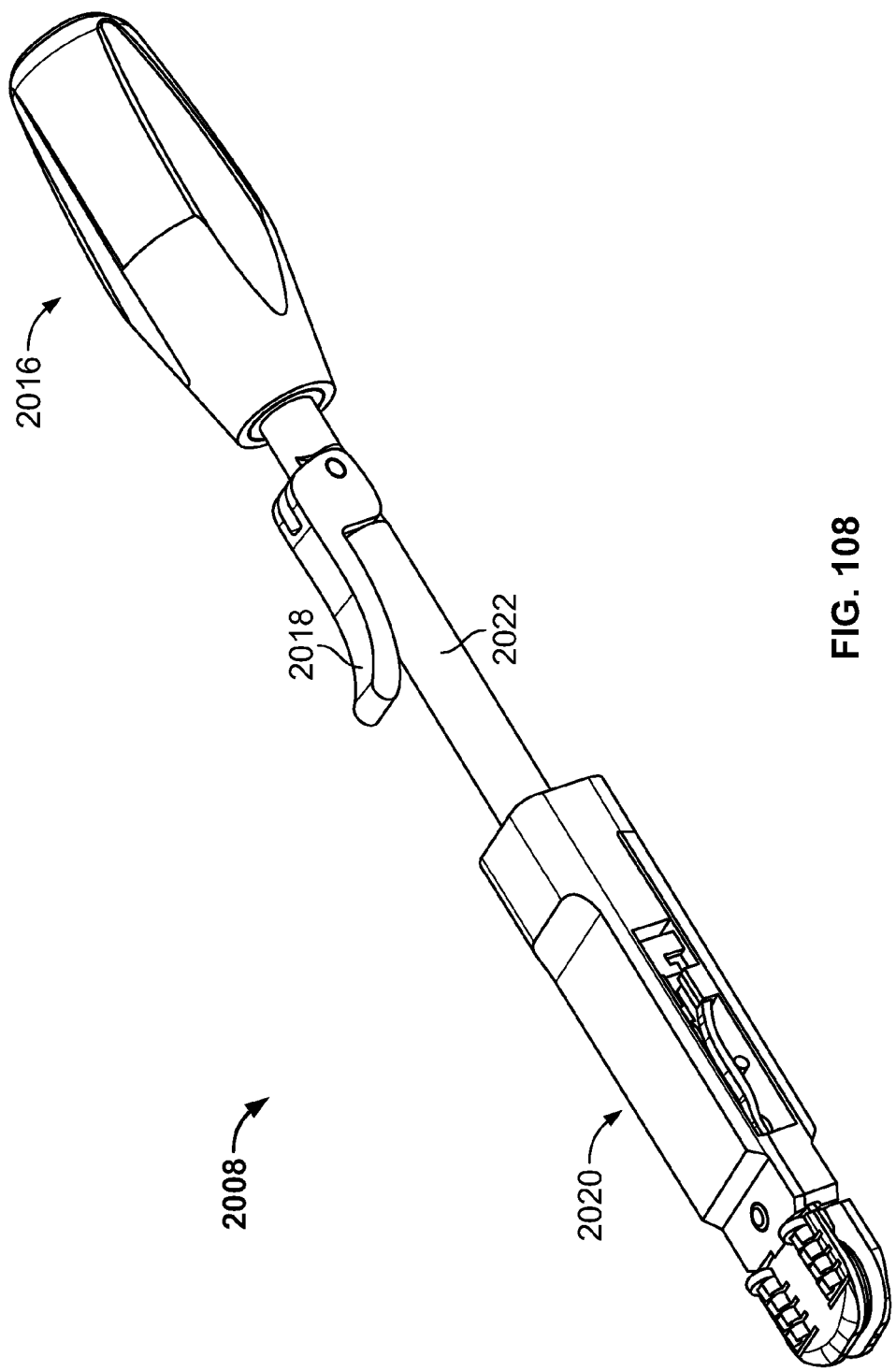
FIG. 108 is a perspective view of the implant inserter tool and artificial disc implant according to the present invention.
Figure 109:
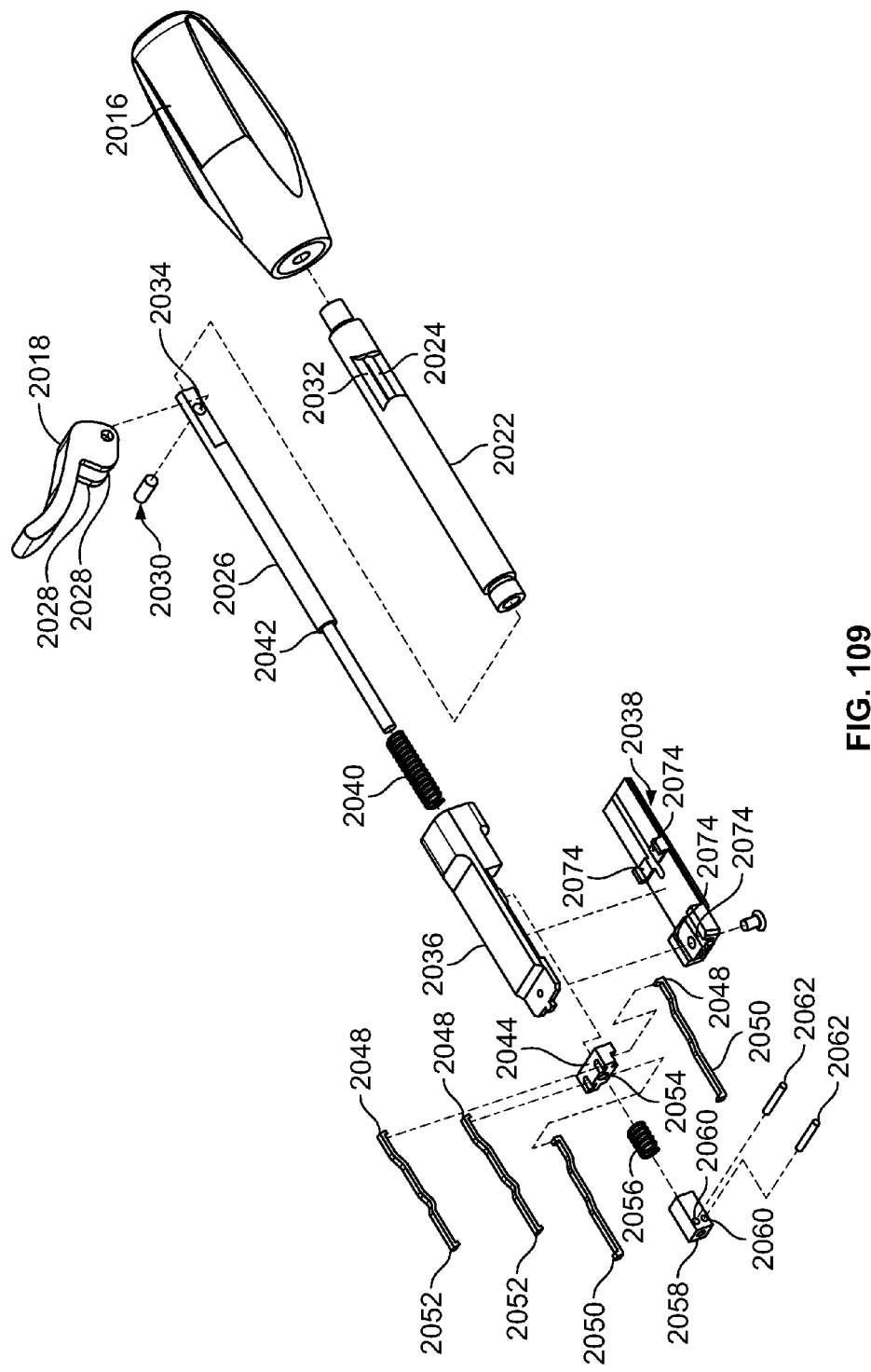
FIG. 109 is an exploded view of the implant inserter tool of FIG. 108.
Figure 110:
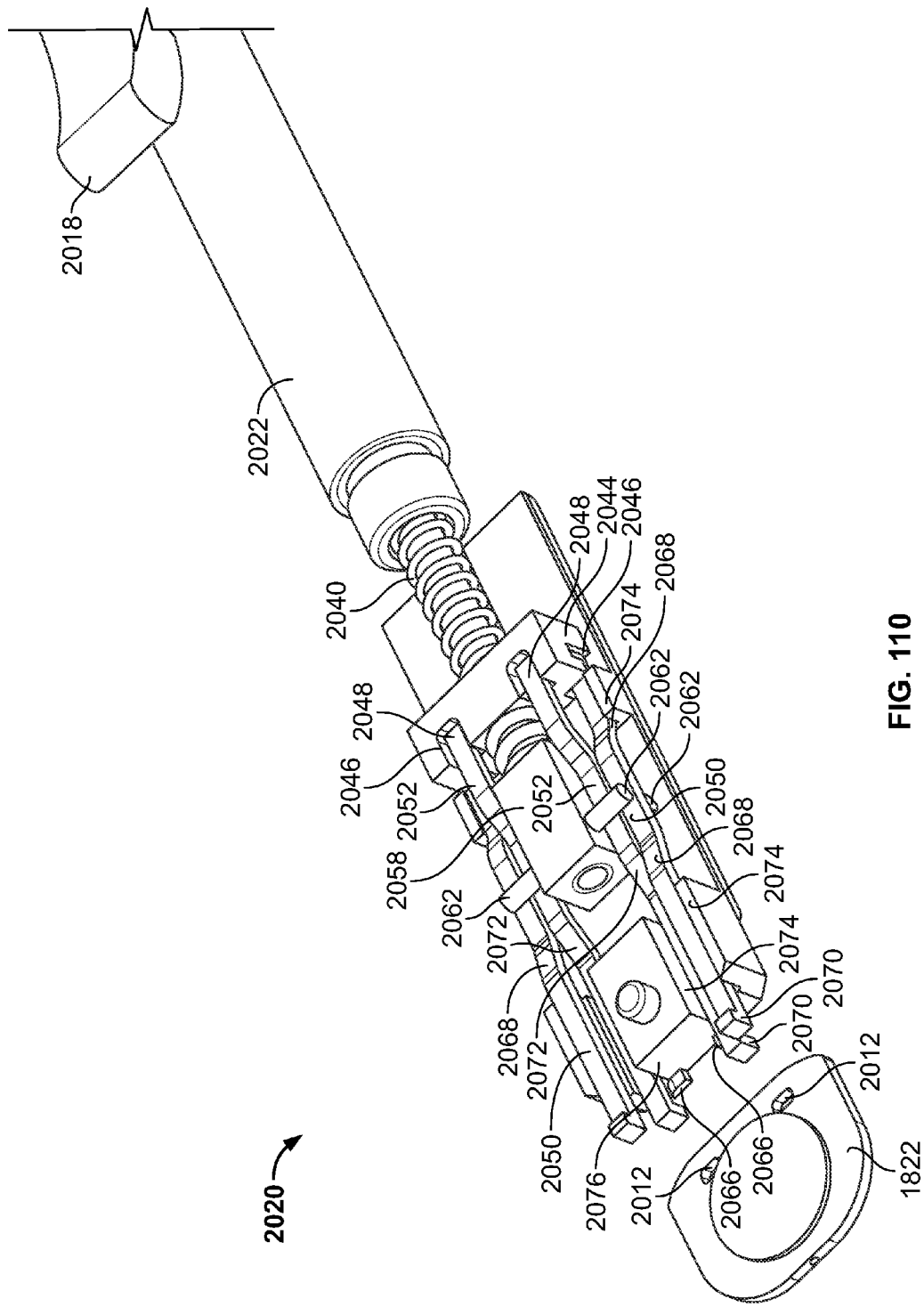
FIG. 110 is an enlarged perspective view of the implant and implant inserter tool of FIG. 108 with the upper disc member and upper housing member of the tool hidden for illustration purposes.

The disc implant 1752 according to the present embodiment has docking features for attaching with the implant insertion tool 2008, as shown in FIGS. 101, 107, and 108. The lower disc implant member 1822 has a shelf-like platform 2006 along its rear face on either side of the cam shaft 1816 for providing a contact surface for the implant insertion tool 2008. Similarly, the upper disc implant member 1818 has a shelf 2010 on its anterior face between the two upper cam shafts 1816 for providing a contact surface for the insertion tool 2008. The internal facing surfaces 1620 of both disc members 1818, 1822 each have a pair of generally rectangular recesses 2012 disposed therein to accept the gripping members 2014 of the insertion tool 2008. These docking features are advantageous because the insertion tool 2008 manipulates the implant 1752 substantially within the overall footprint of the implant 1752. This prevents trauma to the surrounding tissue and bone during insertion of the implant 1752 and removal of the inserter 2008 after the implant 1752 is inserted.

An insertion tool 2008 according to the present invention is shown in FIGS. 108-113B. The insertion tool 2008 is generally comprised of a handle portion 2016, an actuator, and a gripping mechanism 2020. Specifically, the handle portion 2016 is attached to a handle shaft 2022. The handle shaft 2022 has an annular bore 2024 therethrough for slidingly housing the push rod 2026. An actuator in the form of a cam lever 2018 with opposed camming surfaces is attached to the handle shaft 2022 and push rod 2026 with a pin connection 2030 extending between the camming surfaces 2028 and through opposed openings 2032 in the handle shaft 2022 and a bore 2034 in the push rod 2026. The handle shaft 2022 is attached at its forward end to upper and lower housing members 2036, 2038 which house the gripping mechanism 2020. A rear spring 2040 surrounds push rod 2026 and is biased between a collar 2042 on the handle shaft 2022 and the prong holder 2044. The prong holder 2044 is a rectangular shaped block with four L-shaped recesses 2046 (see FIG. 110), two on the upper face and two on the lower face for capturing the L-shaped anchoring ends 2048 of four prongs 2050, 2052. The prong holder 2044 has a cylindrical bore 2054 extending between the front and rear face for allowing the push rod 2026 to pass therethrough. The end of the push rod 2026 extends through a forward spring 2056, which is captured between the prong holder 2044 and a compression block 2058, which is attached to the end of the push rod 2026. The compression block 2058 is a rectangular block having an aperture in the rear face for attaching to the push rod 2026. In addition, the block 2058 has a pair of vertically aligned bores 2060 extending laterally through the side walls of the block 2058 for holding two pins 2062 operable to actuate the prongs 2050, 2052 into a disengaged position by temporarily deforming the prongs 2050, 2052 between the two pins.

Figure 111A:
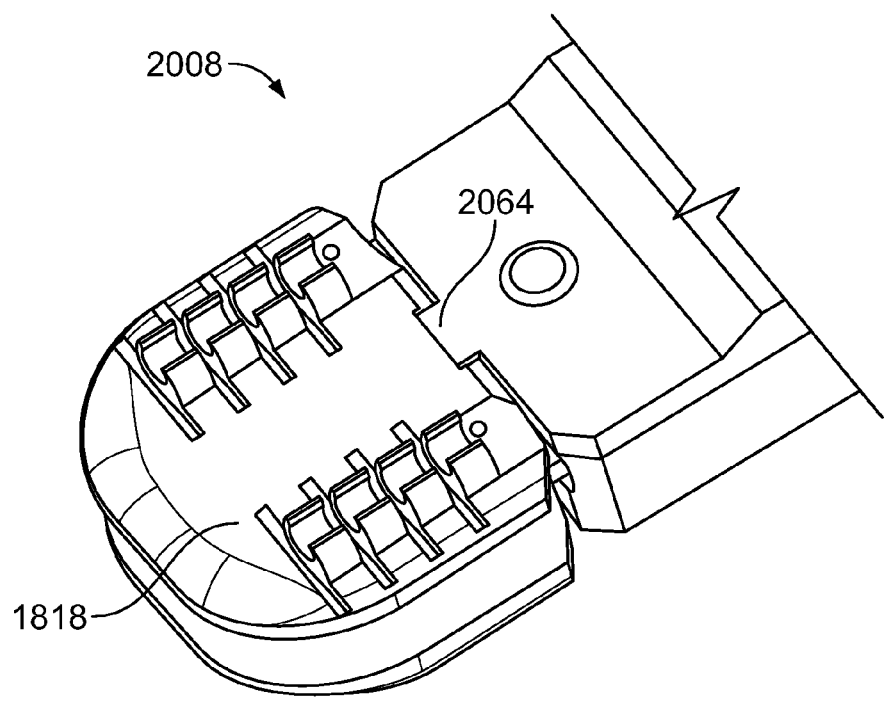
FIG. 111A is an enlarged perspective view of the implant and implant inserter tool of FIG. 108 illustrating the engagement of the implant and inserter tool.
Figure 111B:
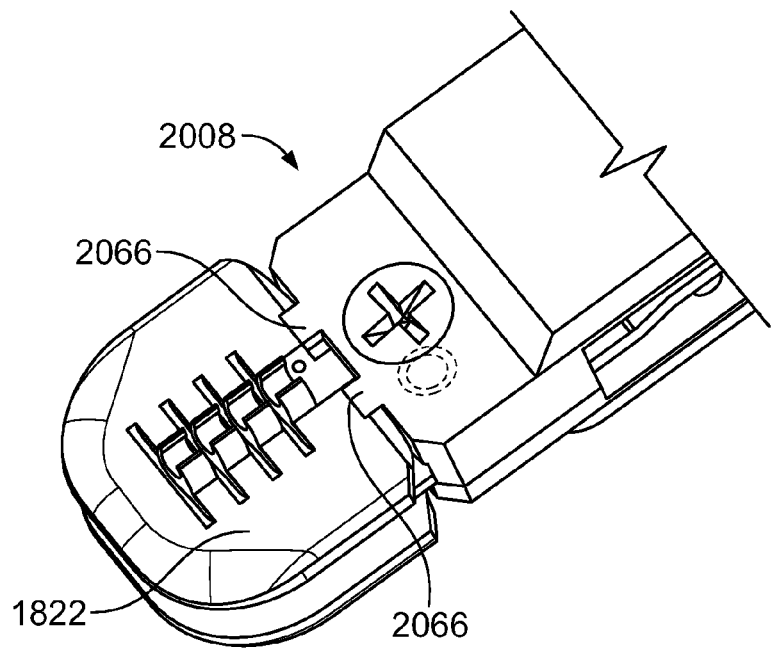
FIG. 111B is an enlarged perspective view of the underside of the implant and implant inserter tool of FIG. 108 illustrating the engagement of the implant and inserter tool.
Figure 112A:
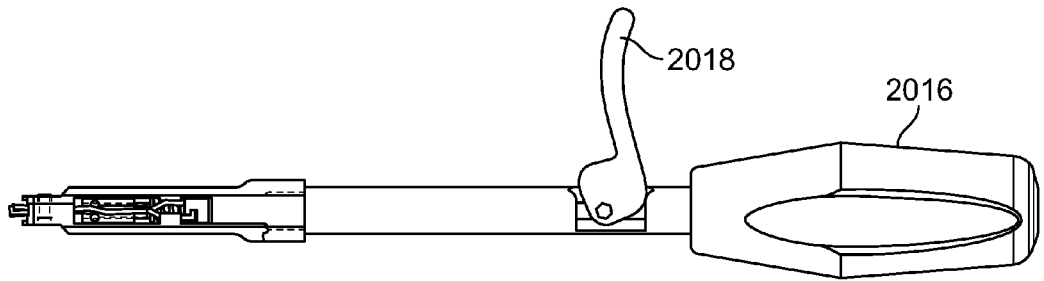
FIG. 112A is a side view of the implant inserter tool of FIG. 108 illustrating the initial disengaged position of the inserter tool.
Figure 112B:
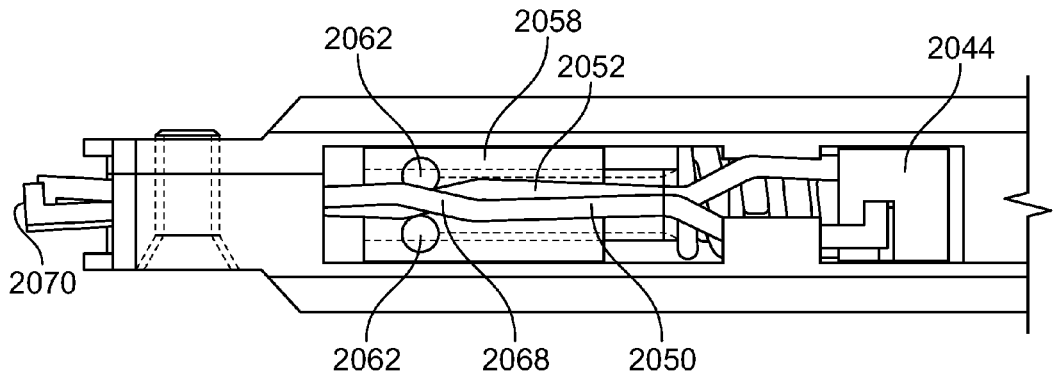
FIG. 112B is an enlarged side view of the gripping mechanism of the inserter tool of FIG. 108 illustrating the position of the gripping mechanism in the initial disengaged position.

The gripping mechanism 2020 includes two upper and two lower flexible prongs 2050, 2052 which operate in tandem with upper and lower tabs 2064, 2066 for gripping and holding the disc implant 1752 (shown in FIG. 111A-B). The prongs 2050, 2052 are made with a thin rectangular stainless steel shafts having a series of bends 2068, 2072. The upper prongs 2050 generally extend along the longitudinal axis of the insertion tool 2008 and have a series of two upward sloping bends 2068 so that the implant gripping end 2070 of the prong 2050 is vertically higher than the anchor end disposed in the prong holder 2044. The lower prongs 2052 are shaped in a similar manner, except that they have a series of two downward sloping bends 2072 so that the implant gripping end 2070 of the prong 2052 is vertically lower than the anchor end 2048 disposed in the prong holder 2044. The upper and lower prongs 2050, 2052 are paired adjacent each other and opposite the other pair along the outer lateral edges of the housing, such that the shaft 2026 and compression block 2058 may translate between the sets of prongs 2050, 2052. The upper and lower housing members 2036, 2038 have guide surfaces 2074 formed in the internal surfaces for guiding and securing the prongs 2050, 2052 to prevent them from becoming misaligned. The gripping ends 2070 of the prongs 2050, 2052 have an L-shape for being inserted into the recesses 2012 of the disc implant 1752.

Figure 113A:
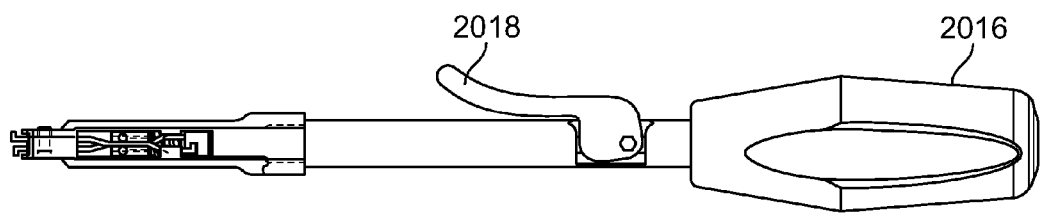
FIG. 113A is a side view of the implant inserter tool of FIG. 108 illustrating the engaged position of the inserter tool.
Figure 113B:
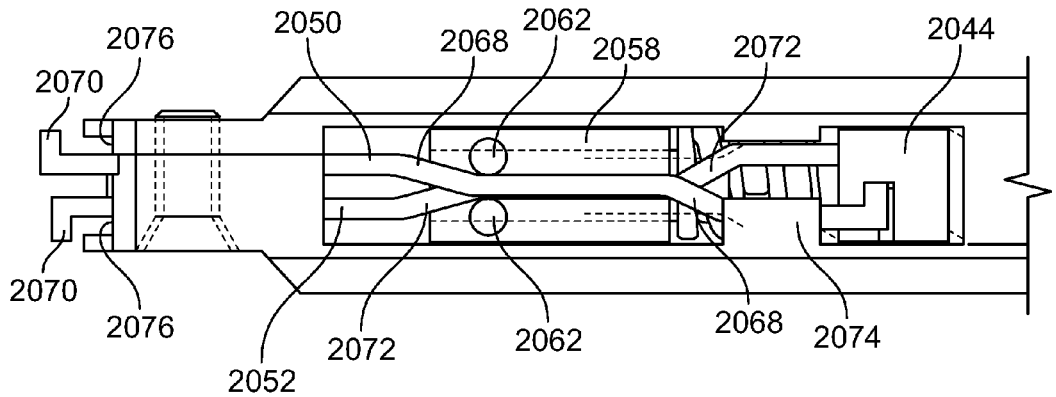
FIG. 113B is an enlarged side view of the gripping mechanism of the inserter tool of FIG. 108 illustrating the gripping mechanism in the engaged position.

In operation, the implant inserter tool prongs 2050, 2052 are movable in vertical and longitudinal directions to engage and disengage the disc implant 1752. In the initial disengaged position shown in FIG. 112A-B, the lever 2018 is in a released position. The compression block 2058 is pushed forward by the push rod 2026. The two opposed pins 2062 extending through the compression block 2058 are pushed over the sloping bends 2068, 2072 in the prongs 2050, 2052, which locally deform the prongs 2050, 2052 and forces the gripping ends 2070 of the prongs 2050, 2052 together, effectively lowering the gripping ends 2070 of the upper prongs 2050 and raising the gripping ends 2070 of the lower prongs 2052. In this manner, the forward portion of the inserter tool 2008 may be inserted between the upper and lower disc implant members 1818, 1822. To engage the implant 1752, the lever 2018 is pressed forwards, as shown in FIGS. 113A-B. This causes the push rod 2026 to pull the compression block 2058 rearwards. The opposed pins 2062 are thereby removed from the sloped portions 2068, 2072 of the prongs 2050, 2052, which allows the prongs 2050, 2052 to return to their original unflexed shape. In this manner, the gripping ends 2070 will spread vertically apart and engage the gripping recesses 2012 of the disc implant 1752. To provide a counteracting moment against the force imparted by the prongs 2050, 2052 on the implant 1752, tabs 2064, 2066 disposed on the forward ends of the housing members 2036, 2038 engage the implant 1752 on the shelves 2006, 2010 disposed on the rear portions of the disc members 1818, 1822, as shown in FIG. 111. In addition, as the lever 2018 is pushed forward, the compression block 2058 biases against the forward spring 2056, causing the prong holder 2044 to be biased rearwards against the rearward spring 2040. This causes the prong holder 2044 and the prongs 2050, 2052 to translate rearwards to pull the implant 1752 tight against the forward face of the housing members 2036, 2038. The limited range of motion of the lever 2018 prevents damage to the implant 1752 that may be caused by over-tightening the gripping mechanism 2020.

Once the implant 1752 is secured to the inserter 2008, the disc implant 1752 is then inserted into the intervertebral space 1330. The position of the implant 1752 may be determined using fluoroscopy to view the orientation of the implant 1752. Tantalum markers disposed in the frontal face of both the upper and lower disc members 1818, 1822 allow the surgeon to identify the position of the insertion end of the implant 1752. In addition, the cam shafts 1816, which are also radiopaque when made out of titanium or stainless steel, may be used to determine the orientation of the implant 1752. After the surgeon has placed the implant 1752 in the desired position, he releases the implant 1752 by lifting the lever 2018. The prongs 2050, 2052 are pushed forward and retracted vertically inwards, which releases the implant 1752. The surgeon then secures the implant 1752 in place by actuating the securing mechanism. Specifically, the surgeon turns each of the cams 1816 180 degrees using a driver, thereby deploying the cam members 1846 into the bone of the upper and lower vertebrae 1332, 1334. The surgeon can feel the resistance provided by the interaction between the camming surfaces of the cam shafts 1816 and the retainer member 1824 while deploying the cam members 1846. In this manner, he can determine when the cam members 1846 have been fully deployed. In addition, the camming surfaces of the cam shafts 1816 and the retainer members 1824 will prevent the cams 1816 from derotating and allowing the implant 1752 to migrate.

In other forms of the invention, the implant 1752 may comprise a pharmacological agent used for treating various spinal conditions, including degenerative disc disease, spinal arthritis, spinal infection, spinal tumor and osteoporosis. Such agents include antibiotics, analgesics, anti-inflammatory drugs, including steroids, and combinations thereof. Other such agents are well known to the skilled artisan. These agents are also used in therapeutically effective amounts. Such amounts may be determined by the skilled artisan depending on the specific case.

The pharmacological agents, if any, are preferably dispersed within the implant 1752 for in vivo release. The pharmacological agents may be dispersed in the spacer by adding the agents to the implant 1752 when it is formed, by soaking a formed implant 1752 in an appropriate solution containing the agent, or by other appropriate methods known to the skilled artisan. In other forms of the invention, the pharmacological agents may be chemically or otherwise associated with the implant 1752. For example, the agents may be chemically attached to the outer surface of the implant 1752.

Although the securing mechanisms and insertion tools have been described with reference to a disc replacement implant, the securing mechanisms and tools may be easily adapted for use with other artificial implants, such as fusion promoting implants, including vertebral body replacements, spinal cages, and the like. In addition, the invention described herein may also be applied to other motion preserving implants, such as those with articulating surfaces, including nucleus replacement implants. Moreover, the securing mechanisms, insertion tools, and methods described herein may be implemented in other weight-bearing joint implants, such as ankle, knee, or hip joint implants.

While the invention has been described with respect to specific examples including presently preferred modes of carrying out the invention, those skilled in the art will appreciate that there are numerous variations and permutations of the above described systems and techniques that fall within the spirit and scope of the invention as set forth in the claims.

The invention claimed is:

1. An intervertebral disc implant for being inserted between adjacent upper and lower vertebral bones, comprising:
    an upper bearing member;
    a lower bearing member;
    a body of the upper bearing member having an outer bearing surface for being disposed adjacent the upper vertebral bone;
    a body of the lower bearing member having an outer bearing surface for being disposed adjacent the lower vertebral bone;
    an articulation interface between the upper and lower bearing members for allowing relative movement therebetween with the bearing members configured to fit in an intervertebral space between upper and lower vertebral bones;
    a rotary securing member rotatably mounted to one of the bearing members to be carried by the one bearing member, so that the rotary securing member extends along the outer bearing surface of the one bearing member prior to being inserted into the intervertebral space, and is inserted together with the one bearing member into the intervertebral space, and after insertion of the rotary securing member and the one bearing member into the intervertebral space, the rotary securing member is arranged for being rotated for securing the one bearing member to the adjacent vertebral bone;
    a rotary shaft of the securing member having a longitudinal axis; and
    a plate-like bone-engaging portion having an outer periphery with an arcuate edge extending thereabout fixed to the rotary shaft to extend generally transversely therefrom such that rotation of the rotary shaft about the longitudinal axis causes a corresponding rotation of the bone engaging portion about the longitudinal axis to allow the rotary shaft of the rotary securing member to be rotated 180 degrees from an undeployed orientation with the bone-engaging portion out of engagement with the adjacent vertebral bone and a deployed orientation with the bone-engaging portion including the arcuate edge in imbedded engagement with the adjacent vertebral bone.

2. The intervertebral disc implant of claim 1, further comprising a second plate-like bone-engaging portion fixedly disposed on the rotary shaft and spaced apart along the longitudinal axis from the other bone-engaging portion for engaging with the adjacent vertebral bone to secure the one bearing member relative thereto.

3. The intervertebral disc implant of claim 2, further comprising a third plate-like bone-engaging portion fixedly disposed on the rotary shaft and spaced apart along the longitudinal axis from the other bone engaging portions for engaging with the adjacent vertebral bone to secure the one bearing member relative thereto.

4. The intervertebral disc implant of claim 1, wherein the securing member is substantially disposed within the body of the one bearing member such that it generally does not protrude outside of the outer bearing surface thereof with the bone-engaging portion oriented in the undeployed orientation.

5. The intervertebral disc implant of claim 1, wherein the shaft is disposed at least partially within a channel disposed on the body of the one bearing member.

6. The intervertebral disc implant of claim 1, wherein the plate-like bone-engaging portion comprises a leading cutting edge that extends outwardly from the rotary shaft for cutting into the adjacent vertebral bone as the bone-engaging portion is rotated into the deployed orientation to create a groove in the adjacent vertebral bone sized to fit the bone-engaging portion therein.

7. The intervertebral disc implant of claim 1, wherein the securing member further includes a drive head disposed on the shaft for providing a tool interface for interfacing with a tool to initiate deployment of the bone-engaging portion.

8. The intervertebral disc implant of claim 1, further comprising an implant engaging portion of the shaft for engaging with the one bearing member when the securing member is in the deployed orientation to secure the one bearing member with respect to the adjacent vertebral bone.

9. The intervertebral disc implant of claim 8, wherein the outer bearing surface of the one bearing member includes a ridge portion for providing a contact surface against which the implant engaging portion engages when the securing member is disposed in the deployed orientation for fixing the one bearing member relative to the adjacent bone.

10. The intervertebral disc implant of claim 8, wherein the implant engaging portion extends generally transversely to the shaft.

11. The intervertebral disc implant of claim 10, wherein the outer bearing surface of the one bearing member includes a mating recess for accepting at least a portion of the implant engaging portion with the securing member oriented in the deployed orientation.

12. The intervertebral disc implant of claim 10, wherein the securing member comprises a plurality of implant engaging portions and the outer bearing surface of the one bearing member includes a plurality of arcuate recesses for accepting at least a portion of the implant engaging portions of the securing member with the securing member in the deployed orientation.

13. The intervertebral disc implant of claim 1, wherein the securing member is connected to the one bearing member via a friction fit.

14. The intervertebral implant of claim 1, wherein the one bearing member has a mating portion including an elongate groove with a generally transversely oriented recess disposed thereon for mating with the bone-engaging portion of the securing member.

15. The intervertebral disc implant of claim 1, wherein at least one securing member is disposed on each of the upper and lower bearing members for fixing the bearing members relative to the adjacent vertebral bones.

16. The intervertebral disc implant of claim 1, wherein the securing member is connected to the body of the one bearing member via a securing member receiving portion disposed on the implant body having opposing inner surfaces spaced from each other for receiving the shaft.

17. The intervertebral disc implant of claim 16, wherein the securing member receiving portion includes at least one pair of opposed arms upon which the opposing inner surfaces are disposed for retaining the securing member therebetween with a friction fit.

18. The intervertebral disc implant of claim 17, wherein the securing member receiving portion includes at least two pairs of opposed arms for retaining the securing member therebetween, wherein the bone engaging member is disposed between the two pairs of opposed arms for providing a path for which the bone engaging member may travel between the undeployed and the deployed positions.

19. The intervertebral disc implant of claim 1, wherein the securing member includes a camming surface disposed adjacent a corresponding camming surface of the one of the bearing members to provide a frictional interface therebetween for providing resistance to deployment or retraction of the securing member.

20. The intervertebral disc implant of claim 19, wherein the camming surface is disposed on a drive head of the securing member.

21. The intervertebral disc implant of claim 1, wherein the upper and lower bearing members have inner surfaces that generally face each other and at least one recess in each inner surface for engaging with an insertion tool for facilitating low profile insertion of the implant into an intervertebral space.

22. The intervertebral disc implant of claim 1, wherein the upper and lower bearing members have trailing edges and a platform portion disposed on at least one of the trailing edges for interfacing with an insertion tool for facilitating low profile insertion of the implant into an intervertebral space.

23. The intervertebral disc implant of claim 1, wherein the bodies of the upper and lower bearing members are substantially free of protrusions that extend laterally, proximally, or anteriorly outside of an intervertebral space when implanted between adjacent upper and lower vertebral bones, such that the bodies are generally sized and configured for implantation substantially entirely within the intervertebral space.

24. The intervertebral disc implant of claim 1, wherein the bone-engaging portion is formed on the rotary shaft, such that the rotary securing member is monolithic.

25. An intervertebral disc implant, comprising:
    an upper bearing member;
    a lower bearing member;
    a body of the upper bearing member having an outer bearing surface for being disposed adjacent the upper vertebral bone;
    a body of the lower bearing member having an outer bearing surface for being disposed adjacent the lower vertebral bone;
    an articulation interface between the upper and lower bearing members for allowing relative movement therebetween with the bearing members configured to fit in an intervertebral space between upper and lower vertebral bones;

a rotary securing member for being mounted to one of the bearing members for being rotated for securing the one bearing member to the adjacent vertebral bone;

a rotary shaft of the securing member having a longitudinal axis; and a bone-engaging portion fixed to the rotary shaft to extend generally transversely therefrom such that rotation of the rotary shaft about the longitudinal axis causes a corresponding rotation of the bone engaging portion about the longitudinal axis, the bone engaging portion being sized relative to the one bearing member to allow the rotary shaft of the rotary securing member to be rotated 180 degrees from an undeployed orientation with the bone-engaging portion disposed within the body of the bearing member and out of engagement with the adjacent vertebral bone and a deployed orientation with the bone-engaging portion in engagement with the adjacent vertebral bone and the bone-engaging portion of the rotary shaft being configured such that rotation of the rotary shaft from the undeployed orientation 180 degrees to the deployed orientation does not cause the rotary shaft to advance along the longitudinal axis thereof and the outer bearing surface.

26. The intervertebral disc implant of claim 25, wherein substantially the entire securing member is disposed within the body of the one bearing member such that it generally does not protrude outside of the outer bearing surface thereof with the bone-engaging portion oriented in the undeployed orientation.

27. The intervertebral disc implant of claim 25, wherein the rotary shaft has a length and is disposed at least partially within a channel that extends along at least a majority of the length of the rotary shaft disposed on the body of the one bearing member.

28. The intervertebral implant of claim 25, wherein the one bearing member has a mating portion including an elongate groove having a longitudinal axis for receiving at least a portion of the rotary shaft of the securing member, and a transversely oriented recess disposed generally transversely to the longitudinal axis of the elongate groove in communication therewith for receiving the bone-engaging portion of the securing member in the undeployed orientation.

29. The intervertebral disc implant of claim 25, wherein the upper and lower bearing members have inner surfaces that generally face each other and at least one recess in each inner surface for engaging with an insertion tool for facilitating low profile insertion of the implant into an intervertebral space.

30. The intervertebral implant of claim 25, wherein the securing member is not connected to the one bearing member prior to being placed in the deployed orientation such that it may be inserted separately from the one bearing member into the intervertebral space.

31. An intervertebral disc implant for being inserted between adjacent upper and lower vertebral bones, comprising:

an upper bearing member;

a lower bearing member;

a body of the upper bearing member having an outer bearing surface for being disposed adjacent the upper vertebral bone;

a body of the lower bearing member having an outer bearing surface for being disposed adjacent the lower vertebral bone;

an articulation interface between the upper and lower bearing members for allowing relative movement therebetween with the bearing members configured to fit in an intervertebral space between upper and lower vertebral bones;

a rotary securing member rotatably mounted to one of the bearing members to be carried by the one bearing member, so that the rotary securing member extends along the outer bearing surface of the one bearing member prior to being inserted into the intervertebral space, and is inserted together with the one bearing member into the intervertebral space, and after insertion of the rotary securing member and the one bearing member into the intervertebral space, the rotary securing member is arranged for being rotated for securing the one bearing member to the adjacent vertebral bone;

a rotary shaft of the securing member having a longitudinal axis;

a bone-engaging portion fixed to the rotary shaft to extend generally transversely therefrom such that rotation of the rotary shaft about the longitudinal axis causes a corresponding rotation of the bone engaging portion about the longitudinal axis to allow the rotary shaft of the rotary securing member to be rotated from an undeployed orientation with the bone-engaging portion out of engagement with the adjacent vertebral bone and a deployed orientation with the bone-engaging portion in engagement with the adjacent vertebral bone; and a drive head of the securing member having a camming surface disposed adjacent a corresponding camming surface of the one of the bearing members to provide a frictional interface therebetween for providing resistance to deployment or retraction of the securing member.

* * * * *